US012214056B2

(12) United States Patent
Gersbach et al.

(10) Patent No.: US 12,214,056 B2
(45) Date of Patent: Feb. 4, 2025

(54) THERAPEUTIC APPLICATIONS OF CPF1-BASED GENOME EDITING

(71) Applicant: Duke University, Durham, NC (US)

(72) Inventors: Charles A. Gersbach, Durham, NC (US); Sarina Madhavan, Katy, TX (US); Christopher Nelson, Durham, NC (US)

(73) Assignee: Duke University, Durham, NC (US)

( * ) Notice: Subject to any disclaimer, the term of this patent is extended or adjusted under 35 U.S.C. 154(b) by 68 days.

(21) Appl. No.: 16/318,745

(22) PCT Filed: Jul. 19, 2017

(86) PCT No.: PCT/US2017/042921
§ 371 (c)(1),
(2) Date: Jan. 18, 2019

(87) PCT Pub. No.: WO2018/017754
PCT Pub. Date: Jan. 25, 2018

(65) Prior Publication Data
US 2019/0151476 A1 May 23, 2019

Related U.S. Application Data

(60) Provisional application No. 62/363,888, filed on Jul. 19, 2016.

(51) Int. Cl.
A61K 48/00 (2006.01)
A61K 31/7105 (2006.01)
A61K 38/46 (2006.01)
A61P 21/00 (2006.01)
C07K 14/47 (2006.01)
C12N 9/22 (2006.01)
C12N 15/11 (2006.01)
C12N 15/113 (2010.01)
C12N 15/90 (2006.01)

(52) U.S. Cl.
CPC ...... A61K 48/0066 (2013.01); A61K 31/7105 (2013.01); A61K 38/465 (2013.01); A61K 48/0008 (2013.01); A61K 48/0058 (2013.01); A61K 48/0075 (2013.01); A61K 48/0091 (2013.01); A61P 21/00 (2018.01); C07K 14/4708 (2013.01); C12N 9/22 (2013.01); C12N 15/111 (2013.01); C12N 15/113 (2013.01); C12N 15/907 (2013.01); C12N 2310/20 (2017.05); C12N 2320/33 (2013.01); C12N 2750/14143 (2013.01); Y02A 50/30 (2018.01)

(58) Field of Classification Search
CPC ............ A61K 48/0066; A61K 31/7105; A61K 38/465; A61K 48/0008; A61K 48/0058; A61K 48/0075; A61K 48/0091; A61P 21/00; C07K 14/4708; C12N 9/22; C12N 15/111; C12N 15/113; C12N 15/097; C12N 310/20; C12N 2320/33; C12N 2750/14143; Y02A 50/30
See application file for complete search history.

(56) References Cited

U.S. PATENT DOCUMENTS

| 3,687,808 A | 8/1972 | Merigan, Jr. |
| 4,469,863 A | 9/1984 | Ts'o et al. |
| 4,476,301 A | 10/1984 | Imbach et al. |
| 4,501,729 A | 2/1985 | Boucher et al. |
| 4,554,101 A | 11/1985 | Hopp |
| 4,587,044 A | 5/1986 | Miller et al. |
| 4,605,735 A | 8/1986 | Miyoshi et al. |
| 4,667,025 A | 5/1987 | Miyoshi et al. |
| 4,737,323 A | 4/1988 | Martin et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,013,830 A | 5/1991 | Ohsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |

(Continued)

FOREIGN PATENT DOCUMENTS

| AU | 2022318664 A1 | 2/2024 |
| CA | 2749305 A1 | 7/2010 |

(Continued)

OTHER PUBLICATIONS

US 11,898,176 B2, 02/2024, Gersbach et al. (withdrawn)
U.S. Appl. No. 61/831,481, filed Jun. 5, 2013.
U.S. Appl. No. 61/839,127, filed Jun. 25, 2013.
U.S. Appl. No. 61/904,911, filed Nov. 15, 2013.
U.S. Appl. No. 61/967,466, filed Mar. 19, 2014.
U.S. Appl. No. 61/981,575, filed Apr. 18, 2014.
PCT/US2014/041190, Jun. 5, 2014, WO 2014/197748, Dec. 11, 2014.
U.S. Appl. No. 14/895,316, filed Dec. 2, 2015, 2016/0201089, Jul. 14, 2016.

(Continued)

Primary Examiner — Jeremy C Flinders
Assistant Examiner — Alexander W Nicol
(74) Attorney, Agent, or Firm — Michael Best & Friedrich LLP

(57) ABSTRACT

Disclosed herein are therapeutic applications of CRISPR/Cpf1-based genome editing.

12 Claims, 5 Drawing Sheets

Specification includes a Sequence Listing.

(56) References Cited

U.S. PATENT DOCUMENTS

| | | |
|---|---|---|
| 5,139,941 A | 8/1992 | Muzyczka et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,219,740 A | 6/1993 | Miller et al. |
| 5,220,007 A | 6/1993 | Pederson et al. |
| 5,235,033 A | 8/1993 | Summerton et al. |
| 5,245,022 A | 9/1993 | Weis et al. |
| 5,254,469 A | 10/1993 | Warren, III |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,478,745 A | 12/1995 | Samulski et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,473 A | 4/1996 | Camerini-otero et al. |
| 5,510,475 A | 4/1996 | Agrawal et al. |
| 5,512,439 A | 4/1996 | Horner et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,593,972 A | 1/1997 | Weiner et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,652,355 A | 7/1997 | Metelev et al. |
| 5,652,356 A | 7/1997 | Agrawal |
| 5,658,784 A | 8/1997 | Eckner et al. |
| 5,663,312 A | 9/1997 | Chaturvedula et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,922 A | 12/1997 | Cook et al. |
| 5,714,331 A | 2/1998 | Buchardt et al. |
| 5,719,262 A | 2/1998 | Buchardt et al. |
| 5,741,683 A | 4/1998 | Zhou et al. |
| 5,750,692 A | 5/1998 | Cook et al. |
| 5,773,700 A | 6/1998 | Van Grinsven et al. |
| 5,962,428 A | 10/1999 | Carrano et al. |
| 6,057,152 A | 5/2000 | Samulski et al. |
| 6,140,081 A | 10/2000 | Barbas |
| 6,204,059 B1 | 3/2001 | Samulski et al. |
| 6,207,453 B1 | 3/2001 | Maass et al. |
| 6,268,213 B1 | 7/2001 | Samulski et al. |
| 6,268,490 B1 | 7/2001 | Imanishi et al. |
| 6,287,860 B1 | 9/2001 | Monia et al. |
| 6,453,242 B1 | 9/2002 | Eisenberg et al. |
| 6,462,254 B1 | 10/2002 | Vernachio et al. |
| 6,491,907 B1 | 12/2002 | Rabinowitz et al. |
| 6,534,261 B1 | 3/2003 | Cox, III et al. |
| 6,596,535 B1 | 7/2003 | Carter |
| 6,660,514 B1 | 12/2003 | Zolotukhin et al. |
| 6,734,291 B2 | 5/2004 | Kochkine et al. |
| 6,770,748 B2 | 8/2004 | Imanishi et al. |
| 6,794,499 B2 | 9/2004 | Wengel et al. |
| 6,951,753 B2 | 10/2005 | Shenk et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,074,596 B2 | 7/2006 | Darzynkiewicz et al. |
| 7,084,125 B2 | 8/2006 | Wengel |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,449,561 B1 | 11/2008 | Sommer et al. |
| 7,456,683 B2 | 11/2008 | Takano et al. |
| 7,572,582 B2 | 8/2009 | Wengel et al. |
| 7,588,772 B2 | 9/2009 | Kay et al. |
| 7,728,118 B2 | 6/2010 | Wood et al. |
| 7,745,651 B2 | 6/2010 | Heyes et al. |
| 7,790,449 B2 | 9/2010 | Gao et al. |
| 7,799,565 B2 | 9/2010 | Maclachlan et al. |

(56) References Cited

U.S. PATENT DOCUMENTS

| | | |
|---|---|---|
| 7,906,111 B2 | 3/2011 | Wilson et al. |
| 8,278,036 B2 | 10/2012 | Kariko et al. |
| 8,450,107 B1 | 5/2013 | Zhang et al. |
| 8,586,526 B2 | 11/2013 | Gregory et al. |
| 8,697,359 B1 | 4/2014 | Zhang et al. |
| 8,889,356 B2 | 11/2014 | Zhang |
| 8,993,233 B2 | 3/2015 | Zhang et al. |
| 9,139,554 B2 | 9/2015 | Hope et al. |
| 9,458,205 B2 | 10/2016 | Gregory et al. |
| 9,738,879 B2 | 8/2017 | Gersbach et al. |
| 9,828,582 B2 | 11/2017 | Perez-Pinera et al. |
| 9,834,791 B2 | 12/2017 | Zhang et al. |
| 9,890,364 B2 | 2/2018 | Joung et al. |
| 10,011,850 B2 | 7/2018 | Joung et al. |
| 10,190,106 B2 | 1/2019 | Wolfe et al. |
| 10,266,850 B2 | 4/2019 | Doudna et al. |
| 10,676,726 B2 | 6/2020 | Gersbach et al. |
| 10,676,735 B2 | 6/2020 | Gersbach et al. |
| 10,704,060 B2 | 7/2020 | Gersbach et al. |
| 10,711,256 B2 | 7/2020 | Gersbach et al. |
| 10,745,714 B2 | 8/2020 | Gersbach et al. |
| 11,155,796 B2 | 10/2021 | Gersbach et al. |
| 11,421,251 B2 | 8/2022 | Gersbach et al. |
| 11,427,817 B2 | 8/2022 | Josephs et al. |
| 2002/0160940 A1 | 10/2002 | Case et al. |
| 2004/0142025 A1 | 7/2004 | Maclachlan et al. |
| 2004/0175727 A1 | 9/2004 | Draghia-Akli et al. |
| 2004/0192593 A1 | 9/2004 | Draghia-Akli et al. |
| 2004/0204345 A1 | 10/2004 | Case et al. |
| 2006/0068395 A1 | 3/2006 | Wood et al. |
| 2006/0211647 A1 | 9/2006 | Khan |
| 2007/0042031 A1 | 2/2007 | Maclachlan et al. |
| 2007/0042462 A1 | 2/2007 | Hildinger |
| 2007/0059795 A1 | 3/2007 | Moore et al. |
| 2007/0185042 A1 | 8/2007 | Tsai et al. |
| 2007/0192880 A1 | 8/2007 | Muyan et al. |
| 2008/0070299 A1 | 3/2008 | Wood et al. |
| 2008/0090291 A1 | 4/2008 | Wood et al. |
| 2008/0200409 A1 | 8/2008 | Wilson et al. |
| 2009/0018031 A1 | 1/2009 | Trinklein et al. |
| 2010/0035968 A1 | 2/2010 | Rasmussen et al. |
| 2010/0076057 A1 | 3/2010 | Sontheimer et al. |
| 2010/0261175 A1 | 10/2010 | Rasmussen et al. |
| 2010/0267018 A1 | 10/2010 | Wengel et al. |
| 2011/0145940 A1 | 6/2011 | Voytas et al. |
| 2011/0197290 A1 | 8/2011 | Fahrenkrug et al. |
| 2011/0236353 A1 | 9/2011 | Wilson et al. |
| 2011/0263682 A1 | 10/2011 | De Kimpe et al. |
| 2011/0286957 A1 | 11/2011 | Prieve et al. |
| 2011/0301073 A1 | 12/2011 | Gregory et al. |
| 2011/0301218 A1 | 12/2011 | Bozzoni et al. |
| 2012/0195917 A1 | 8/2012 | Sahin et al. |
| 2012/0207744 A1 | 8/2012 | Mendlein et al. |
| 2013/0274129 A1 | 10/2013 | Katzen et al. |
| 2013/0323001 A1 | 12/2013 | Ueki et al. |
| 2014/0068797 A1 | 3/2014 | Doudna et al. |
| 2014/0140969 A1 | 5/2014 | Beausejour et al. |
| 2014/0170753 A1 | 6/2014 | Zhang |
| 2014/0179006 A1 | 6/2014 | Zhang |
| 2014/0186958 A1 | 7/2014 | Zhang et al. |
| 2014/0234975 A1 | 8/2014 | Silva et al. |
| 2014/0295557 A1 | 10/2014 | Joung et al. |
| 2014/0309177 A1 | 10/2014 | Perez-Pinera et al. |
| 2014/0315862 A1 | 10/2014 | Kaye |
| 2014/0356956 A1 | 12/2014 | Church et al. |
| 2014/0357530 A1 | 12/2014 | Zhang et al. |
| 2014/0377868 A1 | 12/2014 | Joung et al. |
| 2015/0024499 A1 | 1/2015 | Brouns et al. |
| 2015/0031089 A1 | 1/2015 | Lindstrom |
| 2015/0044772 A1 | 2/2015 | Zhao |
| 2015/0045413 A1 | 2/2015 | De Visser et al. |
| 2015/0056705 A1 | 2/2015 | Conway et al. |
| 2015/0079064 A1 | 3/2015 | Gersbach et al. |
| 2015/0159178 A1 | 6/2015 | Green et al. |
| 2015/0166980 A1 | 6/2015 | Liu et al. |
| 2015/0225717 A1 | 8/2015 | Lee et al. |
| 2015/0252358 A1 | 9/2015 | Maeder et al. |
| 2016/0002634 A1 | 1/2016 | Sazani et al. |
| 2016/0040189 A1 | 2/2016 | Kennedy et al. |
| 2016/0058889 A1* | 3/2016 | Olson ............... C12N 15/113 424/94.6 |
| 2016/0177278 A1 | 6/2016 | Wolfe et al. |
| 2016/0199419 A1 | 7/2016 | Miura |
| 2016/0201089 A1 | 7/2016 | Gersbach et al. |
| 2016/0281166 A1 | 9/2016 | Bhattacharjee et al. |
| 2016/0354487 A1 | 12/2016 | Zhang et al. |
| 2017/0002316 A1 | 1/2017 | Gascón Jiménez et al. |
| 2017/0198308 A1 | 7/2017 | Qi et al. |
| 2017/0204407 A1 | 7/2017 | Gilbert et al. |
| 2017/0283831 A1 | 10/2017 | Zhang et al. |
| 2017/0298331 A1 | 10/2017 | Gersbach et al. |
| 2017/0327806 A1 | 11/2017 | Joung et al. |
| 2017/0362635 A1 | 12/2017 | Chamberlain et al. |
| 2018/0023064 A1 | 1/2018 | Gersbach et al. |
| 2018/0073012 A1 | 3/2018 | Liu et al. |
| 2018/0094238 A1 | 4/2018 | Perez-Pinera et al. |
| 2018/0127780 A1 | 5/2018 | Liu et al. |
| 2018/0135109 A1 | 5/2018 | Jayaram et al. |
| 2018/0201951 A1 | 7/2018 | Guilak et al. |
| 2018/0237771 A1 | 8/2018 | Kim et al. |
| 2018/0251735 A1 | 9/2018 | Ko |
| 2018/0271069 A1 | 9/2018 | Min et al. |
| 2018/0280539 A1 | 10/2018 | Debs et al. |
| 2018/0291370 A1 | 10/2018 | Gersbach et al. |
| 2018/0305689 A1 | 10/2018 | Sætrom et al. |
| 2018/0305704 A1 | 10/2018 | Zhang |
| 2018/0305719 A1 | 10/2018 | Perez-Pinera et al. |
| 2018/0319850 A1 | 11/2018 | Payne et al. |
| 2018/0320197 A1 | 11/2018 | Gersbach et al. |
| 2018/0327740 A1 | 11/2018 | Gifford et al. |
| 2018/0334685 A1 | 11/2018 | Yeo et al. |
| 2018/0334688 A1 | 11/2018 | Gersbach et al. |
| 2018/0353615 A1 | 12/2018 | Gersbach et al. |
| 2019/0032049 A1 | 1/2019 | Naldini et al. |
| 2019/0038776 A1 | 2/2019 | Pyle et al. |
| 2019/0048337 A1 | 2/2019 | Hsu et al. |
| 2019/0062790 A1 | 2/2019 | Doudna et al. |
| 2019/0078119 A1 | 3/2019 | Wilson et al. |
| 2019/0106710 A1 | 4/2019 | Zhang et al. |
| 2019/0127713 A1 | 5/2019 | Gersbach et al. |
| 2019/0134221 A1 | 5/2019 | Bumcrot et al. |
| 2019/0136229 A1 | 5/2019 | Josephs et al. |
| 2019/0183932 A1 | 6/2019 | Mackall et al. |
| 2019/0194633 A1 | 6/2019 | Gersbach et al. |
| 2019/0201402 A1 | 7/2019 | Jiang et al. |
| 2019/0248854 A1 | 8/2019 | Tremblay et al. |
| 2019/0264232 A1 | 8/2019 | Hou et al. |
| 2019/0351074 A1 | 11/2019 | Ahituv et al. |
| 2019/0359959 A1 | 11/2019 | Jaenisch et al. |
| 2019/0374655 A1 | 12/2019 | Kabadi et al. |
| 2020/0002731 A1 | 1/2020 | Frendewey et al. |
| 2020/0056206 A1 | 2/2020 | Tremblay et al. |
| 2020/0080108 A1 | 3/2020 | Jaskula-Ranga et al. |
| 2020/0109406 A1 | 4/2020 | Miller et al. |
| 2020/0123533 A1 | 4/2020 | Wang et al. |
| 2020/0216549 A1 | 7/2020 | Fukumura et al. |
| 2020/0216810 A1 | 7/2020 | Metelitsa et al. |
| 2020/0260698 A1 | 8/2020 | Kyrychenko et al. |
| 2020/0275641 A1 | 9/2020 | Min et al. |
| 2020/0318139 A1 | 10/2020 | Gersbach et al. |
| 2020/0332307 A1 | 10/2020 | Hummel et al. |
| 2020/0347105 A1 | 11/2020 | Gersbach et al. |
| 2020/0385695 A1 | 12/2020 | Gersbach et al. |
| 2021/0002665 A1 | 1/2021 | Gersbach et al. |
| 2021/0032654 A1 | 2/2021 | Gersbach et al. |
| 2021/0040460 A1 | 2/2021 | Gersbach et al. |
| 2021/0322577 A1 | 10/2021 | Lande et al. |
| 2022/0098561 A1 | 3/2022 | Gersbach et al. |
| 2022/0177879 A1 | 6/2022 | Gersbach et al. |
| 2022/0184229 A1 | 6/2022 | Gersbach et al. |
| 2022/0195406 A1 | 6/2022 | Gersbach et al. |
| 2022/0305141 A1 | 9/2022 | Gersbach et al. |
| 2022/0307015 A1 | 9/2022 | Gersbach et al. |
| 2022/0364124 A1 | 11/2022 | Gersbach et al. |

(56) References Cited

U.S. PATENT DOCUMENTS

| | | |
|---|---|---|
| 2022/0396790 A1 | 12/2022 | Gersbach et al. |
| 2023/0032846 A1 | 2/2023 | Gersbach et al. |
| 2023/0047669 A1 | 2/2023 | Josephs et al. |
| 2023/0201375 A1 | 6/2023 | Gersbach et al. |
| 2023/0257723 A1 | 8/2023 | Gersbach et al. |
| 2023/0304000 A1 | 9/2023 | Josephs et al. |
| 2023/0348870 A1 | 11/2023 | Gersbach et al. |
| 2023/0349888 A1 | 11/2023 | Gersbach et al. |
| 2023/0383270 A1 | 11/2023 | Gersbach et al. |
| 2023/0383297 A1 | 11/2023 | Gersbach et al. |
| 2023/0392132 A1 | 12/2023 | Gersbach et al. |
| 2024/0026352 A1 | 1/2024 | Gersbach et al. |
| 2024/0052328 A1 | 2/2024 | Kwon et al. |
| 2024/0067968 A1 | 2/2024 | Cosgrove et al. |

FOREIGN PATENT DOCUMENTS

| | | |
|---|---|---|
| CA | 2981508 A1 | 10/2016 |
| CA | 3086885 A1 | 7/2019 |
| CA | 3101477 A1 | 12/2019 |
| EP | 2620161 A1 | 7/2013 |
| EP | 3009511 A2 | 4/2016 |
| EP | 3199632 A1 | 8/2017 |
| EP | 3712272 A1 | 9/2020 |
| EP | 3209783 B1 | 11/2021 |
| EP | 3995584 A1 | 5/2022 |
| JP | 2013-509159 A | 3/2013 |
| JP | 2015-534817 A | 12/2015 |
| JP | 2016-521452 A | 7/2016 |
| JP | 2016-521452 A2 | 7/2016 |
| JP | 2016-521975 A | 7/2016 |
| JP | 2016-523082 A | 8/2016 |
| KR | 20190134673 A | 12/2019 |
| WO | 1991/18114 A1 | 11/1991 |
| WO | WO1992/000387 A1 | 1/1992 |
| WO | WO1993/007883 A1 | 4/1993 |
| WO | WO 1993/024640 A2 | 12/1993 |
| WO | WO 1994/016737 A1 | 8/1994 |
| WO | WO1998/053058 A1 | 11/1998 |
| WO | WO1998/053059 A1 | 11/1998 |
| WO | WO1998/053060 A1 | 11/1998 |
| WO | 2000/028004 A1 | 5/2000 |
| WO | 2001/083793 A2 | 11/2001 |
| WO | WO 2001/083783 A2 | 11/2001 |
| WO | 2001/092551 A2 | 12/2001 |
| WO | WO2002/016536 A1 | 2/2002 |
| WO | WO2003/016496 A2 | 2/2003 |
| WO | WO2003/042397 A2 | 5/2003 |
| WO | WO2003/072788 A1 | 9/2003 |
| WO | WO2005/033321 A2 | 4/2005 |
| WO | WO2006/110689 A2 | 10/2006 |
| WO | WO2007/019301 A2 | 2/2007 |
| WO | WO 2008/006028 A2 | 1/2008 |
| WO | WO2008/070859 A2 | 6/2008 |
| WO | WO2010/053572 A2 | 5/2010 |
| WO | WO2010/075424 A2 | 7/2010 |
| WO | WO2010/144740 A1 | 12/2010 |
| WO | WO 2011/036640 A2 | 3/2011 |
| WO | WO2011/126808 A2 | 10/2011 |
| WO | WO 2011/154427 A1 | 12/2011 |
| WO | WO2012/136476 A1 | 10/2012 |
| WO | WO2012/170930 A1 | 12/2012 |
| WO | WO2013/049493 A1 | 4/2013 |
| WO | WO2013/098244 A1 | 7/2013 |
| WO | WO2013/143555 A1 | 10/2013 |
| WO | WO 2013/163628 A2 | 10/2013 |
| WO | WO2013/176772 A1 | 11/2013 |
| WO | WO2013/182683 A1 | 12/2013 |
| WO | WO2014/018423 A2 | 1/2014 |
| WO | WO2014/059255 A1 | 4/2014 |
| WO | 2014/081855 A1 | 5/2014 |
| WO | WO2014/065596 A1 | 5/2014 |
| WO | 2014/093595 A1 | 6/2014 |
| WO | 2014/093622 A2 | 6/2014 |
| WO | 2014/093712 A1 | 6/2014 |
| WO | 2014/099744 A1 | 6/2014 |
| WO | WO2014/089290 A1 | 6/2014 |
| WO | WO2014/093479 A1 | 6/2014 |
| WO | WO2014/093655 A2 | 6/2014 |
| WO | WO2014/093661 A2 | 6/2014 |
| WO | WO2014/093709 A1 | 6/2014 |
| WO | WO2014/144288 A1 | 9/2014 |
| WO | WO2014/144592 A2 | 9/2014 |
| WO | WO2014/152432 A2 | 9/2014 |
| WO | WO2014/172470 A2 | 10/2014 |
| WO | WO2014/186585 A2 | 11/2014 |
| WO | 2014/197568 A2 | 12/2014 |
| WO | WO2014/191128 A1 | 12/2014 |
| WO | WO 2014/197748 A2 | 12/2014 |
| WO | WO2014/204726 A1 | 12/2014 |
| WO | WO2014/204728 A1 | 12/2014 |
| WO | WO2015/006747 A2 | 1/2015 |
| WO | 2015/021457 A2 | 2/2015 |
| WO | WO2015/017519 A1 | 2/2015 |
| WO | 2015/035139 A2 | 3/2015 |
| WO | WO2015/035136 A2 | 3/2015 |
| WO | WO2015/048690 A1 | 4/2015 |
| WO | 2015/070083 A1 | 5/2015 |
| WO | 2015/089462 A1 | 6/2015 |
| WO | WO2015/089419 A1 | 6/2015 |
| WO | WO2015/089427 A1 | 6/2015 |
| WO | WO2015/089465 A1 | 6/2015 |
| WO | WO2015/089486 A2 | 6/2015 |
| WO | WO2015/126927 A2 | 8/2015 |
| WO | WO2015/155686 A2 | 10/2015 |
| WO | WO2015/161276 A2 | 10/2015 |
| WO | 2015/195621 A1 | 12/2015 |
| WO | 2016/011080 A2 | 1/2016 |
| WO | WO2016/011070 A2 | 1/2016 |
| WO | WO2016/049258 A2 | 3/2016 |
| WO | WO2016/063264 A1 | 4/2016 |
| WO | 2016/070070 A1 | 5/2016 |
| WO | WO2016/081924 A1 | 5/2016 |
| WO | WO2016/094880 A1 | 6/2016 |
| WO | WO2016/114972 A1 | 7/2016 |
| WO | WO2016/123578 A1 | 8/2016 |
| WO | WO 2016/130600 A2 | 8/2016 |
| WO | WO 2016/161380 A1 | 10/2016 |
| WO | 2016/205613 A1 | 12/2016 |
| WO | WO2016/187717 A1 | 12/2016 |
| WO | WO2017/015637 A1 | 1/2017 |
| WO | 2017/016915 A1 | 2/2017 |
| WO | WO2017/035416 A2 | 3/2017 |
| WO | WO2017/049266 A2 | 3/2017 |
| WO | WO2017/049407 A1 | 3/2017 |
| WO | WO2017/066497 A2 | 4/2017 |
| WO | WO2017/070632 A2 | 4/2017 |
| WO | WO2017/072590 A1 | 5/2017 |
| WO | WO2017/075478 A2 | 5/2017 |
| WO | WO2017/095967 A2 | 6/2017 |
| WO | 2017/139505 A2 | 8/2017 |
| WO | WO2017/165859 A1 | 9/2017 |
| WO | 2017/180976 A1 | 10/2017 |
| WO | WO 2017/180915 A2 | 10/2017 |
| WO | 2017/193029 A3 | 11/2017 |
| WO | 2018/002812 A1 | 1/2018 |
| WO | 2018/005805 A1 | 1/2018 |
| WO | 2018/013932 A1 | 1/2018 |
| WO | 2018/017483 A1 | 1/2018 |
| WO | WO2018/017751 A1 | 1/2018 |
| WO | WO2018/031762 A1 | 2/2018 |
| WO | WO2018/035388 A1 | 2/2018 |
| WO | WO2018/035495 A1 | 2/2018 |
| WO | 2018/039145 A1 | 3/2018 |
| WO | 2018/098480 A1 | 5/2018 |
| WO | WO2018/081504 A1 | 5/2018 |
| WO | 2018/107003 A1 | 6/2018 |
| WO | WO2018/129296 A1 | 7/2018 |
| WO | 2018/162702 A1 | 9/2018 |
| WO | 2018/179578 A1 | 10/2018 |
| WO | WO2018/191388 A1 | 10/2018 |
| WO | 2019/009682 A2 | 1/2019 |
| WO | 2019/023291 A2 | 1/2019 |
| WO | WO2019/002590 A1 | 1/2019 |

(56) References Cited

FOREIGN PATENT DOCUMENTS

| | | |
|---|---|---|
| WO | 2019/036599 A1 | 2/2019 |
| WO | 2019/046755 A1 | 3/2019 |
| WO | WO2019/067786 A1 | 4/2019 |
| WO | WO2019/077001 A1 | 4/2019 |
| WO | WO 2019/079514 A1 | 4/2019 |
| WO | 2019/084050 A1 | 5/2019 |
| WO | WO 2019/092505 A1 | 5/2019 |
| WO | 2019/113472 A1 | 6/2019 |
| WO | 2019/123014 A1 | 6/2019 |
| WO | 2019/136216 A1 | 7/2019 |
| WO | WO2019/144061 A1 | 7/2019 |
| WO | 2019/204750 A1 | 10/2019 |
| WO | 2019/213626 A1 | 11/2019 |
| WO | WO2019/232069 A1 | 12/2019 |
| WO | 2020/018918 A1 | 1/2020 |
| WO | 2020/132226 A1 | 6/2020 |
| WO | WO2020/124257 A1 | 6/2020 |
| WO | 2020/168133 A1 | 8/2020 |
| WO | WO2020/163396 A1 | 8/2020 |
| WO | WO2020/210776 A1 | 10/2020 |
| WO | WO2020/214609 A1 | 10/2020 |
| WO | WO 2020/214613 A1 | 10/2020 |
| WO | WO2020/257665 A1 | 12/2020 |
| WO | WO2021/026516 A1 | 2/2021 |
| WO | WO2021/034984 A2 | 2/2021 |
| WO | WO2021/034987 A1 | 2/2021 |
| WO | WO2021/055956 A1 | 3/2021 |
| WO | WO2021/067878 A1 | 4/2021 |
| WO | WO2021/113536 A1 | 6/2021 |
| WO | WO2021/222268 A1 | 11/2021 |
| WO | WO2021/222314 A1 | 11/2021 |
| WO | WO2021/222327 A1 | 11/2021 |
| WO | WO2021/222328 A1 | 11/2021 |
| WO | WO2021/226555 A2 | 11/2021 |
| WO | 2022/038264 A1 | 2/2022 |
| WO | 2022/087321 A1 | 4/2022 |
| WO | 2022/103935 A1 | 5/2022 |
| WO | 2022/104159 A1 | 5/2022 |
| WO | 2022/133062 A1 | 6/2022 |
| WO | WO2022/187288 A2 | 9/2022 |
| WO | 2023/010133 A2 | 2/2023 |
| WO | 2023/137471 A1 | 7/2023 |
| WO | 2023/137472 A2 | 7/2023 |
| WO | 2023/164670 A2 | 8/2023 |
| WO | 2023/164671 A2 | 8/2023 |
| WO | WO2023/200998 A2 | 10/2023 |
| WO | 2024/015881 A2 | 1/2024 |
| WO | 2024/064642 A2 | 3/2024 |
| WO | 2024/081937 A1 | 4/2024 |
| WO | 2024/040254 A3 | 5/2024 |

OTHER PUBLICATIONS

U.S. Appl. No. 15/991,333, filed May 29, 2018.
U.S. Appl. No. 62/260,712, filed Nov. 30, 2015.
U.S. Appl. No. 62/330,336, filed May 2, 2016.
PCT/US2016/064285, Nov. 30, 2016, WO 2017/095967, Jun. 8, 2017.
U.S. Appl. No. 15/779,633, filed May 29, 2018, 2018/0353615, Dec. 13, 2018.
U.S. Appl. No. 62/332,297, filed May 5, 2016.
PCT/US2017/031351, May 5, 2017, WO 2017/193029, Nov. 9, 2017.
U.S. Appl. No. 16/098,464, filed Nov. 2, 2018.
Aartsma-Rus, A. et al., "Antisense-mediated exon skipping a versatile tool with therapeutic and research applications," RNA 13, 2007, 1609-1624.
Aartsma-Rus, A. et al., "Exploring the frontiers of therapeutic exon skipping for Duchenne muscular dystrophy by double targeting within one or multiple exons," Mol Ther, 2006, 14:401-407.
Aartsma-Rus, A. et al., "Theoretic applicability of antisense-mediated exon skipping for Duchenne muscular dystrophy mutations," Hum Mutat, 2009, 30:293-299.

Adler, A.F. et al., "Nonviral direct conversion of primary mouse embryonic fibroblasts to neuronal cells," Molecular therapy, 2012 Nucleic acids 1, e32.
Aiuti, A. et al., "Lentiviral hematopoietic stem cell gene therapy inpatients with Wiskott-Aldrich syndrome," Science, 2013, 341(6148): p. 1233151.
Anders, S. et al., "Differential expression analysis for sequence count data," Genome biology 11, 2010, R106.
Anguela, X. M. et al., "Robust ZFN-mediated genome editing in adult hemophilic mice," Blood, 2013, 122:3283-3287.
Aoki, Y. et al., "Bodywide skipping of exons 45-55 in dystrophic mdx52 mice by systemic antisense delivery," Proc Natl Acad Sci USA, 2012, 109:13763-13768.
Bae et al., "Cas-OFFinder: a fast and versatile algorithm that searches for potential off-target sites of Cas9 RNA-guided endonucleases," Bioinformatics, 2014, 30: 1473-1475.
Bartsevich, V. V. et al., "Engineered zinc finger proteins for controlling stem cell fate," Stem Cells 21, 2003, 632-637.
Bauer et al., "An erythroid enhancer of BCL11A subject to genetic variation determines fetal hemoglobin level," Science 342, 2013, 253-257.
Beerli, R. R. et al., "Chemically regulated zinc finger transcription factors," J Biol Chem, 2000, 275(42): p. 32617-27.
Beerli, R.R. et al., "3rd Engineering polydactyl zinc-finger transcription factors," Nat Biotechnol 20, 2002, 135-141.
Beerli, R.R. et al., "3rd Positive and negative regulation of endogenous genes by designed transcription factors," Proc Natl Acad Sci U S A 97, 2000, 1495-1500.
Beerli, R.R. et al., "3rd Toward controlling gene expression at will: specific regulation of the erbB-2/Her-2 promoter by using polydactyl zinc finger proteins constructed from modular building blocks," Proc Natl Acad Sci U S A 95, 1998, 14628-14633.
Beltran, A. et al., "Re-activation of a dormant tumor suppressor gene maspin by designed transcription factors," Oncogene 26, 2007, 2791-2798.
Benedetti, S. et al., "Repair or Replace? Exploiting Novel Gene and Cell Therapy Strategies for Muscular Dystrophies," FEBS Journal (2013).
Berghella, L. et al., "Reversible immortalization of human myogenic cells by site-specific excision of a retrovirally transferred oncogene," Human gene therapy 10, 1999, 1607-1617.
Bhakta, M. S. et al., "Highly active zinc-finger nucleases by extended modular assembly," Genome Res, 2013, 530538.
Bidou, L. et al., "Sense from nonsense: therapies for premature stop codon diseases," Trends in Molecular Medicine 18, 2012, 679-688.
Bladen et al., "The TREAT-NMD DMD Global Database: analysis of more than 7,000 Duchenne muscular dystrophy mutations," Human Mutation, 2015, 36(4):395-402.
Blancafort, P. et al., "3rd Scanning the human genome with combinatorial transcription factor libraries," Nat Biotechnol 21, 2003, 269-274.
Boch, J. et al., "Breaking the code of DNA binding specificity of TAL-type III effectors," Science 326, 2009, 1509.
Bowles, D. E. et al., "Phase 1 Gene Therapy for Duchenne Muscular Dystrophy Using a Translation Optimized AAV Vector," Molecular Therapy 20, 2012, 443-455.
Brunet, E. et al., "Chromosomal translocations induced at specific loci inhuman stem cells," Proc Natl Acad Sci USA, 2009, 106:10620-10625.
Baler et al., "Energy-sensing factors coactivator peroxisome proliferator-activated receptor gamma coactivator 1-alpha (PGC-1 alpha) and AMP-activated protein kinase control expression of inflammatory mediators in liver," The Journal of Biological Chemistry, vol. 287, No. 3, pp. 1847-1860, Jan. 13, 2012.
Bultmann, S. et al., "Targeted transcriptional activation of silent oct4 pluripotency gene by combining designer TALEs and inhibition of epigenetic modifiers," Nucleic Acids Res 40, 2012, 5368-5377.
Canver et al., "BCL11A enhancer dissection by Cas9-mediated in situ saturating mutagenesis," Nature, 2015, 527:192-197.
Cerletti, M. et al., "Highly efficient, functional engraftment of skeletal muscle stem cells in dystrophic muscles," Cell 134, 2008, 37-47.

(56) References Cited

OTHER PUBLICATIONS

Cermak, T. et al., "Efficient design and assembly of custom TALEN and other TAL effector-based constructs for DNA targeting," Nucleic Acids Res 30, 2011, e82.
Chapdelaine, P. et al., "Meganucleases can restore the reading frame of a mutual dystrophin," Gene therapy 17, 2010, 846-858.
Cheng, A. W. et al., "Multiplexed activation of endogenous genes by CRISPR-on, an RNA-guided transcriptional activator system," Cell Res, 2013, 23(10): p. 1163-1171.
Cho, S. W. et al., "Analysis of off-target effects of CRISPR/Cas-derived RNA-guided endonucleases and nickases," Genome Res, 2014, 24:132-141.
Cho, S.W. et al., "Targeted genome engineering in human cells with the Cas9 RNA-guided endonuclease," Nat Biotechnol 31, 2013, 230-232.
Christian, M. et al., "Targeting DNA double-strand breaks with TAL effector nucleases," Genetics 186, 2010, 757-761.
Cirak, S. et al., "Exon skipping and dystrophin restoration in patients with Duchenne muscular dystrophy after systemic phosphorodiamidate morpholino oligomer treatment: an open-label, phase 2, dose-escalation study," Lancet 378, 2011, 595-605.
Cong, L. et al., "Multiplex Genome Engineering Using CRISPR/Cas Systems," Science 339, 2013, 819-823.
Cornu et al., "Quantification of zinc finger nuclease-associated toxicity," Meth Mol Biol, 2010, 649:237-245.
Cornu, T. I. et al., "DNA-binding specificity is a major determinant of the activity and toxicity of zinc-finger nucleases," Mol Ther, 2008, 16:352-358.
Cradick, T. J. et al., "CRISPR/Cas9 systems targeting beta-globin and CCR5 genes have substantial off-target activity," Nucleic Acids Res, 2013, 41(20): p. 9584-92.
Darabi, R. et al., "Human ES-and iPS-derived myogenic progenitors restore dystrophin and improve contractility upon transplantation in dystrophic mice," Cell Stem Cell 10, 2012, 610-619.
Dezawa, M. et al., "Bone marrow stromal cells generate muscle cells and repair muscle degeneration," Science Signaling 309, 2005, 314.
Ding Q. et al., "A TALEN Genome-Editing System for Generating Human Stem Cell-Based Disease Models," 2013, Cell Stem Cell 12, 238-251.
Ding Q. et al., "Enhanced efficiency of human pluripotent stem cell genome editing through replacing TALENs with CRISPRs," Cell Stem Cell, 2013, 12:393-394.
Doyle, E. L. et al., "TAL Effector-Nucleotide Targeter (TALE-NT) 2.0: tools for TAL effector design and target prediction," Nucleic Acids Res 40, 2012, W117-122.
Doyon, Y. et al., "Enhancing zinc-finger-nuclease activity with improved obligate heterodimeric architectures," Nat Methods 8, 2010, 74-79.
Edelstein et al., "Gene therapy clinical trials worldwide 1989-2004—an overview," J. Gene Med. vol. 6, pp. 597-602, 2004.
Esvelt et al., "Orthogonal Cas9 proteins for RNA-guided gene regulation and editing," Nature Methods 2013, 10(11): p. 1116-21.
Fagerlund et al., "The Cpf1 CRISPR-Cas protein expands genome-editing tools," Genome Biology, 2015, 16:251.
Farinelli, G. et al., "Lentiviral vectors for the treatment of primary immunodeficiencies," J Inherit Metab Dis, 2014.
Farzadfard, F. et al., "Tunable and Multifunctional Eukaryotic Transcription Factors Based on CRISPR/Cas," ACS Synth Biol, 2013, 604-613.
Flanigan, K. M. et al., "Mutational spectrum of DMD mutations in dystrophinopathy patients: application of modern diagnostic techniques to a large cohort," Human mutation 30, 2009, 1657-1666.
Fonfara, I. et al., "Phylogeny of Cas9 determines functional exchangeability of dual-RNA and Cas9 among orthologous type II CRISPR-Cas systems," Nucleic Acids Res, 2013.
Forget, "Molecular basis of hereditary persistence of fetal hemoglobin," Ann N Y Acad Sci, 1998, 850, 38-44.

Fu, Y. et al., "High-frequency off-target mutagenesis induced by CRISPR-Cas nucleases in human cells," Nat Biotechnol, 2013, 31(9): p. 822-6.
Fu, Y., et al., "Improving CRISPR-Cas nuclease specificity using truncated guide RNAs," 2014, Nat Biotechnol 32, 279-284.
Gaj, T. et al., "Targeted gene knockout by direct delivery of zinc-finger nuclease proteins," Nature Methods, 2012.
Gaj, T. et al., "ZFN, TALEN, and CRISPR/Cas-based methods for genome engineering," Trends Biotechnol, 2013, 31:397-405.
Garg, A. et al., "Engineering synthetic TAL effectors with orthogonal target sites," Nucleic Acids Res 40, 2012, 7584-7595.
GenBank Accession AF214528.1 (2000).
GenBank Accession X51934.1 (1997).
Gertz, J. et al., "Transposase mediated construction of RNA-seq libraries," Genome Res 22, 2012, 134-141.
Gilman et al., "Distal CCAAT box deletion in the a gamma globin gene of two black adolescents with elevated fetal A gamma globin," Nucleic Acids Res 16, 1988, 10635-10642.
Goemans, N. M. et al., "Systemic administration of PRO051 in Duchenne's muscular dystrophy," The New England journal of medicine 364, 2011, 1513-1522.
Gou, D. et al., "A novel approach for the construction of multiple shRNA expression vectors," J Gene Med, 2007, 9(9): p. 751-63.
Graslund, T. et al., "3rd Exploring strategies for the design of artificial transcription factors: targeting sites proximal to known regulatory regions for the induction of gamma-globin expression and the treatment of sickle cell disease," J Biol Chem 280, 2005, 3707-3714.
Gregorevic, P. et al., "Systemic delivery of genes to striated muscles using adeno-associated viral vectors," Nat. Med, 2004, 10:828-834.
Guo, J. et al., "Directed evolution of an enhanced and highly efficient Fok1 cleavage domain for zinc finger nucleases," J Mol Biol, 2010.
Guschin, D. Y. et al., "A rapid and general assay for monitoring endogenous gene modification," Methods Mol Biol 649, 2010, 247-256.
Hakim et al., "Systemic gene transfer reveals distinctive muscle transduction profile of tyrosine mutant AAV-1, -6, and -9 in neonatal dogs," Mol. Ther. Methods Clin. Dev., 2014, 1:14002.
Hockemeyer, D. et al., "Efficient targeting of expressed and silent genes in human ESCs and iPSCs using zinc-finger nucleases," Nat Biotechnol, 2009, 27(9): p. 851-7.
Hockemeyer, D. et al., "Genetic engineering of human pluripotent cells using TALE nucleases," Nat Biotechnol 29, 2011, 731-734.
Hoffman, E. P. et al., "Dystrophin: the protein product of the Duchenne muscular dystrophy locus," Cell, 1987, 51:919.
Hou, Z. et al., "Efficient genome engineering in human pluripotent stem cells using Cas9 from Neisseria meningitidis," Proc Natl Acad Sci USA, 2013, 110:15644-15649.
Hsu et al. (2012) "Dissecting Neural Function Using Targeted Genome Engineering Technologies", ACS Chem. Neurosci., pp. 603-610.
Hsu et al., "DNA targeting specificity of RNA-guided Cas9 nucleases," Nature Biotechnology 31, 2013, 827-832 doi:10.1038/nbt.2647.
Humbert et al., "Targeted gene therapies: tools, applications, optimization", Critical Reviews in Biochemistry and Molecular Biology, CRC Press, vol. 47, No. 3, Apr. 2012, pp. 264-281.
Hwang, W. Y. et al., "Efficient genome editing in zebrafish using CRISPR-Cas system," Nat Biotechnol, 2013, 31(3): p. 227-9.
Iyombe-Engembe et al., "Efficient Restoration of the Dystrophin Gene Reading Frame and Protein Structure in DMD Myoblasts Using the CinDel Method," Molecular Therapy—Nucleic Acids, 2016, 5:e283.
Jinek, M. et al., "A programmable dual-RNA-guided DNA endonuclease in adaptive bacterial immunity," Science 337, 2012, 816-821.
Jinek, M. et al., "RNA-programmed genome editing in human cells," eLife 2, e00471, 2013.
Jinek, M. et al., "Structures of Cas9 endonucleases reveal RNA-mediated conformational activation," Science, 2014, 343(6176): p. 1247997.
Joung, J. K. et al., "TALENs: a widely applicable technology for targeted genome editing," Nature Reviews Molecular Cell Biology 14, 2013, 49-55.

(56) References Cited

OTHER PUBLICATIONS

Kayali et al., "Site-directed gene repair of the dystrophin gene mediated by PNA-ssODNs," Human Molecular Genetics, vol. 19, No. 16, Aug. 15, 2010, pp. 3266-3281.
Kearns, N. A. et al., "Cas9 effector-mediated regulation of transcription and differentiation in human pluripotent stem cells," Development, 2014, 141(1): p. 219-23.
Kim, H. et al., "Surrogate reporters for enrichment of cells with nuclease-induced mutations," Nat Methods, 2011, 8:941-943.
Kim, Y. et al., "TALENs and ZFNs are associated with different mutation signatures," Nat Methods, 2013.
Kimura, E. et al., "Cell-lineage regulated myogenesis for dystrophin replacement: a novel therapeutic approach for treatment of muscular dystrophy," Hum Mol Genet 17, 2008, 2507-2517.
Kleinstiver et al., "Broadening the targeting range of *Staphylococcus aureus* CRISPR-Cas9 by modifying PAM recognition," Nature Biotechnology, 2015, 7 pages.
Konermann, S. et al., "Optical control of mammalian endogenous transcription and epigenetic states," Nature, 2013, 500(7463): p. 472-6.
Konieczny, P. et al., "Gene and cell-mediated therapies for muscular dystrophy," Muscle Nerve, 2013, 47:649-663.
Kubokawa, I. et al., "Molecular characterization of the 5'-UTR of retinal dystrophin reveals a cryptic intron that regulates translational activity," Molecular Vision, 2010, vol. 16, pp. 2590-2597.
Kyte et al., "A Simple Method for Displaying the Hydropathic Character of a Protein," J. Mol. Biol., 1982, 157:105-132.
Lai et al., "Partial restoration of cardiac function with ΔPDZ nNOS in aged mdx model of Duchenne cardiomyopathy," Hum Mol Genet, 2014, 23(12): 3189-3199.
Langmead, B. et al., "Ultrafast and memory-efficient alignment of short DNA sequences to the human genome," Genome biology 10, 2009, R25.
Larson, M. H. et al., "CRISPR interference (CRISPRi) for sequence-editing control of gene expression," Nat Protoc, 2013, 8(11): p. 2180-96.
Latta-Mahieu et al., "Gene transfer of a chimeric trans-activator is immunogenic and results in short-lived transgene expression," Human Gene Therapy, vol. 13, No. 13, pp. 1611-1620, Sep. 2002.
Lattanzi, L. et al., "High efficiency myogenic conversion of human fibroblasts by adenoviral vector-mediated MyoD gene transfer. An alternative strategy for ex vivo gene therapy of primary myopathies," the Journal of clinical investigation 101, 1998, 2119-2128.
Lee, H. J. et al., "Targeted chromosomal deletions in human cells using zinc finger nucleases," Genome research 20, 2010, 81-89.
Li, D. et al., "Marginal level dystrophin expression improves clinical outcome in a strain of dystrophin/utrophin double knockout mice," PLoS One, 2010, 5:e15286.
Li, H. et al, "In vivo genome editing restores haemostasis in a mouse model of haemophilia," Nature 475, 2011, 217-221.
Li, T. et al., "Modularly assembled designer TAL effector nucleases for targeted gene knockout and gene replacement in eukaryotes," Nucleic Acids Research, 2011, vol. 39, No. 14, pp. 6315-6325.
Li, Y. et al., "Transcription activator-like effector hybrids for conditional control and rewiring of chromosomal transgene expression," Scientific reports 2, 2012, 897.
Liang, J.C. et al., "Engineering biological systems with synthetic RNA molecules," Mol Cell 43, 2011, 915-926.
Lohmueller, J.J. et al., "A tunable zinc finger-based framework for Boolean logic computation in mammalian cells," Nucleic Acids Res 40, 2012, 5180-5187.
Long et al., "Postnatal genome editing partially restores dystrophin expression in a mouse model of muscular dystrophy," Science, 2016, 351(6271):400-403.
Lovric, J. et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.
Lu, Q. L. et al., "The status of exon skipping as a therapeutic approach to duchenne muscular dystrophy," Molecular Therapy 19, 2011, 9-15.
Lund et al. "Promoter-targeted phage display selections with preassembled synthetic zinc finger libraries for endogenous gene regulation." Journal of Molecular Biology, vol. 340, pp. 599-613, 2004.
Luo et al., "Synthetic DNA delivery systems," Nature Biotechnology, vol. 18, pp. 33-37, 2000.
Maeder et al., "Robust, synergistic regulation of human gene expression using TALE activators," Nature Methods, vol. 10, No. 3, pp. 243-246, Feb. 10, 2013, including pp. 1/14-14/14 of Supplementary Material.
Maeder, M. L., "Targeted DNA demethylation and activation of endogenous genes using programmable TALE-TET1 fusion proteins," Nat Biotechnol, 2013, 31(12): p. 1137-42.
Maeder, M.L. et al., "Robust, synergistic regulation of human gene expression using TALE activators," Nat Methods 10, 2013, 243-245.
Mali, P. et al., "Cas9 as a versatile tool for engineering biology," Nat Methods, 2013, 10(10): p. 957-63.
Mali, P. et al., "CAS9 transcriptional activators for target specificity screening and paired nickases for cooperative genome engineering," Nat Biotechnol, 2013, 31(9): p. 833-8.
Mali, P. et al., "RNA-Guided Human Genome Engineering via Cas9," Science 339, 2013, 823-826.
Mamchaoui, K. et al., "Immortalized pathological human myoblasts: towards a universal tool for the study of neuromuscular disorders," Skelet Muscle 1, 2011, 1-11.
Mendell, J. R. et al., "Dystrophin immunity in Duchenne's muscular dystrophy," New England Journal of Medicine 363, 2010, 1429-1437.
Mendenhall, E. M. et al., "Locus-specific editing of histone modification at endogenous enhancers," Nat Biotechnol, 2013, 31(12): p. 1133-6.
Mercer, A. C. et al., "Regulation of Endogenous Human Gene Expression by Ligand-Inducible TALE Transcription Factors," ACS Synth Biol, 2013.
Miller, J.C. et al., "A TALE nuclease architecture for efficient genome editing," Nat Biotechnol 29, 2011, 143-148.
Moscou, M. J. et al., "A simple cipher governs DNA recognitionby TAL effectors," Science 326, 2009, 1501.
Muir et al., "Engraftment potential of dermal fibroblasts following in vivo myogenic conversion in immunocompetent dystrophic skeletal muscle," Mol. Ther. Methods Clin. Dev., 2014, 1:14025.
Murphy et al., "The in vitro transcription of the 7SK RNA gene by RNA polymerase III is dependable only on the presence of an upstream promoter," Cell, 1987, 51:81-87.
Mussolino, C. et al., "A novel TALE nuclease scaffold enables high genome editing activity in combination with low toxicity," Nucleic Acids Res 39, 2011, 9283-9293.
Myslinski et al., "An unusually compact external promoter for RNA polymerase III transcription of the human H1RNA gene," Nucleic Acids Res, 2001, 29:2502-2509.
Negroni, E. et al., "In Vivo Myogenic Potential of Human CD133+ Muscle-derived Stem Cells: A Quantitative Study," Molecular Therapy 17, 2009, 1771-1778.
Nelson et al., "In vivo genome editing improves muscle function in a mouse model of Duchenne muscular dystrophy," Science, 2016, 351(6271):403-7.
Nishimasu, H. et al., "Crystal structure of cas9 in complex with guide RNA and target DNA Cell," 2014, 156(5): p. 935-49.
Ohshima et al., "Nucleotide sequence of mouse genomic loci including a gene or pseudogene for U6 (4.85) nuclear RNA," Nucleic Acids Res, 1981, 9:5145-5158.
Ousterout et al., "Correction of dystrophin expression in cells from duchenne muscular dystrophy patients through genomic excision of exon 51 by zinc finger nucleases," Molecular Therapy 23, 2015, 523-532.
Ousterout et al., "Multiplex CRISPR/Cas9-based genome editing for correction of dystrophin mutations that cause Duchenne muscular dystrophy," Nature Communications, 2015, 6:6244.

(56) References Cited

OTHER PUBLICATIONS

Ousterout et al., "Reading frame correction by targeted genome editing restores dystrophin expression in cells from Duchenne muscular dystrophy patients," Mol Ther, 2013, 21:1718-1726.
Palu et al., "In pursuit of new developments for gene therapy of human diseases," J. Biotechnol. vol. 68, pp. 113, 1999.
Papayannakos, C. et al., "Understanding lentiviral vector chromatin targeting: working to reduce insertional mutagenic potential for gene therapy," Gene Ther, 2013, 20(6): p. 581-8.
Park et al., "Multi-Parametric MRI at 14T for Muscular Dystrophy Mice Treated with AAV Vector-Mediated Gene Therapy," PLoS One, 2015, 10(4): e0124914.
Park, K.S. et al., "Phenotypic alteration of eukaryotic cells using randomized libraries of artificial transcription factors," Nat Biotechnol 21, 2003, 1208-1214.
Pattanayak, V. et al., "High-throughput profiling of off-target DNA cleavage reveals RNA-programmed Cas9 nuclease specificity," Nat Biotechnol, 2013, 31(9): p. 839-43.
Peault, B. et al., "Stem and progenitor cells in skeletal muscle development, maintenance, and therapy," Molecular Therapy 15, 2007, 867-877.
Perez, E. et al., "Establishment of HIV-1 resistance in CD4+ T cells by genome editing using zinc-finger nucleases," Nature biotechnology 26, 2008, 808-816.
Perez-Pinera et al. Abstract 855. "Synergistic Transcriptional Activation by Combinations of Engineered TALEs" presented at the American Society of Gene & Cell Therapy's 15th Annual Meeting in Philadelphia, Pennsylvania, May 19, 2012.
Perez-Pinera et al., "Synergistic and tunable human gene activation by combinations of synthetic transcription factors," Nature Methods, vol. 10, No. 3, pp. 239-244, Feb. 3, 2013, including pp. 1/12-12-12 of Supplementary Material.
Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activation by CRISPR-Cas9-based transcription factors," Nat Methods, 2013, 10:973-976.
Perez-Pinera, P. et al., "Advances in targeted genome editing," Current Opinion in Chemical Biology 16, 2012, 268-277.
Perez-Pinera, P. et al., "Synergistic and tunable human gene activation by combinations of synthetic transcription factors," Nat Methods 10, 2013, 239-242.
Persons, D. A., "Lentiviral vector gene therapy: effective and safe?" Mol Ther, 2010, 18(5): p. 861-2.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pichavant, C. et al., "Current status of pharmaceutical and genetic therapeutic approaches to treat DMD," Molecular Therapy 19, 2011, 830-840.
Polstein, L. R. and Gersbach, C. A., "Light-inducible spatiotemporal control of gene activation by customizable zinc finger transcription factors," J Am Chem Soc, 2012, 134(40): p. 16480-3.
Popplewell, L. et al., "Gene correction of a duchenne muscular dystrophy mutation by meganuclease-enhanced exon knock-in," Hum Gene Ther, 2013, 24:692-701.
Qi, L.S. et al., "Repurposing CRISPR as an RNA-guided platform for sequence-specific control of gene expression," Cell 152, 2013, 1173-1183.
Ran et al., "Invivo genome editing using *Staphylococcus aureus* Cas9," Nature 520, 2015, 186-191.
Ran, F. A. et al., "Double nicking by RNA-guided CRISPR Cas9 for enhanced genome editing specificity," Cell, 2013, 154(6): p. 1380-9.
Rebar, E.J. et al., "Induction of angiogenesis in a mouse model using engineered transcription factors," Nat Med 8, 2002, 1427-1432.
Reyon, D. et al., "FLASH assembly of TALENs for high-throughput genome editing," Nat Biotechnol 30, 2012, 460-465.

Rousseau, J. et al., "Endonucleases: tools to correct the dystrophin gene" The Journal of Gene Medicine, 2011, vol. 13, pp. 522-537.
Saito et al., "Specific activation of microRNA-127 with downregulation of the proto-oncogene BCL6 by chromatin-modifying drugs in human cancer cells," Cancer Cell, 2006, vol. 9, pp. 435-443.
Salmon, P. and Trono, D., "Production and titration of lentiviral vectors," Curr Protoc Neurosci, 2006, Chapter 4: Unit 4 21.
Salva et al., "Design of tissue-specific regulatory cassettes for high-level rAAV-mediated expression in skeletal and cardiac muscle," Mol. Ther., 2007, 15:320-329.
Schmid-Burgk, J. L. et al., "A ligation-independent cloning technique for high-throughput of transcription activator-like effector genes," Nat Biotechnol 31, 2012, 76-81.
Scholze et al., "TAL effectors are remote controls for gene activation," Current Opinion in Microbiology, vol. 14, pp. 47-53, Jan. 2011.
Schultz, B. R. & Chamberlain, J. S., "Recombinant adeno-associated virus transduction and integration," Molecular Therapy 16, 2008, 1189-1199.
Sebastiano, V. et al., "In Situ Genetic Correction of the Sickle Cell Anemia Mutation in Human Induced Pluripotent Stem Cells Using Engineered Zinc Finger Nucleases," Stem Cells 29, 2011, 1717-1726.
Seidel et al., "Chromatin-modifying agents in anti-cancer therapy," Biochimie, 2012, vol. 94, pp. 2264-2279.
Seto et al., "Gene Replacement Therapies for Duchenne Muscular Dystrophy Using Adeno-Associated Viral Vectors," Current Gene Therapy, 2012, 12:139-151.
Sharma, S. et al., "Efficiency of nonhomologous DNA end joining varies among somatic tissues, despite similarity in mechanism," Cellular and Molecular Life Science 68, 2011, 661-676.
Shen et al., "Engraftment of a galactose receptor footprint onto adeno-associated viral capsids improves transduction efficiency," J. Biol. Chem., 2013, 288:28814-28823.
Silva, G. et al., "Meganucleases and other tools for targeted genome engineering: perspective and challenges for gene therapy," Current gene therapy, 2011, 11:11-27.
Şöllü, C. et al., "Autonomous zinc-finger nuclease pairs for targeted chromosomal deletion," Nucleic acids research 38, 2010, 8269-8276.
Song, L. et al., "Dnase-seq: a high-resolution technique for mapping active gene regulatory elements across the genome from mammalian cells," Cold Spring Harbor protocols 2010, pdb prot5384.
Song, L. et al., "Open chromatin defined by DNaseI and FAIRE identifies regulatory elements that shape cell-type identify," Genome Res 21, 2011, 1757-1767.
Sun, N. et al., "Optimized TAL effector nucleases (TALENs) for use in treatment of sickle cell disease," Molecular bioSystems 8, 2012, 1255-1263.
Szyf, M., "Epigenetics, DNA methylation, and chromatin modifying drugs," Annual Review of Pharmacology and Toxicology, 2009, vol. 49, pp. 243-263.
Tabebordbar et al., "In vivo gene editing in dystrophic mouse muscle and muscle stem cells," Science, 2015, 351(6271):407-411.
Taniguchi-Ikeda, M. et al., "Pathogenic exon-trapping by SVA retrotransposon and rescue in Fukuyama muscular dystrophy," Nature 478, 2011, 127-131.
Tebas, P. et al., "Gene editing of CCR5 in autologous CD4 T cells of persons infected with HIV," N Engl J Med, 2014, 370:901-910.
Tedesco, F. S. et al., "Repairing skeletal muscle: regenerative potential of skeletal muscle stem cells," J Clin Invest, 2010, 120:11-19.
Tedesco, F. S. et al., "Stem Cell-Mediated Transfer of a Human Artificial Chromosome Ameliorates Muscular Dystrophy," Science Translational Medicine 3, 96ra78-96ra78, 2011.
Tedesco, F. S. et al., "Transplantation of Genetically Corrected Human iPSC-Derived Progenitors in Mice with Lint-Girdle Muscular Dystrophy," Science Translational Medicine 4, 140ra189, 2012.
Tycko et al., "Screening *S. aureus* CRISPR-Cas9 Paired Guide RNAs for Efficient Targeted Deletion in Duchenne Muscular Dystrophy," Editas, Poster presented on May 5, 2016.

(56) References Cited

OTHER PUBLICATIONS

Urnov, F. et al., "Highly efficient endogenous human gene correction using designed zinc-finger nucleases," Nature 435, 2005, 646-651.

Van Pullen, M. et al., "Low dystrophin levels in heart can delay heart failure in mdx mice," J Mol Cell Cardiol, 2014, 69C:17-23.

Van Pullen, M. et al., "Low dystrophin levels increase survival and improve muscle pathology and function in dystrophin/utrophin double-knockout mice," FASEB J, 2013, 27:2484-2495.

Verma and Weitzman, "Gene Therapy: Twenty-first century medicine," Annual Review of Biochemistry, vol. 74, pp. 711-738, 2005.

Verma et al., "Gene therapy—promises, problems and prospects," Nature, vol. 389, pp. 239-242, 1997.

Vierbuchen, T. et al., "Direct conversion of fibroblasts to functional neurons by defined factors," Nature 463, 2010, 1035-1041.

Wang et al., "Adeno-associated virus vector carrying human minidystrophin genes effectively ameliorates muscular dystrophy in mdx mouse model," Proc Natl Acad Sci US A. (2000) 97(25):13714-13719.

Wang, H. et al., "One-Step Generation of Mice Carrying Mutations in Multiple Genes by CRISPR-Cas-Mediated Genome Engineering" Cell, 2013, 153(4): p. 910-8.

Wein, N. et al., "Efficient bypass of mutations in dysferlin deficient patient cells by antisense-induced exon skipping," Hum Mutat 31, 2010, 136-142.

Welch, E. M. et al., "PTC124 targets genetic disorders caused by nonsense mutations," Nature 447, 2007, 87-91.

Wienert et al., "Editing the genome to introduce a beneficial naturally occurring mutation associated with increased fetal globin," Nat Commun 6, 2015, 7085.

Yan et al., "Drugging the Undruggable: Transcription Therapy for Cancer," Biochimica et Biophysica Acta, vol. 1835, No. 1, pp. 76-85, Jan. 2013.

Yang, L., "Optimization of scarless human stem cell genome editing," Nucleic Acids Res, 2013, 41:9049-9061.

Yusa, K. et al., "Targeted gene correction of α1-antitrypsin deficiency in induced pluripotent stem cells," Nature 478, 2011, 391-394.

Zetsche et al., "Cpf1 is a Single RNA-Guided Endonuclease of a Class 2 CRISPR-Cas System," Cell, 2015, 163(3):759-71.

Zhang, F. et al. "Efficient construction of sequence-specific TAL effectors for modulating mammalian transcription," Nat Biotechnol 29, 2011, 149-153.

Zhu, C. H. et al., "Cellular senescence in human telomerase reverse transcriptase and cyclin-dependent kinase 4: consequences in aging muscle and therapeutic strategies for muscular dystrophies," Aging cell 6, 2007, 515-523.

Zou, J. et al., "Site-specific gene correction of a point mutation in human iPS cells derived from an adult patient with sickle cell disease," Blood 118, 2011, 4599-4608.

Invitation to Pay Additional Fees for Application No. PCT/US2017/042921 dated Sep. 22, 2017 (3 pages).

International Search Report and Written Opinion for Application No. PCT/US2017/042921 dated Nov. 9, 2017 (21 pages).

International Search Report and Written Opinion for Application No. PCT/US2016/064285 dated Apr. 6, 2017 (21 pages).

International Search Report and Written Opinion for Application No. PCT/US2017/031351 dated Nov. 21, 2017 (22 pages).

European Patent Office Extended Search Report for Application No. 17831820.0 dated Jul. 30, 2020 (15 pages).

Acosta et al., "Use of two gRNAs for CRISPR/Cas9 improves bi-allelic homologous recombination efficiency in mouse embryonic stem cells," Genesis, 2018, 56(5): 1-8.

Adamson et al., "A Multiplexed Single-Cell CRISPR Screening Platform Enables Systematic Dissection of the Unfolded Protein Response," Cell, 2016, 167: 1867-1882 e1821.

Aguilar et al., "Transcriptional and Chromatin Dynamics of Muscle Regeneration after Severe Trauma," Stem Cell Rep, 2016, 7: 983-997.

Ahlenius et al., "FoxO3 regulates neuronal reprogramming of cells from postnatal and aging mice," Proc Natl Acad Sci U S A, 2016, 113: 8514-8519.

Albuquerque et al., "Mammalian nicotinic acetylcholine receptors: from structure to function," Physiol Rev, 2009, 89: 73-120.

Amoasii et al., "Gene editing restores dystrophin expression in a canine model of Duchenne muscular dystrophy," Science, 2018, 362: 86-91.

Amoasii et al., "Single-cut genome editing restores dystrophin expression in a new mouse model of muscular dystrophy," Sci Transl Med, Nov. 2017, 9(418): eaan8081.

Andersen et al., "Dual role of delta-like 1 homolog (DLK1) in skeletal muscle development and adult muscle regeneration," Development, 2013, 140: 3743-3753.

Arnett et al., "Adeno-associated viral vectors do not efficiently target muscle satellite cells," Molecular Therapy Methods & Clinical Development, 2014, 1:14038.

Asokan et al., "Reengineering a receptor footprint of adeno-associated virus enables selective and systemic gene transfer to muscle," Nat Biotechnol, 2010, 28: 79-82.

Balboa et al., "Conditionally Stabilized dCas9 Activator for Controlling Gene Expression in Human Cell Reprogramming and Differentiation," Stem Cell Rep, 2015, 5: 448-459.

Barberi et al., "Derivation of engraftable skeletal myoblasts from human embryonic stem cells," Nat Med, 2007, 13: 642-648.

Barr et al., "Predominant Expression of Alternative PAX3 and PAX7 Forms in Myogenic and Neural Tumor Cell Lines," Cancer Res, 1999, 59: 5443-5448.

Bengtsson et al., "Muscle-specific CRISPR/Cas9 dystrophin gene editing ameliorates pathophysiology in a mouse model for Duchenne muscular dystrophy," Nat Commun, 2017, 8: 1-10.

Bernstein et al., "An integrated encyclopedia of DNA elements in the human genome," Nature, 2012, 489: 57-74.

Black et al., "Targeted Epigenetic Remodeling of Endogenous Loci by CRISPR/Cas9-Based Transcriptional Activators Directly Converts Fibroblasts to Neuronal Cells," Cell Stem Cell, 2016, 19: 406-414.

Boldrin et al., "Donor satellite cell engraftment is significantly augmented when the host niche is preserved and endogenous satellite cells are incapacitated," Stem Cells, 2012, 30: 1971-1984.

Bolger et al., "Trimmomatic: a flexible trimmer for Illumina sequence data," Bioinformatics, 2014, 30: 2114-2120.

Boshart et al., "A very strong enhancer is located upstream of an immediate early gene of human cytomegalovirus," Cell, 1985, 41(2): 521-530.

Boyle et al., "High-resolution mapping and characterization of open chromatin across the genome," Cell, 2008, 132: 311-322.

Briguet et al., "Histological parameters for the quantitative assessment of muscular dystrophy in the mdx-mouse," Neuromuscul. Disord., 2004, 14: 675-682.

Brunger et al., "CRISPR/Cas9 Editing of Murine Induced Pluripotent Stem Cells for Engineering Inflammation-Resistant Tissues," Arthritis Rheumatol, 2017, 69: 1111-1121.

Brunger et al., "Genome Engineering of Stem Cells for Autonomously Regulated, Closed-Loop Delivery of Biologic Drugs," Stem Cell Reports, 2017, 8: 1202-1213.

Buenrostro et al., "Transposition of native chromatin for fast and sensitive epigenomic profiling of open chromatin, DNA-binding proteins and nucleosome position," Nat Methods, 2013, 10: 1213-1218.

Busskamp et al., "Rapid neurogenesis through transcriptional activation in human stem cells," Mol SystBiol, 2014, 10: 760.

Chakraborty et al., "A CRISPR/Cas9-based system for reprogramming cell lineage specification," Stem Cell Reports, 2014, 3: 940-947.

Chal et al., "Differentiation of pluripotent stem cells to muscle fiber to model Duchenne muscular dystrophy," Nat Biotechnol, 2015, 33: 962-969.

Chamberlain et al., "Progress toward Gene Therapy for Duchenne Muscular Dystrophy," Mol. Ther., 2017, 25: 1125-1131.

Chanda et al., "Generation of induced neuronal cells by the single reprogramming factor ASCL1," Stem Cell Reports, 2014, 3: 282-296.

(56) References Cited

OTHER PUBLICATIONS

Chavez et al., "Highly efficient Cas9-mediated transcriptional programming," Nat Methods, 2015, 12: 326-328.
Cheloufi et al., "The histone chaperone CAF-1 safeguards somatic cell identity," Nature, 2015, 528: 218-224.
Chen et al., "Dynamic imaging of genomic loci in living human cells by an optimized CRISPR/Cas systemm," Cell, 2013, 155: 1479-1491.
Chen et al., "Enrichr: interactive and collaborative HTML5 gene list enrichment analysis tool," BMC Bioinformatics, 2013, 14: 128.
Chen et al., "microRNA-1 and microRNA-206 regulate skeletal muscle satellite cell proliferation and differentiation by repressing Pax7," J Cell Biol, 2010, 190: 867-879.
Childers et al., "Gene therapy prolongs survival and restores function in murine and canine models of myotubular myopathy," Sci Transl Med, 2014, 6: 220ra210.
Chronis et al., "Cooperative Binding of Transcription Factors Orchestrates Reprogramming," Cell, 2017, 168: 442-459 e420.
Cooper et al., "Improved induction of immune tolerance to factor IX by hepatic AAV-8 gene transfer," Hum Gene Ther, 2009, 20: 767-776.
Cordier et al., "Muscle-specific promoters may be necessary for adeno-associated virus-mediated gene transfer in the treatment of muscular dystrophies," Hum. Gene Ther., 2001, 12: 205-215.
D'Alessio et al., "A Systematic Approach to Identify Candidate Transcription Factors that Control Cell Identity," Stem Cell Reports, 2015, 5: 763-775.
Daley et al., "CRISPhieRmix: a hierarchical mixture model for CRISPR pooled screens," Genome Biol, 2018, 19: 159.
Darabi et al., "Functional skeletal muscle regeneration from differentiating embryonic stem cells," Nat Med, 2008, 14: 134-143.
Darmanis et al., "A survey of human brain transcriptome diversity at the single cell level," Proc Natl Acad Sci USA, 2015, 112: 7285-7290.
Deconinck et al., "Utrophin-Dystrophin-Deficient Mice as a Model for Duchenne Muscular Dystrophy," Cell, 1997, 90(4): 717-727.
Dijkema et al., "Cloning and expression of the chromosomal immune interferon gene of the rat," EMBO J, 1985, 4(3): 761-767.
Dobin et al., "STAR: ultrafast universal RNA-seq aligner," Bioinformatics, 2013, 29: 15-21.
Du et al., "Genetic interaction mapping in mammalian cells using CRISPR interference," Nat Methods, 2017, 14: 577-580.
Duan et al., "Expanding AAV packaging capacity with transsplicing or overlapping vectors: a quantitative comparison," Molecular Therapy, 2001, 4: 383-391.
Duan, "Systemic AAV Micro-dystrophin Gene Therapy for Duchenne Muscular Dystrophy," Molecular Therapy, 2018, 26(10): 2337-2356.
Dumont et al., "Dystrophin expression in muscle stem cells regulates their polarity and asymmetric division," Nat Med, 2015, 21: 1455-1463.
Dumont et al., "Intrinsic and extrinsic mechanisms regulating satellite cell function," Development, 2015, 142: 1572-1581.
Dunbar et al., "Gene therapy comes of age," Science, 2018, 359: eaan4672.
Eguchi et al., "Reprogramming cell fate with a genome-scale library of artificial transcription factors," Proc Natl Acad Sci U S A, 2016, 113: E8257-E8266.
Ernsberger, "Role of neurotrophin signalling in the differentiation of neurons from dorsal root ganglia and sympathetic ganglia," Cell Tissue Res, 2009, 336: 349-384.
Erwin et al., "Synthetic transcription elongation factors license transcription across repressive chromatin," Science, 2017, 358: 1617-1622.
Fairclough et al., "Therapy for Duchenne muscular dystrophy: renewed optimism from genetic approaches," Nat. Rev. Genet., 2013, 14: 373-378.
FDA approval brings first gene therapy to the United States, <https://www.fda.gov/newsevents/newsroom/pressannouncements/ucm574058.htm> (Aug. 30, 2017).
FDA approves first drug for spinal muscular atrophy, <https://www.fda.gov/newsevents/newsroom/pressannouncements/ucm534611.htm> (Dec. 23, 2016).
FDA approves first-of-its kind targeted RNA-based therapy to treat a rare disease, <https://www.fda.gov/newsevents/newsroom/pressannouncements/ucm616518.htm> (Aug. 10, 2018).
FDA approves novel gene therapy to treat patients with a rare form of inherited vision loss, <https://www.fda.gov/newsevents/newsroom/pressannouncements/ucm589467.htm> (Dec. 18, 2017).
FDA grants accelerated approval to first drug for Duchenne muscular dystrophy, <https://www.fda.gov/newsevents/newsroom/pressannouncements/ucm521263.htm> (Sep. 19, 2016).
Flandin et al., "Lhx6 and Lhx8 coordinately induce neuronal expression of Shh that controls the generation of interneuron progenitors," Neuron, 2011, 70: 939-950.
Friedland et al., "*Staphyloccocus aureus* Cas9: An Alternative Cas9 for Genome Editing Applications," Molecular Therapy, 2015, 23(Suppl. 1):S224.
Gaj et al., "Structure-Guided Reprogramming of Serine Recombinase DNA Sequence Specificity," Proc Natl Acad Sci U S A, 2011, 108(2): 498-503.
Gao et al., "Complex transcriptional modulation with orthogonal and inducible dCas9 regulators," Nat Methods, 2016, 13: 1043-1049.
Gascon et al., "Direct Neuronal Reprogramming: Achievements, Hurdles, and New Roads to Success," Cell Stem Cell, 2017, 21: 18-34.
Gersbach et al., "Targeted plasmid integration into the human genome by an engineered zinc-finger recombinase," Nucleic Acids Res, 2011, 39: 7868-7878.
Gilbert et al., "Genome-Scale CRISPR-Mediated Control of Gene Repression and Activation," Cell, 2014, 159: 647-661.
Goldstein et al., "In Situ Modification of Tissue Stem and Progenitor Cell Genomes," Cell Reports, 2019, 27: 1254-1264.e7.
Gorman et al., "The Rous sarcoma virus long terminal repeat is a strong promoter when introduced into a variety of eukaryotic cells by DNA-mediated transfection," Proc. Natl. Acad. Sci. USA, 1982, 79(22): 6777-6781.
Gregorevic et al., "Systemic microdystrophin gene delivery improves skeletal muscle structure and function in old dystrophic mdx mice," Mol Ther, 2008, 16: 657-664.
Hakim et al., "Evaluation of Muscle Function of the Extensor Digitorum Longus Muscle Ex vivo and Tibialis Anterior Muscle In situ in Mice," J. Vis. Exp., 2013, 1-8.
Hall et al., "Prevention of Muscle Aging by Myofiber-Associated Satellite Cell Transplantation," Sci Transl Med, 2010, 2: 57ra83.
Hardy et al., "Comparative Study of Injury Models for Studying Muscle Regeneration in Mice," PLoS One, 2016, 11: e0147198.
Harper et al., "Modular flexibility of dystrophin: implications for gene therapy of Duchenne muscular dystrophy," Nat. Med., 2002, 8: 253-261.
Harrow et al., "GENCODE: The reference human genome annotation for The ENCODE Project," Genome Res, 2012, 22: 1760-1774.
Heagerty et al., "Time-dependent ROC curves for censored survival data and a diagnostic marker," Biometrics, 2000, 56: 337-344.
Hilton et al., "Epigenome editing by a CRISPR-Cas9-based acetyltransferase activates genes from promoters and enhancers," Nat Biotechnol, 2015, 33: 510-517.
Himeda et al., "Design and Testing of Regulatory Cassettes for Optimal Activity in Skeletal and Cardiac Muscles," Methods Mol Biol, 2011, 709: 3-19 (Published Online Dec. 2010).
Horlbeck et al., "Compact and highly active next-generation libraries for CRISPR-mediated gene repression and activation," eLife, 2016, 5: e19760.
Huang et al., "Impaired respiratory function in mdx and mdx/utrn+/− mice," Muscle & Nerve, 2011, 43(2): 263-267.
Inoue et al., "Runx transcription factors in neuronal development," Neural Dev, 2008, 3: 20.
Isaac et al., "Dystrophin and utrophin "double knockout" dystrophic mice exhibit a spectrum of degenerative musculoskeletal abnormalities," Journal of Orthopaedic Research, 2013, 31(3): 343-349.

(56) References Cited

OTHER PUBLICATIONS

Jiang et al., "Notch signaling deficiency underlies age-dependent depletion of satellite cells in muscular dystrophy," Disease Models & Mechanisms, 2014, 7: 997-1004.

Jiwlawat et al., "Current Progress and Challenges for Skeletal Muscle Differentiation from Human Pluripotent Stem Cells Using Transgene-Free Approaches," Stem Cells Int, Apr. 2018, Article ID 6241681, 18 pages.

Jooss et al., "Transduction of dendritic cells by DNA viral vectors directs the immune response to transgene products in muscle fibers," J. Virol., 1998, 72: 4212-4223.

Kabadi et al., "Multiplex CRISPR/Cas9-based genome engineering from a single lentiviral vector," Nucleic Acids Res, 2014, 42: e147.

Keefe et al., "Muscle stem cells contribute to myofibers in sedentary adult mice," Nat Commun, 2015, 6: 7087.

Keil et al., "Brain transcriptome databases: a user's guide," J Neurosci, 2018, 38(10): 2399-2412.

Khambata-Ford et al., "Identification of Promoter Regions in the Human Genome by Using a Retroviral Plasmid Library-Based Functional Reporter Gene Assay," Genome Research, 2003, 13: 1765-1774.

Kim et al., "Expansion and Purification are Critical for the Therapeutic Application of Pluripotent Stem Cell-Derived Myogenic Progenitors," Stem Cell Rep, 2017, 9: 12-22.

Kim et al., "Use of the human elongation factor 1α promoter as a versatile and efficient expression system," Gene, 1990, 91(2): 217-223.

Klann et al., "CRISPR-based methods for high-throughput annotation of regulatory DNA," Curr Opin Biotechnol, 2018, 52: 32-41.

Klann et al., "CRISPR-Cas9 epigenome editing enables high-throughput screening for functional regulatory elements in the human genome," Nat Biotechnol, 2017, 35: 561-568.

Kodaka et al., "Skeletal Muscle Cell Induction from Pluripotent Stem Cells," Stem Cells Int, Apr. 2017, Article ID 1376151, 16 pages.

Koerber et al., "DNA shuffling of adeno-associated virus yields functionally diverse viral progeny," Mol Ther, 2008, 16: 1703-1709.

Konermann et al., "Genome-scale transcriptional activation by an engineered CRISPR-Cas9 complex," Nature, 2015, 517: 583-588.

Koopmans et al., "SynGO: An Evidence-Based, Expert-Curated Knowledge Base for the Synapse," Neuron, 2019, 103: 217-234 e214.

Koppanati et al., "Improvement of the mdx mouse dystrophic phenotype by systemic in utero AAV8 delivery of a minidystrophin gene," Gene Ther, 2010, 17: 1355-1362.

Kreis et al., "The Multifaceted p21 (Cip1/Waf1/CDKN1A) in Cell Differentiation, Migration and Cancer Therapy," Cancers (Basel), 2019, 11(9): 1220.

Kwon et al., "Myogenic Progenitor Cell Lineage Specification by CRISPR/Cas9-Based Transcriptional Activators," Stem cell reports, 2020, 14: 755-769.

Lake et al., "Integrative single-cell analysis of transcriptional and epigenetic states in the human adult brain," Nat Biotechnol, 2018, 36: 70-80.

Lam et al., "Rapid and Efficient Differentiation of Human Pluripotent Stem Cells into Intermediate Mesoderm That Forms Tubules Expressing Kidney Proximal Tubular Markers," J Am Soc Nephrol JASN, 2014, 25: 1211-1225.

Lambert et al., "The Human Transcription Factors," Cell, 2018, 172: 650-665.

Lamey et al., "Pax genes in myogenesis: alternate transcripts add complexity," Histol Histopathol, 2004, 19: 1289-1300.

Langmead et al., "Fast gapped-read alignment with Bowtie 2," Nat Methods, 2012, 9: 357-359.

Lee et al., "Activation of innate immunity is required for efficient nuclear reprogramming," Cell, 2012, 151: 547-558.

Lee et al., "Nanoparticle delivery of Cas9 ribonucleoprotein and donor DNA in vivo induces homology-directed DNA repair," Nat Biomed Eng, 2017, 1: 889-901.

Li et al., "Engineering and selection of shuffled AAV genomes: a new strategy for producing targeted biological nanoparticles," Mol Ther, 2008, 16: 1252-1260.

Li et al., "Precise correction of the dystrophin gene in duchenne muscular dystrophy patient induced pluripotent stem cells by TALEN and CRISPR-Cas9," Stem Cell Reports, 2015, 4: 143-154.

Li et al., "Preservation of muscle force in Mdx3cv mice correlates with low-level expression of a near full-length dystrophin protein," Am. J. Pathol., 2008, 172: 1332-1341.

Li et al., "RSEM: accurate transcript quantification from RNA-Seq data with or without a reference genome," BMC Bioinformatics, 2011, 12: 323.

Li et al., "Synthetic muscle promoters: activities exceeding naturally occurring regulatory sequences," Nature Biotechnology, 1999, 17: 241-245.

Lian et al., "Robust cardiomyocyte differentiation from human pluripotent stem cells via temporal modulation of canonical Wnt signaling," Proc Natl Acad Sci, 2012, 109: E1848-E1857.

Liao et al., "The Subread aligner: fast, accurate and scalable read mapping by seed-and-vote," Nucleic Acids Res, 2013, 41: e108.

Lim et al., "Application of CRISPR/Cas9 for the Treatment of Duchenne Muscular Dystrophy," Journal of Personalized Medicine, 2018, 8(4): 1-20.

Limberis et al., "Transduction efficiencies of novel AAV vectors in mouse airway epithelium in vivo and human ciliated airway epithelium in vitro," Molecular therapy: the journal of the American Society of Gene Therapy, 2009, 17: 294-301.

Liu et al., "Adeno-associated virus-mediated microdystrophin expression protects young mdx muscle from contraction-induced injury," Mol. Ther., 2005, 11: 245-256.

Liu et al., "CRISPR Activation Screens Systematically Identify Factors that Drive Neuronal Fate and Reprogramming," Cell Stem Cell, 2018, 23: 758-771 e758.

Liu et al., "CRISPR-Based Chromatin Remodeling of the Endogenous Oct4 or Sox2 Locus Enables Reprogramming to Pluripotency," Cell Stem Cell, 2018, 22: 252-261 e254.

Love et al., "Moderated estimation of fold change and dispersion for RNA-seq data with DESeq2," Genome Biol, 2014, 15: 550.

Madigan et al., "Engineering AAV receptor footprints for gene therapy," Curr Opin Virol, 2016, 18: 89-96.

Madisen et al., "A robust and high-throughput Cre reporting and characterization system for the whole mouse brain," Nat Neurosci, 2010, 13: 133-140.

Maeder et al., "CRISPR RNA-guided activation of endogenous human genes," Nat Methods, 2013, 10: 977-979.

Magli et al., "PAX7 Targets, CD54, Integrin α9β1, and SDC2, Allow Isolation of Human ESC/iPSC-Derived Myogenic Progenitors," Cell Rep, 2017, 19: 2867-2877.

Maheshri et al., "Directed evolution of adeno-associated virus yields enhanced gene delivery vectors," Nat Biotechnol, 2006, 24: 198-204.

Maniatis et al., "Regulation of inducible and tissue-specific gene expression," Science, 1987, 236(4806): 1237-1245.

Mann et al., "Improved antisense oligonucleotide induced exon skipping in the mdx mouse model of muscular dystrophy," J. Gene Med., 2002, 4: 644-654.

Manning et al., "What has the mdx mouse model of duchenne muscular dystrophy contributed to our understanding of this disease?," Journal of Muscle Research and Cell Motility, 2015, 36: 155-167.

Maruyama et al., "Epigenetic Regulation of Cell Type-Specific Expression Patterns in the Human Mammary Epithelium," PLoS Genetics, 2011, 7(4): e1001369, 15 pages.

McFadden et al., "The Hand1 and Hand2 transcription factors regulate expansion of the embryonic cardiac ventricles in a gene dosage-dependent manner," Development, 2005, 132: 189-201.

McGreevy et al., "Animal models of Duchenne muscular dystrophy: from basic mechanisms to gene therapy," Disease Models Mechanisms, 2015, 8(3): 195-213.

Mertens et al., "Evaluating cell reprogramming, differentiation and conversion technologies in neuroscience," Nat Rev Neurosci, 2016, 17: 424-437.

Miller et al., "Transcriptional landscape of the prenatal human brain," Nature, 2014, 508: 199-206.

(56) References Cited

OTHER PUBLICATIONS

Mizushima et al., "pEF-BOS, a powerful mammalian expression vector," Nuc. Acids. Res., 1990, 18(17): 5322.
Montalbano et al., "High-Throughput Approaches to Pinpoint Function within the Noncoding Genome," Molecular Cell, 2017, 68: 44-59.
Montarras, "Direct Isolation of Satellite Cells for Skeletal Muscle Regeneration," Science, 2005, 309: 2064-2067.
Morris et al., "Dissecting engineered cell types and enhancing cell fate conversion via CellNet," Cell, 2014, 158: 889-902.
Najm et al., "Orthologous CRISPR-Cas9 enzymes for combinatorial genetic screens," Nat Biotechnol, 2018, 36: 179-189.
Naldini, "Gene therapy returns to centre stage," Nature, 2015, 526: 351-360.
Nance et al., "AAV9 Edits Muscle Stem Cells in Normal and Dystrophic Adult Mice," Molecular Therapy, 2019, 27: 1568-1585.
Nelson et al., "Engineering Delivery Vehicles for Genome Editing," Annual review of chemical and biomolecular engineering, 2016, 7: 637-662.
Nelson et al., "Genome engineering: a new approach to gene therapy for neuromuscular disorders," Nat Rev Neurol, 2017, 13: 647-661.
Nelson et al., "Long-term evaluation of AAV-CRISPR genome editing for Duchenne muscular dystrophy," Nature Medicine, 2019, 25(3): 427-432.
Odom et al., "Microutrophin Delivery Through rAAV6 Increases Lifespan and Improves Muscle Function in Dystrophic Dystrophin/Utrophin-deficient Mice," Molecular Therapy, 2008, 16(9): 1539-1545.
O'Geen et al., "Ezh2-dCas9 and KRAB-dCas9 enable engineering of epigenetic memory in a context-dependent manner," Epigenetics Chromatin, 2019, 12: 26.
Olguin et al., "Pax-7 up-regulation inhibits myogenesis and cell cycle progression in satellite cells: a potential mechanism for self-renewal," Dev Biol, 2004, 275: 375-388.
Pang et al., "Induction of human neuronal cells by defined transcription factors," Nature, 2011, 476: 220-223.
Papapetrou, "Induced pluripotent stem cells, past and future," Science, 2016, 353: 991-992.
Parekh et al., "Mapping Cellular Reprogramming via Pooled Overexpression Screens with Paired Fitness and Single-Cell RNA-Sequencing Readout," Cell Systems, 2018, 7: 548-555.e548.
Pawlikowski et al., "Regulation of skeletal muscle stem cells by fibroblast growth factors," Dev Dyn, 2017, 246: 359-367.
Pigozzo et al., "Revertant Fibers in the mdx Murine Model of Duchenne Muscular Dystrophy: An Age- and Muscle-Related Reappraisal," PLoS One, 2013, 8(8): e72147.
Polstein et al., "A light-inducible CRISPR-Cas9 system for control of endogenous gene activation," Nature Chemical Biology, 2015, 11: 198-200.
Polstein et al., "Genome-wide specificity of DNA-binding, gene regulation, and chromatin remodeling by TALE- and CRISPR/Cas9-based transcriptional activators," Genome Res, 2015, 25: 1158-1169.
Rackham et al., "A predictive computational framework for direct reprogramming between human cell types," Nature Genetics, 2016, 48: 331-335.
Ramachandran et al., "Nitric Oxide Signaling Pathway in Duchenne Muscular Dystrophy Mice: Upregulation of L-arginine Transport," Biochem. J., 2012, 449: 133-142.
Rao et al., "Engineering human pluripotent stem cells into a functional skeletal muscle tissue," Nat Commun, 2018, 9: 126.
Roadmap Epigenomics Consortium, "Integrative analysis of 111 reference human epigenomes," Nature, 2015, 518:317-330.
Roudaut et al., "Restriction of calpain3 expression to the skeletal muscle prevents cardiac toxicity and corrects pathology in a murine model of limb-girdle muscular dystrophy," Circulation, 2013, 128: 1094-1104.
Sacco et al., "Short Telomeres and Stem Cell Exhaustion Model Duchenne Muscular Dystrophy in mdx/mTR Mice," Cell, 2010, 143: 1059-1071.
Sagal et al., "Proneural transcription factor Atoh1 drives highly efficient differentiation of human pluripotent stem cells into dopaminergic neurons," Stem Cells Transl Med, 2014, 3: 888-898.
Salmon et al., "Production and titration of lentiviral vectors," Curr Protoc Hum Genet, 2007, Chapter 12, Unit 12.10, Supplement 54, 24 pages.
Sambasivan et al., "Embryonic founders of adult muscle stem cells are primed by the determination gene Mrf4," Developmental Biology, 2013, 381: 241-255.
Sanson et al., "Optimized libraries for CRISPR-Cas9 genetic screens with multiple modalities," Nat Commun, 2018, 9: 5416.
Sharma et al., "In vivo genome editing of the albumin locus as a platform for protein replacement therapy," Blood, 2015, 126: 1777-1784.
Shelton et al., "Derivation and Expansion of PAX7-Positive Muscle Progenitors from Human and Mouse Embryonic Stem Cells," Stem Cell Rep, 2014, 3: 516-529.
Shen et al., "Combinatorial CRISPR-Cas9 screens for de novo mapping of genetic interactions," Nat Methods, 2017, 14: 573-576.
Shin et al., "Microdystrophin Ameliorates Muscular Dystrophy in the Canine Model of Duchenne Muscular Dystrophy," Mol. Ther., 2013, 21: 750-757.
Skene et al., "Genetic identification of brain cell types underlying schizophrenia," Nat Genet, 2018, 50: 825-833.
Song et al., "Non-immunogenic utrophin gene therapy for the treatment of muscular dystrophy animal models," Nature Medicine, 2019, 25(10): 1505-1511.
Stuelsatz et al., "A Contemporary Atlas of the Mouse Diaphragm: Myogenicity, Vascularity, and the Pax3 Connection" J Histochem Cytochem, 2012, 60(9): 638-657.
Suzuki et al., "In vivo genome editing via CRISPR/Cas9 mediated homology-independent targeted integration," Nature, 2016, 540: 144-149.
'T Hoen et al., "Generation and characterization of transgenic mice with the full-length human DMD gene," J. Biol. Chem., 2008, 283: 5899-5907.
Takahashi et al., "A decade of transcription factor-mediated reprogramming to pluripotency," Nature Reviews, 2016, 17: 183-193.
Takahashi et al., "Induction of pluripotent stem cells from mouse embryonic and adult fibroblast cultures by defined factors," Cell, 2006, 126: 663-676.
Takeshima et al., "Mutation spectrum of the dystrophin gene in 442 Duchene/Becker muscular dystrophy cases from one Japanese referral center," Journal of Human Genetics, 2010, 55: 379-388.
Tan et al., "Efficient derivation of lateral plate and paraxial mesoderm subtypes from human embryonic stem cells through GSKi-mediated differentiation," Stem Cells Dev, 2013, 22: 1893-1906.
Teratani-Ota et al., "Induction of specific neuron types by overexpression of single transcription factors," In Vitro Cell Dev Biol Anim, 2016, 52(9): 961-973.
Thakore et al., "Editing the epigenome: technologies for programmable transcription and epigenetic modulation," Nat Methods, 2016, 13: 127-137.
Thakore et al., "Highly specific epigenome editing by CRISPR-Cas9 repressors for silencing of distal regulatory elements," Nat Methods, 2015, 12: 1143-1149.
Thakore et al., "RNA-guided transcriptional silencing in vivo with S. aureus CRISPR-Cas9 repressors," Nat Commun, 2018, 9: 1674.
Theodorou et al., "A high throughput embryonic stem cell screen identifies Oct-2 as a bifunctional regulator of neuronal differentiation," Genes Dev, 2009, 23: 575-588.
Thorgeirsson et al., "A variant associated with nicotine dependence, lung cancer and peripheral arterial disease," Nature, 2008, 452: 638-642.
Tian et al., "CRISPR Interference-Based Platform for Multimodal Genetic Screens in Human iPSC-Derived Neurons," Neuron, 2019, 104: 239-255 e212.
Tinsley et al., "Amelioration of the dystrophic phenotype of mdx mice using a truncated utrophin transgene," Nature, 1996, 384(6607): 349-353.

(56) References Cited

OTHER PUBLICATIONS

Tsunemoto et al., "Diverse reprogramming codes for neuronal identity," Nature, 2018, 557: 375-380.
Uetsuki et al., "Isolation and Characterization of the Human Chromosomal Gene for Polypeptide Chain Elongation Factor-1α," J. Biol. Chem., 1989, 264(10): 5791-5798.
Van Arensbergen et al., "Genome-wide mapping autonomous promoter activity in human cells," Nature Biotechnology, 2017, 35(2): 145-153.
Van Deutekom et al., "Advances in Duchenne muscular dystrophy gene therapy," Nat. Rev. Genet., 2003, 4: 774-783.
Vaquerizas et al., "A census of human transcription factors: function, expression and evolution," Nat Rev Genet, 2009, 10: 252-263.
Verkhusha et al., "GFP-like flourescent proteins and chromoproteins of the class Anthozoa," Protein Structures: Kaleidoscope of Structural Properties and Functions, 2003, 405-439.
Vierbuchen et al., "Direct lineage conversions: unnatural but useful?," Nat Biotechnol, 2011, 29: 892-907.
Vierbuchen et al., "Molecular roadblocks for cellular reprogramming," Mol Cell, 2012, 47: 827-838.
Vorobyov et al., "Expression of two protein isoforms of PAX7 is controlled by competing cleavage-polyadenylation and splicing," Gene, 2004, 342: 107-112.
Voss et al., "The role of enhancers in the regulation of cell-type-specific transcriptional control," Trends Biochem. Sci., 1986, 11(7): 287-289.
Waddell et al., "Dlk1 is Necessary for Proper Skeletal Muscle Development and Regeneration," PLoS ONE, 2010, 5(11): e15055.
Waldrop et al., "Update in Duchenne and Becker muscular dystrophy," Current Opinion in Neurology, 2019, 32: 722-727.
Wang et al., "Adeno-associated virus serotype 8 efficiently delivers genes to muscle and heart," Nat. Biotechnol., 2005, 23: 321-328.
Wang et al., "Construction and analysis of compact muscle-specific promoters for AAV vectors," Gene Ther, 2008, 15: 1489-1499.
Wang et al., "Systemic human minidystrophin gene transfer improves functions and life span of dystrophin and dystrophin/utrophin-deficient mice," J. Orthop. Res., 2009, 27: 421-426.
Wapinski et al., "Hierarchical mechanisms for direct reprogramming of fibroblasts to neurons," Cell, 2013, 155: 621-635.
Weltner et al., "Human pluripotent reprogramming with CRISPR activators," Nat Commun Lond, 2018, 9: 1-12.
Westendorp et al., "E2F7 represses a network of oscillating cell cycle genes to control S-phase progression," Nucleic Acids Res, 2012, 40: 3511-3523.
Willmann et al., "Mammalian animal models for Duchenne muscular dystrophy," Neuromuscular Disorders, 2009, 19(4): 241-249.
Wu et al., "A Myogenic Double-Reporter Human Pluripotent Stem Cell Line Allows Prospective Isolation of Skeletal Muscle Progenitors," Cell Rep, 2018, 25: 1966-1981 ,e4.
Wüst et al., "Metabolic Maturation during Muscle Stem Cell Differentiation is Achieved by miR-1/133a-Mediated Inhibition of the Dlk1-Dio3 Mega Gene Cluster," Cell Metab, 2018, 27: 1026-1039.e6.
Wylie et al., "Distinct transcriptomes define rostral and caudal serotonin neurons," J Neurosci, 2010, 30: 670-684.
Xu et al., "Direct lineage reprogramming: strategies, mechanisms, and applications," Cell Stem Cell, 2015, 16: 119-134.
Xu et al., "Human Satellite Cell Transplantation and Regeneration from Diverse Skeletal Muscles," Stem Cell Rep, 2015, 5: 419-434.
Xu et al., "Recent advances in neuroepigenetic editing," Curr Opin Neurobiol, 2019, 59: 26-33.
Xue et al., "Synthetic mRNAs Drive Highly Efficient iPS Cell Differentiation to Dopaminergic Neurons," Stem Cells Transl Med, 2019, 8: 112-123.
Yang et al., "Generation of pure GABAergic neurons by transcription factor programming," Nat Methods, 2017, 14: 621-628.
Young et al., "A Single CRISPR-Cas9 Deletion Strategy that Targets the Majority of DMD Patients Restores Dystrophin Function in hiPSC-Derived Muscle Cells," Cell Stem Cell, 2016, 18: 533-540.

Young et al., "Creation of a Novel Humanized Dystrophic Mouse Model of Duchenne Muscular Dystrophy and Application of a CRISPR/Cas9 Gene Editing Therapy," Journal of Neuromuscular Diseases, 2017, 4(2): 139-145.
Zhang et al., "Comprehensive Structure-Function Study of Neurogenin3 Disease-Causing Alleles during Human Pancreas and Intestinal Organoid Development," Dev Cell, 2019, 50(3): 367-380.e7.
Zhang et al., "Rapid single-step induction of functional neurons from human pluripotent stem cells," Neuron, 2013, 78: 785-798.
Zhao et al., "The LIM-homeoboxgene Lhx8 is required for the development of many cholinergic neurons in the mouse forebrain," Proc Natl Acad Sci U S A, 2003, 100: 9005-9010.
Zhou et al., "Haploinsufficiency of utrophin gene worsens skeletal muscle inflammation and fibrosis in mdx mice," Journal of the Neurological Sciences, 2008, 264(1): 106-111.
Zincarelli et al., "Analysis of AAV serotypes 1-9 mediated gene expression and tropism in mice after systemic injection," Mol Ther, 2008, 16: 1073-1080.
International Search Report and Written Opinion for Application No. PCT/US2020/028154 dated Sep. 30, 2020 (17 pages).
International Search Report and Written Opinion for Application No. PCT/US2020/028148 dated Jul. 28, 2020 (13 pages).
International Search Report and Written Opinion for Application No. PCT/US2020/045544 dated Oct. 6, 2020 (16 pages).
International Search Report and Written Opinion for Application No. PCT/US2020/047083 dated Feb. 2, 2021 (17 pages).
International Search Report and Written Opinion for Application No. PCT/US2020/047080 dated Feb. 12, 2021 (14 pages).
International Search Report and Written Opinion for Application No. PCT/US2020/063150 dated Mar. 10, 2021 (11 pages).
Friedland et al., "Characterization of *Staphylococcus aureus* Cas9: a smaller Cas9 for all-in-one adeno-associated virus delivery and paired nickase applications," Genome Biology, 2015, 16(16):257, 10 pages.
Friedland et al., "*Staphyloccocus aureus* Cas9: An Alternative Cas9 for Genome Editing Applications," Retrieved from the Internet: <http://www.editasmedicine.com/data/doc uments/ASGCT%20poster 2015 Ari.pdf> Retrieved on Feb. 28, 2018.
Nelson et al., "Local and Systemic Gene Editing in a Mouse Model of Duchenne Muscular Dystrophy," Molecular Therapy, 2016, 24 (Supp 1):S191.
Xu et al., "CRISPR-mediated Genome Editing Restores Dystrophin Expression and Function in mdx Mice," Molecular Therapy: The Journal of the American Society of Gene Therapy, 2016, 24(3):564-569.
Kleinstiver et al., "Genome-wide specificities of CRISPR-Cas Cpf1 nucleases in human cells," Nature Biotechnology, 2016, 34(8):869-874.
European Patent Office Supplementary Search Report for Application No. 17831820.0 dated Feb. 28, 2020 (15 pages).
Hilton et al., "Enabling functional genomics with genome engineering," Genome Research, 2015, 25(10):1442-1455.
Riordan et al., "Application of CRISPR/Cas9 for biomedical discoveries," Cell & Bioscience, 2015, 5(1):11 pages.
Tsuchiya et al., "The "Spanning Protocol": A new DNA extraction method for efficient single-cell genetic diagnosis," Journal of Assisted Reproduction Genetics, 2005, 22(11-12):407-14.
Wood, "Neuromuscular disease: CRISPR/Cas9 gene-editing platform corrects mutations associated with Duchenne muscular dystrophy," Nature Reviews Neurology, 2015, 11(4):184.
Sequence alignment: Seq ID No. 102921 (2019).
Sequence alignment: Seq ID No. 103736 (2019).
Sequence alignment: Seq ID No. 103735 (2019).
Sequence alignment: Seq ID No. 102920 (2019).
Zhang et al., "Efficient precise knockin with a double cute HDR donor after CRISPR/Cas9-mediated double-stranded DNA cleavage," Genome Biol, 2017 18(35): 18 pages.
Guo et al., "Harnessing accurate non-homologous end joining for efficient prease deletion in CRISPR/Cas9-mediated genome editing," Genome Biology, 2018, 19: 170, 20 pages.
Koo et al., "Functional Rescue of Dystrophin Deficiency in Mice Caused by Frameshift Mutations Using Campylobacter jejuni Cas9," Molecular Therapy, 2018 26(6): 1529-1538.

(56) References Cited

OTHER PUBLICATIONS

Veltrop et al., "A dystrophic Duchenne mouse model fortesting human antisense oligonucleotides," PLoS One, 2018, 13(2): e0193289, 18 pages.
Japanese Patent Office Action for Application No. 2019-502579 dated Aug. 16, 2021 (6 pages, English translation included)>.
United States Patent Office Action for U.S. Appl. No. 15/779,633 dated Aug. 31, 2021 (8 pages).
International Search Report and Written Opinion for Application No. PCT/US2021/0029482 dated Sep. 1, 2021 (13 pages).
International Search Report and Written Opinion for Application No. PCT/US2021/029424 dated Sep. 17, 2021 (15 pages).
International Search Report and Written Opinion for Application No. PCT/US2021/029498 dated Sep. 17, 2021 (15 pages).
Xie et al., "sgRNAcas9: a software package for designing CRISPR sgRNA and evaluating potential off-target cleavage sites," PLoS One, 2014, 9(6): e100448.
United States Patent Office Action for U.S. Appl. No. 16/098,464 dated Jun. 21, 2021 (12 pages).
European Patent Office Action for Application No. 17831820.0 dated Jul. 14, 2021 (4 pages).
Anders et al., "Structural basis of PAM-dependent target DNA recognition by the Cas9 endonuclease," Nature, 2014, 513: 569-573.
Arnold et al., "Genome-wide quantitative enhancer activity maps identified by STARR-seq," Science, 2013, 339(6123): 1074-1077.
Asokan et al., "The AAV Vector Toolkit: Poised at the Clinical Crossroads," Mol Ther, 2012, 20: 699-708.
Ayyanathan et al., "Regulated recruitment of HPI to a euchromatic gene induces mitotically heritable, epigenetic gene silencing: a mammalian cell culture model of gene variegation," Genes Dev, 2003, 17: 1855-1869.
Bender et al., "Independent formation of Dnasel hypersensitive sites in the murine beta-globin locus control region," Blood, 2000, 95: 3600-3604.
Bernstein et al., "The NIH Roadmap Epigenomics Mapping Consortium," Nat Biotechnol, 2010, 28: 1045-1048.
Beverley, "Primer: making sense of T-cell memory," Nat. Clin Pract. Rheumatol., 2008, 4: 43-49.
Carrillo et al., "The Multiple Sequence Alignment Problem in Biology," SIAM J. Applied Math, 1988, 48: 1073.
Carter et al., "Long-range chromatin regulatory interactions in vivo," Nat Genet, 2002, 32: 623-626.
Chavez et al., "Comparison of Cas9 activators in multiple species," Nat Methods, 2016, 13: 563-67.
Chen et al., "Expanding the CRISPR imaging toolset with *Staphylococcus aureus* Cas9 for simultaneous imaging of multiple genomic loci," Nucleic Acids Research, 2016, 44(8): e75, 13 pages.
Chen et al., "Life and death of transcriptional co-activator p300," Epigenetics, 2011, 6: 957-961.
Chen et al., "Two upstream enhancers collaborate to regulate the spatial patterning and timing of MyoD transcription during mouse development," Dev Dyn, 2001, 221: 274-288.
Chew et al., "A multifunctional AAV-CRISPR-Cas9 and its host response," Nat Methods, 2016, 13: 868-74.
Choy et al., "Eukaryotic activators function during multiple steps of preinitiation complex assembly," Nature, 1993, 366: 531-536.
Chu et al., "SV40 DNA transfection of cells in suspension: analysis of efficiency of transcription and translation of T-antigen," Gene, 1981, 13:197.
Cong et al., "Comprehensive interrogation of natural TALE DNA-binding modules and transcriptional repressor domains," Nat Commun, 2012, 3: 968.
Consortium, "An integrated encyclopedia of DNA elements in the human genome," Nature, 2012, 489: 57-74.
Crawford et al., "Genome-wide mapping of DNase hypersensitive sites using massively parallel signature sequencing (MPSS)," Genome Res, 2006, 16: 123-131.
Crocker et al., "TALE-mediated modulation of transcriptional enhancers in vivo," Nature Methods, 2013, 10: 762-767.
De Groote et al., "Epigenetic Editing: targeted rewriting of epigenetic marks to modulate expression of selected target genes," Nucleic Acids Res, 2012, 40(21): 10596-10613.
Dean et al., "Inducible transcription of five globin genes in K562 human leukemia cells," Proceedings of the National Academy of Sciences of the United States of America, 1983, 80: 5515-5519.
Deltcheva et al., "Crispr RNA maturation by trans-encoded small RNA and host factor RNase III," Nature, 2011, 471(7340): 602-607.
Delvecchio et al., "Structure of the p300 catalytic core and implications for chromatin targeting and HAT regulation," Nat Struct Mol Biol 20, 2013, 1040-1046.
Deng et al., "Reactivation of developmentally silenced globin genes by forced chromatin looping," Cell, 2014, 158: 849-860.
Ding et al., "Permanent Alteration of PCSK9 Within Vivo CR1SPR-Cas9 Genome Editing," Circulation Research, 2014, 115(5): 488-492.
Doench et al., "Optimized sgRNA design to maximize activity and minimize off-target effects of CRISPR-Cas9," Nat Biotechnol, 2016, 34: 184-191.
Doench et al., "Rational design of highly active sgRNAs for CR1SPR-Cas9-mediated gene inactivation," Nat Biotechnol, 2014, 32: 1262-1267.
Dostie et al., "Chromosome Conformation Capture Carbon Copy (SC): a massively parallel solution for mapping interactions between genomic elements," Genome Research, 2006, 16: 1299-1309.
Doudna et al., "Genome editing. The new frontier of genome engineering with CRISPR-Cas9," Science, 2014, 346: 1258096.
EBI Accession No. GSP: BCJ39961 (2016).
Egger et al., "Epigenetics in human disease and prospects for epigenetic therapy," Nature, 2004, 429: 457-463.
Ferretti et al., "Complete genome sequence of an MI strain of *Streptococcus pyogenes*," Proc Natl Acad Sci US A, 2001, 98(8): 4658-63.
Fine et al., "Trans-spliced Cas9 allows cleavage of HBB and CCR5 genes in human cells using compact expression cassettes," Sci Rep. 2015, 5: 10777.
Fontenot et al., "Regulatory Tcell lineage specification by the forkhead transcription factor foxp3," Immunity, 2005, 22: 329-341.
Gao et al., "Comparison of TALE designer transcription factors and the CRISPR/dCas9 in regulation of gene expression by targeting enhancers," Nucleic Acids Res, 2014, 42: e155.
Gao et al., "Reprogramming to Pluripotency Using Designer TALE Transcription Factors Targeting Enhancers," Stem Cell Reports, 2013, 1(2): 183-197.
Garriga-Canut et al., "Synthetic zinc finger repressors reduce mutant huntingtin expression in the brain of R6/2 mice," Proceedings of the National Academy of Sciences of the United States of America, 2012, 109: E3136-E3145.
Gersbach et al., "Activating human genes with zinc finger proteins, transcription activator-like effectors and CRISPR/Cas9 for gene therapy and regenerative medicine," Expert Opin Ther Targets, 2014, 18(8): 835-839.
Gersbach, "Genome engineering: the next genomic revolution," Nat Methods, 2014, 11: 1009-1011.
Gerstein et al., "Architecture of the human regulatory network derived from ENCODE data," Nature, 2012, 489:91-100.
Graham et al., "A new technique for the assay of infectivity of human adenovirus 5 DNA," Virol., 1973, 52: 456-467.
Grimmer et al., "Analysis of an artificial zinc finger epigenetic modulator: widespread binding but limited regulation," Nucleic Acids Research, 2014, 42: 10856-10868.
Groner et al., "KRAB-zinc finger proteins and KAPI can mediate long-range transcriptional repression through heterochromatin spreading," PLoS Genet, 2010, 6: e1000869.
Hamar et al., "Small interfering RNA targeting Fas protects mice against renal ischemia-reperfusion injury," PNAS, 2004, 101: 14883-14888.
Hardison et al., "Locus control regions of mammalian beta-globin gene clusters: combining phylogenetic analyses and experimental results to gain functional insights," Gene, 1997, 205: 73-94.
Hathaway et al., "Dynamics and memory of heterochromatin in living cells," Cell, 2012, 149: 1447-1460.

(56) References Cited

OTHER PUBLICATIONS

Heintzman et al., "Distinct and predictive chromatin signatures of transcriptional promoters and enhancers in the human genome," Nat Genet, 2007, 39: 311-318.
Hotta et al., "Isolation of human iPS cells using EOS lentiviral vectors to select for pluripotency," Nat Methods, 2009, 6: 370-376.
Hsu et al., "Development and applications of CRISPR-Cas9 for genome engineering," Cell, 2014, 157: 1262-1278.
Hu et al., "Direct activation of human and mouse Oct4 genes using engineered TALE and Cas9 transcription factors," Nucleic Acids Res, 2014, 42: 4375-4390.
Ikonomi et al., "Levels of GATA-1/GATA-2 transcription factors modulate expression of embryonic and fetal hemoglobins," Gene, 2000, 261: 277-287.
Ji et al., "Engineered zinc-finger transcription factors activate OCT4 (POUSFI), SOX2, KLF4, c-MYC (MYC) and miR302/367," Nucleic Acids Res, 2014, 42: 6158-6167.
Jörg, "Engineering of the epigenome: synthetic biology to define functional causality and develop innovative therapies," Epigenomics, 2016, 8(2): 153-156.
Kearns et al., "Functional annotation of native enhancers with a Cas9-histone demethylase fusion," Nat Methods, 2015, 12(5): 401-403.
Keung et al., "Using targeted chromatin regulators to engineer combinatorial and spatial transcriptional regulation," Cell, 2014, 158: 110-120.
Khoury et al., "Efficient new cationic liposome formulation for systemic delivery of small interfering RNA silencing tumor necrosis factor a in experimental arthritis," Arthritis Rheumatol, 2006, 54: 1867-1877.
Kim et al., "A Histone acetylation contributes to chromatin looping between the locus control region and globin gene by influencing hypersensitive site formation," Biochim Biophys Acta, 2013, 1829: 963-969.
Kotin, "Prospects for the use of adeno-associated virus as a vector for human gene therapy," Hum Gene Ther, 1994, 5: 793-801.
Kuscu et al., "Genome-wide analysis reveals characteristics of off-target sites bound by the Cas9 endonuclease," Nat Biotechnol, 2014, 32(7): 677-683.
La Russa et al., "The New State of the Art: Cas9 for Gene Activation and Repression," Molecular and Cellular Biology, 2015, 35(22): 3800-3809.
Landen et al., "Intraperitoneal delivery of liposomal siRNA for therapy of advanced ovarian cancer," Cancer Biol. Ther., 2006, 5(12): 1708-1713.
Lee et al., "Role of satellite cells versus myofibers in muscle hypertrophy induced by inhibition of the myostatin/activin signaling pathway," Proc Natl Acad Sci US A, 2012, 109(35): E2353-E2360.
Lee, "Regulation of muscle mass by myostatin," Annu Rev Cell Dev Biol, 2004, 20: 61-86.
Li et al., "Extensive promoter-centered chromatin interactions provide a topological basis for transcription regulation," Cell, 2012, 148: 84-98.
Li et al., "Locus control regions," Blood, 2002, 100: 3077-3086.
Li et al., "The role of chromatin during transcription," Cell, 2007, 128: 707-719.
Li et al., "The Sequence Alignment/Map format and SAM tools," Bioinformatics, 2009, 25: 2078-2079.
Magnenat et al., "In vivo selection of combinatorial libraries and designed affinity maturation of polydactyl zinc finger transcription factors for ICAM-1 provides new insights into gene regulation," J Mol Biol, 2004, 341: 635-649.
Matsushita et al., "Adeno-associated virus vectors can be efficiently produced without helper virus," Gene Therapy, 1998, 5: 938.
McCarty et al., "Self-complementary recombinant adeno-associated virus (ScAAV) vectors promote efficient transduction independently of DNA synthesis," Gene Ther, 2001, 8: 1248-1254.
McDowell et al., "A Structural and functional cross-talk between a distant enhancer and the epsilon-globin gene promoter shows interdependence of the two elements in chromatin," Molecular and Cellular Biology, 1999, 19: 7600-7609.
Memedula et al., "Sequential recruitment of HAT and SWI/SNF components to condensed chromatin by VP16," Curr Biol, 2003, 13: 241-246.
Mittler et al., "A novel docking site on Mediator is critical for activation by VP 16 in mammalian cells," EMBO J, 2003, 22: 6494-6504.
Morrissey et al., "Activity of stabilized short interfering RNA in a mouse model of hepatitis B virus replication," Hepatol, 2005, 41: 1349-1356.
Muzycka, "Use of adeno-associated virus as a general transduction vector for mammalian cells," Curr. Top. Microbiol. Inmunol., 1992, 158: 97-129.
Nissim et al., "Multiplexed and Programmable Regulation of Gene Networks with an Integrated RNA and CRISPR/Cas Toolkit in Human Cells," Mol Cell, 2014, 54: 698-710.
Nordhoff et al., "Comparative analysis of human, bovine, and murine Oct-4 upstream promoter sequences," Mamm Genome, 2001, 12: 309-317.
Ogryzko et al., "The transcriptional coactivators p300 and CBP are histone acetyltransferases," Cell, 1996, 87: 953-959.
Okkenhaug et al., "PI3K in lymphocyte development, differentiation and activation," Nat. Rev. Immunol., 2003, 3(4): 317-330.
Ong et al., "Enhancer function: new insights into the regulation of tissue-specific gene expression," Nature reviews. Genetics, 2011, 12: 283-293.
Osakabe et al., "FLAG-NLS-SpCas9-2A-GFBSD2 [Binary vector pEgP526-2A-GFBSD2]," National Center for Biotechnology Information, Genbank Entry, Retrieved from the Internet on Sep. 18, 2017 <https://www .ncbi.nlmnih gov/protein/BAVO1234>.
Quinlan et al., "BEDTools: a flexible suite of utilities for comparing genomic features," Bioinformatics, 2010, 26: 841-842.
Rada-Iglesias et al., "A unique chromatin signature uncovers early developmental enhancers in humans," Nature, 2011, 470: 279-283.
Rahdar et al., "Synthetic CRISPR RNA-Cas9-Guided Genome Editing in Human Cells," Proceedings to the National Academy of Sciences of USA, 2015, 112(51): E7110-E7117.
Reynolds et al., "NuRD-mediated deacetylation of H3K27 facilitates recruitment of Polycomb Repressive Complex 2 to direct gene repression," The EMBO Journal, 2012, 31: 593-605.
Riley, "PD-1 signaling in primary T cells," Immunological Reviews, 2009, 229: 114-125.
Rivenbark et al., "Epigenetic reprogramming of cancer cells via targeted DNA methylation," Epigenetics, 2012, 7: 350-360.
Schultz et al., "SETDBI: a novel KAP-I-associated histone H3, lysine 9-specific methyltransferase that contributes to HPI-mediated silencing of euchromatic genes by KRAB zinc-finger proteins," Genes & Development, 2002, 16: 919-932.
Smith et al., "Myostatin inhibitors as therapies for muscle wasting associated with cancer and other disorders," Curr Opin Support Palliat Care, 2013, 7: 352-60.
Snowden et al., "Gene-specific targeting of H3K9 methylation is sufficient for initiating repression in vivo," Curr Biol, 2002, 12: 2159-2166.
Soutschek et al., "Therapeutic silencing of an endogenous gene by systemic administration of modified siRNAs," Nature, 2004, 432: 173-178.
Spitz et al., "Transcription factors: from enhancer binding to developmental control," Nat. Rev. Genet., 2012, 13: 613-626.
Sripathy et al., "The KAP1 corepressor functions to coordinate the assembly of de novo HP1-demarcated microenvironments of heterochromatin required for KRAB zinc finger protein-mediated transcriptional repression," Molecular and Cellular Biology, 2006, 26: 8623-8638.
Sternberg et al., "Conformational Control of DNA Target Cleavage by CR1SPR-Cas9," Nature, 2015, 527(7576): 110-113.
Sternberg et al., "DNA interrogation by the CRISPR RNA-guided endonuclease Cas9," Nature, 2014, 507: 62-67.
Su et al., "In vitro and in vivo mRNA delivery using lipid-enveloped pH-responsive polymer nanoparticles," Mol. Pharmaceutics, 2011, 8: 774-787.

(56) References Cited

OTHER PUBLICATIONS

Takahashi et al., "Induction of pluripotent stem cells from adult human fibroblasts by defined factors," Cell, 2007, 1131: 861-872.
Tanenbaum et al., "A Protein-Tagging System for Signal Amplification in Gene Expression and Fluorescence Imaging," Cell, 2014, 159(3): 635-646.
Thomson et al., "Human herpesvirus 6 (HHV-6) is a helper virus for adeno-associated virus type 2 (AAV-2) and the AAV-2 rep gene homologue in HHV-6 can mediate AAV-2 DNA replication and regulate gene expression," Virol., 1994, 204: 304-311.
Thurman et al., "The accessible chromatin landscape of the human genome," Nature, 2012, 489: 75-82.
Tone et al., "Smad3 and NFAT cooperate to induce Foxp3 expression through its enhancer," Nat. Immunol., 2008, 9: 194-202.
Truong et al., "Development of an intein-mediated split-Cas9 system for gene therapy," Nucleic Acids Res., 2015, 43: 6450-6458.
Tuan et al., "Transcription of the hypersensitive site HS2 enhancer in erythroid cells," Proceedings of the National Academy of Sciences of the United States of America, 1992, 89: 11219-11223.
Uchida et al., "In Vivo Messenger RNA Introduction into the Central Nervous System Using Polyplex Nanomicelle," PLoS ONE, 2013, 8: e56220.
Vakoc et al., "Proximity among distant regulatory elements at the beta-globin locus requires GATA-1 and FOG-1," Molecular Cell, 2005, 17: 453-462.
Visel et al., "ChIP-seq accurately predicts tissue-specific activity of enhancers," Nature, 2009, 457: 854-858.
Wagner et al., "A phase 1/11 trial of MYO-029 in adult subjects with muscular dystrophy," Ann Neurol, 2008, 63: 561-571.
Wang et al., "Efficient delivery of genome-editing proteins using bioreducible lipid nanoparticles," Proc Natl Acad Sci USA, 2016, 113(11): 2868-2873.
Wang et al., "Epstein-Barr virus nuclear protein 2 interacts with p300, CBP, and PCAF histone acetyltransferases inactivation of the LMP1 promoter," Proc Natl Acad Sci USA, 2000, 97: 430-435.
Wang et al., "Genome-wide mapping of HATs and HDACs reveals distinct functions inactive and inactive genes," Cell, 2009, 138: 1019-1031.
Whisstock et al., "Prediction of protein function from protein sequence," Q Rev Biophysics, 2003, 36(3): 307-340.
Wu et al., "Genome-wide binding of the CRISPR endonuclease Cas9 in mammalian cells," Nat Biotechnol, 2014, 32: 670-676.
Youngblood et al., "Chronic virus infection enforces demethylation of the locus that encodes PD-1 in antigen- specific cos+ T cells," Immunity, 2011, 35: 400-412.
Zhang et al., "Adenovirus-Adeno-Associated Virus Hybrid for Large-Scale Recombinant Adeno-Associated Virus Production," Hum Gene Ther, 2009, 20: 922-929.
Zhang et al., "Model-based analysis of ChIP-Seq (MACS)," Genome Biology, 2008, 9: R137.
Zheng et al., "Role of conserved non-coding DNA elements in the Foxp3 gene in regulatory T-cell fate," Nature, 2010, 463: 808-812.
Zhou et al., "High-throughput screening of a CRISPR/Cas9 library for functional genomics in human cells," Nature, 2014, 509(7501): 487-491.
Ousterout et al., "Genetic Correction of Duchenne Muscular Dystrophy Using Zinc Finger Nucleases," Mol. Ther., 2013, vol. 21, Supplement 1, 292, p. S111-S112.
Rousseau et al., "New TALENs To Correct the Reading Frame of Exon 54 of the Dystrophin Gene," Mol. Ther., 2013, vol. 21, Supplement 1, 293, p. S112.
United States Patent Office Action for U.S. Appl. No. 16/098,464 dated Nov. 15, 2021 (12 pages).
United States Patent Office Action for U.S. Appl. No. 15/779,633 dated Dec. 15, 2021 (13 pages).
Japanese Patent Office Action for Application No. 2019-502579 dated Mar. 2, 2022 (6 pages, English translation included).
International Search Report and Written Opinion for Application No. PCT/US2021/056122 dated Mar. 24, 2022 (16 pages).
European Patent Office Action for Application No. 17831820.0 dated May 20, 2022 (5 pages).
United States Patent Office Action for U.S. Appl. No. 15/779,633 dated Jun. 3, 2022 (15 pages).
Pykhozhij et al., "CRISPR MultiTargeter: A Web Tool to Find Common and Unique CRISPR Single Guide RNA Targets in a Set of Similar Sequences," PLoS One, 2015, 10(3): e011932.
U.S. Appl. No. 17/636,750, filed Feb. 18, 2022.
U.S. Appl. No. 17/636,754, filed Feb. 18, 2022.
U.S. Appl. No. 17/766,003, filed Apr. 1, 2022.
U.S. Appl. No. 63/314,183, filed Feb. 25, 2022.
U.S. Appl. No. 63/314,256, filed Feb. 25, 2022.
U.S. Appl. No. 63/317,847, filed Mar. 8, 2022.
U.S. Appl. No. 63/325,037, filed Mar. 29, 2022.
U.S. Appl. No. 63/325,039, filed Mar. 29, 2022.
U.S. Appl. No. 63/330,679, filed Apr. 13, 2022.
U.S. Appl. No. 63/372,373, filed Mar. 8, 2022.
PCT/US2022/018400, filed Mar. 1, 2022.
U.S. Appl. No. 63/330,691, filed Apr. 13, 2022.
U.S. Appl. No. 17/471,935, filed Sep. 10, 2021, 2022/0098561, Mar. 31, 2022.
U.S. Appl. No. 17/603,243, filed Oct. 12, 2021.
U.S. Appl. No. 17/603,329, filed Oct. 12, 2021.
U.S. Appl. No. 17/603,330, filed Oct. 12, 2021.
PCT/US2021/056122, filed Oct. 21, 2021.
PCT/US2021/054292, filed Oct. 8, 2021.
PCT/US2021/054636, filed Oct. 12, 2021.
PCT/US2021/059270, filed Nov. 12, 2021.
Adamson et al., "A Multiplexed Single-Cell CRISPR Screening Platform Enables Systematic Dissection of the Unfolded Protein Response," Cell, 2016, 167: 1867-1882.e21.
Aloia, "Epigenetic Regulation of Cell-Fate Changes That Determine Adult Liver Regeneration After Injury," Front. Cell Dev. Biol., 2021, 9: 643055.
Amabile et al., "Inheritable Silencing of Endogenous Genes by Hit-and-Run Targeted Epigenetic Editing, " Cell, 2016, 167(1): 219-232.e14.
Amabile et al., "Permanent Epigenetic Silencing of Human Genes With Artificial Transcriptional Repressors,", Molecular Therapy, 2015, 23(Suppl. 1): S275.
Arechavala-Gomeza et al., "Comparative analysis of antisense oligonucleotide sequences for targeted skipping of exon 51 during dystrophin pre-mRNA splicing in human muscle," Human Gene Therapy, 2007, 18: 798-810.
Asrani et al., "Burden of liver diseases in the world," J Hepatol, 2019, 70(1): 151-171.
Baratta et al., "Cellular organization of normal mouse liver: a histological, quantitative immunocytochemical, and fine structural analysis," Histochem Cell Biol, 2009, 131(6): 713-726.
Barrangou et al., "CRISPR provides acquired resistance against viruses in prokaryotes," Science, 2007, 315(5819): 1709-1712.
Bartel et al., "Isolation of new ribozymes from a large pool of random sequences," Science, 1993, 261(5127): 1411-1418.
Beaudry et al., "Directed evolution of an RNA enzyme," Science, 1992, 257(5070): 635-641.
Bieth et al., "Highly restricted deletion of the SNORD116 region is implicated in Prader-Willi Syndrome," Eur J Hum Genet, 2015, 23: 252-255.
Bittel et al., "Prader-Willi syndrome: clinical genetics, cytogenetics and molecular biology," Expert Rev Mol Med, 2005, 7(14): 1-20.
Blakemore et al., "Editing of Human Genes May Begin by Year's End in the U.S." Smithsonian.com, <https://www.smithsonianmag.com/smart-news/editing-human-genes-may-begin-years-end-us-180959532/?no-ist> 2016.
Blancafort et al., "Writing and rewriting the epigenetic code of cancer cells: from engineered proteins to small molecules," Mol. Pharmacol., 2013, 83(3): 563-576.
Braasch et al., "Novel Antisense and Peptide Nucleic Acid Strategies for Controlling Gene Expression," Biochemistry, 2002, 41: 4503-4510.
Breaker et al., "Inventing and improving ribozyme function rational design versus iterative selection methods," TIBTECH, 1994, 12: 268-274.

(56) References Cited

OTHER PUBLICATIONS

Breaker, "Are engineered proteins getting competition from RNA?," Curr. Op. Biotech., 1996, 7(4): 442-448.
Briner et al., "Guide RNA Functional Modules Direct Cas9 Activity and Orthogonality," Molecular Cell, 2014, 56(2): 333-339.
Briner et al., "Lactobacillus buchneri genotyping on the basis of clustered regularly interspaced short palindromic repeat (CRISPR) locus diversity," Appl. Environ. Microbiol., 2014, 80: 994-1001.
Brummelkamp et al., "A system for stable expression of short interfering RNAs in mammalian cells," Science, 2002, 296(5567): 550-553.
Buiting, "Prader-Willi syndrome and Angelman syndrome," Am J Med Genet C Semin Med Genet, 2010, 154C(3): 365-376.
Burnett et al., "Deficiency in prohormone convertase PC1 impairs prohormone processing in Prader-Willi syndrome," J Clin Invest, 2017, 127: 293-305.
Cano-Rodriguez et al., "Writing of H3K4Me3 overcomes epigenetic silencing in a sustained but context-dependent manner," Nat Commun, 2016, 7: 12284.
Carroll, "A CRISPR approach to gene targeting, " Molecular Therapy, 2012, 20: 1658-1660.
Cassidy et al., "Prader-Willi syndrome," Eur J Hum Genet, 2009, 17(1): 3-13.
Cassidy et al., "Prader-Willi syndrome," Genet Med, 2012, 14: 10-26.
Cencic et al., "Protospacer adjacent motif (PAM)-distal sequences engage CRISPR Cas9 DNA target cleavage," PLoS one, 2014, 9, e109213, 13 pages.
Chang et al., "Integrating Combinatorial Lipid Nanoparticle and Chemically Modified Protein for Intracellular Delivery and Genome Editing," Acc. Chem. Res., 2019, 52: 665-675.
Chen et al., "Acetylation of RelA at discrete sites regulates distinct nuclear functions of NF-KB," The EMBO Journal, 2002, 21(23): 6539-6548.
Chen et al., "Genome-wide CRISPR screen in a mouse model of tumor growth and metastasis," Cell, 2015, 160: 1246-1260.
Chen et al., "Targeted activation of diverse CRISPR-Cas systems for mammalian genome editing via proximal CRISPR targeting," Nature Communications, 2017, 8: 14958.
Chen et al., "Vitamin D receptor suppresses proliferation and metastasis in renal cell carcinoma cell lines via regulating the expression of the epithelial Ca2+ channel TRPV5," PLoS One, 2018, 13: e0195844.
Christoffersen et al., "Ribozymes as human therapeutic agents," J. Med. Chem., 1995, 38(12): 2023-2037.
Concise Encyclopedia of Polymer Science And Engineering, 1990, pp. 858-859.
Corces et al., "The chromatin accessibility landscape of primary human cancers," Science, 2018, 362(6413): eaav1898.
Crooke et al., "Pharmacokinetic properties of several novel oligonucleotide analogs in mice," J. Pharmacol. Exp. Ther., 1996, 277(2): 923-937.
Cruvinel et al., "Reactivation of maternal SNORD116 cluster via SETDB1 knockdown in Prader-Willi syndrome iPSCs," Hum Mol Genet, 2014, 23: 4674-4685.
Dahlman et al., "Orthogonal gene knockout and activation with a catalytically active Cas9 nuclease," Nat Biotechnol, 2015, 33(11): 1159-1161, correction in Nat Biotechnol, Apr. 2016, 34(4): 441.
Datlinger et al., "Pooled CRISPR screening with single-cell transcriptome readout, " Nat. Methods, 2017, 14: 297-301.
De Mesmaeker et al., "Antisense Oligonucleotides," Acc. Chem. Res., 1995, 28: 366-374.
de Smith et al., "A deletion of the HBII-85 class of small nucleolar RNAs (snoRNAs) is associated with hyperphagia, obesity and hypogonadism," Hum Mol Genet, 2009, 18: 3257- 3265.
Dempster et al., "Extracting Biological Insights from the Project Achilles Genome-Scale CRISPR Screens in Cancer Cell Lines," Cold Spring Harbor Laboratory, 2019, 35 pages.

Diao et al., "A new class of temporarily phenotypic enhancers identified by CRISPR/Cas9-mediated genetic screening," Genome Res, 2016, 26: 397-405.
Dirks et al., "Triggered amplification by hybridization chain reaction," Proceedings of the National Academy of Sciences of the United States of America, 2004, 101(43): 15275-15278.
Dixit et al., "Perturb-Seq: Dissecting Molecular Circuits with Scalable Single-Cell RNA Profiling of Pooled Genetic Screens," Cell, 2016, 167: 1853-1866.e17.
Duan et al., "Genome-wide identification of CRISPR/Cas9 off-targets in human genome," Cell research, 2014, 24(8): 1009-12.
Duker et al., "Paternally inherited microdeletion at 15q11.2 confirms a significant role for the SNORD116 C/D box snoRNA cluster in Prader-Willi syndrome," Eur J Hum Genet, 2010, 18: 1196-1201.
Dykeman, "An implementation of the Gillespie algorithm for RNA kinetics with logarithmic time update," Nucleic Acids Research, 2015, 45(12): 5708-5715.
Encode Project Consortium, "Expanded encyclopaedias of DNA elements in the human and mouse genomes," Nature, 2020, 583: 699-710.
Englisch et al., Chemically Modified Oligonucleotides as Probes and Inhibitors, Angewandle Chemie, International Edition, 1991, 30(6): 613-629.
Eraslan et al., "Deep learning: new computational modelling techniques for genomics," Nat. Rev. Genet., 2019, 20: 389-403.
Ernst et al., "ChromHMM: automating chromatin-state discovery and characterization," Nat. Methods, 2012, 9: 215-216.
Farasat et al., "A Biophysical Model of CRISPR/Cas9 Activity for Rational Design of Genome Editing and Gene Regulation," PLOS Computational Biology, 2016, 12(1):e1004724.
Farasat, "Sequence-to-Function Models for Efficient Optimization of Metabolic Pathways and Genetic Circuits," Ph. D. Thesis, 2015, 254 pages.
Flamm et al., "RNA folding at elementary step resolution," Rna, 2000, 6: 325-338.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 2009, 5: 838-843.
Frank et al., "HDAC inhibitors cause site-specific chromatin remodeling at PU. 1-bound enhancers in K562 cells," Epigenetics Chromatin, 2016, 9: 15.
Fu et al., "Landscape of target: guide homology effects on Cas9-mediated cleavage," Nucleic Acids Research, 2014, 42(22): 13778-13787.
Fulco et al., "Activity-by-contact model of enhancer-promoter regulation from thousands of CRISPR perturbations," Nature Genetics, 2019, 51: 1664-1669.
Fulco et al., "Systematic mapping of functional enhancer-promoter connections with CRISPR interference," Science, 2016, 354: 769-773.
Fulmer-Smentek et al., "Association of acetylated histones with paternally expressed genes in the Prader-Willi deletion region," Hum Mol Genet, 2001, 10: 645-652.
Gait, "Oligoribonucleotides," Antisense Research and Applications, 1993, Chapter 16, pp. 290-299.
Gasiunas et al., "Cas9-crRNA ribonucleoprotein complex mediates specific DNA cleavage for adaptive immunity in bacteria," Proc. Natl. Acad. Sci., 2012, 109: E2579-E2586.
Gasperini et al., "A Genome-wide Framework for Mapping Gene Regulation via Cellular Genetic Screens," Cell, 2018, 176(1-2); 377-390.e19.
Gaudelli et al., "Directed evolution of adenine base editors with increased activity and therapeutic application," Nat Biotechnol, Jul. 2020, 38(7): 892-900.
Gaudelli et al., "Programmable base editing of A•T to G•C in genomic DNA without DNA cleavage," Nature, Nov. 2017, 551(7681): 464-471.
Gebeyehu et al., "Novel biotinylated nucleotide—analogs for labeling and colorimetric detection of DNA," Nucl. Acids Res., 1987, 15(11): 4513-4534.

(56) References Cited

OTHER PUBLICATIONS

Gee et al., "Cellular Reprogramming Genome Editing, and Alternative CRISPR Cas9 Technologies for Precise Gene Therapy of Duchenne Muscular Dystrophy," Stem Cells International, 2017, pp. 1-11.
Gemberling et al., "Transgenic mice for in vivo epigenome editing with CRISPR-based systems," Nat Methods, 2021, 18(8): 965-974.
Genbank Accenssion AP006627.1 (2016).
Genbank Accenssion BA000004.3 (2016).
Genbank Accenssion BAB04055.1 (2016).
GenBank Accession No. AAC75803.1 (2018).
GenBank Accession No. AIN33136.1 (2014).
GenBank Accession No. BAB04055.1 (2017).
GenBank Accession No. EOT14076.1 (2013).
GenBank Accession No. AK019325 (2010).
GenBank Accession No. BB730912 (2001).
GenBank Accession No. BC010291 (2006).
GenBank Accession No. BC026642.1 (2007).
GenBank Accession No. BI143915 (2011).
GenBank Accession No. NM_020562.1 (2004).
GenBank P38036.2 (2013).
Ghisletti et al., "Identification and characterization of enhancers controlling the inflammatory gene expression program in macrophages," Immunity, 2010, 32: 317-328.
Gibson et al., "Enzymatic assembly of DNA molecules up to several hundred kilobases," Nature Methods, 2009, 6(5): 343-345.
Gilbert et al., "CRISPR-mediated modular RNA-guided regulation of transcription in eukaryotes," Cell, 2013, 154: 442-451.
Gillespie, "A general method for numerically simulating the stochastic time evolution of coupled chemical reactions," Journal of computational physics, 1976, 22: 403-434.
Gomaa et al., "Programmable Removal of Bacterial Strains by Use of Genome-Targeting CRISPR-Cas Systems," 2014, mBio 5(1): e00928-13.
Gonda "Aerosols for delivery of therapeutic and diagnostic agents to the respiratory tract," Critical Reviews in Therapeutic Drug Carrier Systems, 1990 6:273-313.
Gong et al., "Molecular insights into DNA interference by CRISPR-associated nuclease-helicase Cas3," Proc Natl Acad Sci U S A, 2014, 111(46):16359-64.
Gray et al., "G quadruplexes are genomewide targets of transcriptional helicases XPB and XPD," Nat. Chem. Biol, 2014, 10: 313-318.
Grissa et al., "CRISPRFinder: a web tool to identify clustered regularly interspaced short palindromic repeats," Nucleic Acids Res., 2007, 35(Web Server issue):W52-57.
Guo et al., "Directed evolution of an enhanced and highly efficient Fokl cleavage domain for zinc finger nucleases," J Mol Biol, 2010, 400: 96-107.
Hacein-Bey-Abina et al., "LMO2-associated clonal T cell proliferation in two patients after gene therapy for SCID-X1," Science, 2003, 302: 415-419.
Hart et al., "High-Resolution CRISPR Screens Reveal Fitness Genes and Genotype-Specific Cancer Liabilities," Cell, 2015, 163: 1515-1526.
Hayward et al., "Whole-genome landscapes of major melanoma subtypes," Nature, 2017, 545: 175-180.
He et al., "Molecular Genetic Mechanisms of Hereditary Spherocytosis: Current Perspectives," Acta Haematol., 2018, 139: 60-66.
Heasman, "Morpholino oligos: making sense of antisense?," Dev. Biol., 2002, 243(2): 209-214.
Henikoff et al., "Amino acid substitution matrices from protein blocks," Proc. Natl. Acad. Sci. USA, 1992, 89: 10915-9.
Henning et al., "Epigenetic control of CD8 + T cell differentiation," Nat Rev Immunol, 2018, 18(5): 340-356.
Hori et al., "Simple and reproducible hepatectomy in the mouse using the clip technique," World J Gastroenterol, 2012, 18(22): 2767-2774.
Howarth et al., "A monovalent streptavidin with a single femtomolar biotin binding site," Nature methods, 2006, 3(4): 267-273.
Hsu et al., "Development and applications of CRISPR-Cas9 for genome engineering," Cell, 2014, 157(6): 1262-1278.
Huang et al., "Generation and comparison of CRISPR-Cas9 and Cre-mediated genetically engineered mouse models of sarcoma," Nature Communications, 2017, 8(15999): 1-11.
Huntriss et al., "Imprinted expression of SNRPN in human preimplantation embryos," Am J Hum Genet, 1998, 63: 1009-1014.
Jansen et al., "Identification of genes that are associated with DNA repeats in prokaryotes, " Mol Microbiol, 2002, 43(6): 1565-1575.
Jeltsch et al., "Application of DNA methyltransferases in targeted DNA methylation," Appl. Microbiol. Biotechnol., 2007, 75(6): 1233-1240.
Jepsen et al., "Locked nucleic acid: a potent nucleic acid analog in therapeutics and biotechnology," Oligonucleotides, 2004, 14(2): 130-146.
Jiang et al., "A Cas9-guide RNA complex preorganized for target DNA recognition," Science, 2015, 348, 1477-1481.
Jiang et al., "RNA-guided editing of bacterial genomes using CRISPR-Cas systems," Nat. Biotechnol., 2013, 31:233-239.
Jimenez et al., "Activation of the beta-globin locus control region precedes commitment to the erythroid lineage," Proceedings of the National Academy of Sciences, 1992, 89: 10618-10622.
Jobling et al., "Chitayat-Hall and Schaaf-Yang syndromes:a common aetiology: expanding the phenotype of MAGEL2-related disorders," J Med Genet, 2018, 55: 316-321.
Josephs et al., "Structure and specificity of the RNA-guided endonuclease Cas9 during DNA interrogation, target binding and cleavage, " Nucleic Acids Research, 2015, 43(18): 8924-8941.
Joyce, "Amplification, mutation and selection of catalytic RNA," Gene, 1989, 82(1): 83-87.
Joyce, "Directed molecular evolution," Scientific American, 1992, 267(6): 90-97.
Jurkowska and Jeltsch, "Silencing of Gene Expression by Targeted DNA Methylation: Concepts and Approaches," Methods Mol. Biol. 649, 2010, Chapter 9: 149-161.
Kabadi et al., "Engineering Synthetic TALE and CRISPR/Cas9 Transcription Factors for Regulating Gene Expression," Methods, 2014, 69(2): 188-197.
Kabanov et al., "A new class of antivirals: antisense oligonucleotides combined with a hydrophobic substituent effectively inhibit influenza virus reproduction and synthesis of virus-specific proteins in MDCK cells," FEBS Lett., 1990, 259: 327-330.
Karlin et al., "Applications and statistics for multiple high-scoring segments in molecular sequences," Proc. Natl. Acad. Sci. USA, 1993, 90: 5873-77.
Kauppinen et al., "Locked nucleic acid (LNA): High affinity targeting of RNA for diagnostics and therapeutics," Drug Discov Today Technol, 2005, 2(3): 287-290.
Kempfer et al., "Methods for mapping 3D chromosome architecture," Nat. Rev. Genet., 2020, 21: 207-226.
Keys et al., "A genome-wide screen in the mouse liver reveals sex-specific and cell non-autonomous regulation of cell fitness," bioRxiv preprint doi: https://doi.org/10.1101/2021.01.30.428976, posted Feb. 1, 2021.
Khodakov et al., "Protected DNA strand displacement for enhanced single nucleotide discrimination in double-stranded DNA," Scientific reports, 2015, 5: 8721.
Khurana et al., "Role of non-coding sequence variants in cancer," Nat. Rev. Genet., 2016, 17: 93-108.
Kim et al., "Epigenetic therapy of Prader-Willi Syndrome," Transl Res, 2019, 208: 105-118.
Kim et al., "Histone acetylation contributes to chromatin looping between the locus control region and globin gene by influencing hypersensitive site formation," Biochim Biophys Acta, 2013, 1829: 963-969.
Kim et al., "Targeting the histone methyltransferase G9a activates imprinted genes and improves survival of a mouse model of Prader-Willi syndrome," Nat Med, 2017, 23: 213-222.
Kim et al., "Engineering and Application of Zinc Finger Proteins and TALEs for Biomedical Research," Mol Cells, 2017, 40(8): 533-541.

(56) References Cited

OTHER PUBLICATIONS

Klann et al., "Genome-wide annotation of gene regulatory elements linked to cell fitness," bioRxiv doi: 10.1101/2021.03.08.434470. Preprint posted Mar. 9, 2021, 42 pages.
Kleinstiver et al., "Engineered CRISPR-Cas9 nucleases with altered PAM specificities," Nature, 2015, 523(7561): 481-485.
Koblan et al., "Improving cytidine and adenine base editors by expression optimization and ancestral reconstruction," Oct. 2018, 36(9): 843-846.
Kocak, "Synthetic Transcription Factors and their Effects on Endogenous DNA Methylation in Human Cells," Thesis submitted in partial fulfillment of the requirements for the degree of Master of Science in the Department of Biomedical Engineering in the Graduate School of Duke University, 2013, p. 1-29.
Kocher et al., "Phylogenetic Analysis of the SNORD116 Locus," Genes, 2017, 8(12): 358.
Komor et al., "Programmable editing of a target base in genomic DNA without double-stranded DNA cleavage, " Nature, 2016, 533(7603): 420-424.
Korkmaz et al., "Functional genetic screens for enhancer elements in the human genome using CRISPR-Cas9," Nat Biotechnol, 2016, 34: 192-198.
Kornberg et al., "DNA Replication," 1980, pp. 75-77.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 1998, 54(14): 3607-3630.
Kuhnel et al., "Tumor-specific adenoviral gene therapy: Transcriptional repression of gene expression by utilizing p53—signal transduction pathways," Cancer Gene Ther., 2004, 11: 28-40.
Kumar et al., "Artificial evolution and natural ribozymes," FASEB Journal, 1995, 9: 1183-1195.
Kurreck, "Antisense technologies. Improvement through novel chemical modifications," European Journal of Biochemistry, 2003, 270(8): 1628-1644.
Kwa et al., "Chromatin modifying agents - the cutting edge of anticancer therapy," Drug Discovery Today, 2011, 16(13/14):543-547.
Lacerra et al., "Restoration of hemoglobin A synthesis in erythroid cells from peripheral blood of thalassemic patients," Proc. Natl. Acad. Sci., 2000, 97(17): 9591-9596.
Landry et al., "Expression of the leukemia oncogene Lmo2 is controlled by an array of tissue-specific elements dispersed over 100 kb and bound by Tal1/Lmo2, Ets, and Gata factors," Blood, 2009, 113: 5783-5792.
Langouet et al., "Zinc finger protein 274 regulates imprinted expression of transcripts in Prader-Willi syndrome neurons," Hum Mol Genet, 2018, 27: 505-515.
Laumont et al., "Noncoding regions are the main source of targetable tumor-specific antigens," Sci. Transl. Med., 2018, 10(470): eaau5516, 11 pages.
Lawrence et al., "Discovery and saturation analysis of cancer genes across 21 tumour types," Nature, 2014, 505: 495-501.
Lee et al., "Expression of small interfering RNAs targeted against HIV-1 rev transcripts in human cells," Nature Biotechnol, 2002, 20(5): 500-505.
Lenoir et al., "PICKLES: the database of pooled in-vitro CRISPR knockout library essentiality screens," Nucleic Acids Res, 2018, 46: D776-D780.
Lesnik et al., "Relative thermodynamic stability of DNA, RNA, and DNA: RNA hybrid duplexes: relationship with base composition and structure," Biochemistry, 1995, 34(34): 10807-10815.
Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86(17): 6553-6556.
Levin et al., "Position-dependent effects of locked nucleic acid (LNA) on DNA sequencing and PCR primers," Nuc. Acids. Res., 2006, 34: e142.

Levskaya et al., "Synthetic biology: engineering *Escherichia coli* to see light," Nature, 2005, 438:441-442.
Li et al., "Chimeric DNA methyltransferases target DNA methylation to specific DNA sequences and repress expression of target genes," Nucleic Acids Res., 2007, 35(1): 100-112.
Li et al., "Ex vivo cell-based CRISPR/Cas9 genome editing for therapeutic applications," Biomaterials, 2020, 234: 119711.
Li et al., "The autism-related gene SNRPN regulates cortical and spine development via controlling nuclear receptor Nr4a1," Sci Rep, 2016, 6: 29878.
Liao et al., "In Vivo Target Gene Activation via CRISPR/Cas9-Mediated Trans-epigenetic Modulation," Cell, 2017, 171: 1495-1507.
Lin et al., "Essential Role of the 58-kDa Microspherule Protein in the Modulation of Daxx- dependent Transcriptional Repression as Revealed by Nucleolar Sequestration," J Biol Chem, 2002, 277: 25446-25456.
Liu et al., "Editing DNA Methylation in the Mammalian Genome," Cell, Sep. 2016, 167(1): 233-247.
Liu et al., "Monte Carlo simulation for single RNA unfolding by force," Biophysical journal, 2005, 88(1): 76-84.
Luo et al., "Repurposing endogenous type I CRISPR-Cas systems for programmable gene repression," Nucleic Acids Research, 2014, 43(1): 674-681.
Ma et al., "Targeted gene suppression by inducing de novo DNA methylation in the gene promoter," Epigenetics Chromatin, 2014, 7: 20.
Machinek et al., "Programmable energy landscapes for kinetic control of DNA strand displacement," Nature communications, 2014, 5: 5324, 9 pages.
MacPherson et al., "Flexible guide-RNA design for CRISPR applications using Protospacer Workbench," Nature biotechnology, 2015, 33(8): 805-806.
Mader et al., "CRISPR RNA-guided activation of endogenous human genes," Nature Methods, 2013, 10(10): 977-979.
Maeder et al., "Robust, synergistic regulation of human gene expression using TALE activators," Nat Methods, 2013, 10(3): 243-245.
Majzner et al., "Clinical lessons learned from the first leg of the CAR T cell journey," Nature Medicine, 2019, 25(9): 1341-1355.
Makarova et al., "An updated evolutionary classification of CRISPR-Cas systems," Nature Reviews Microbiology, 2015, 13:722-736.
Makarova et al., "Evolution and classification of the CRISPR-Cas systems," Nature Reviews Microbiology, 2011, pp. 467-477.
Manoharan et al., "Chemical Modifications to Improve Uptake and Bioavailability of Antisense Oligonucleotides," Ann. N. Y. Acad. Sci., 1992, 660: 306-309.
Manoharan et al., "Cholic acid-oligonucleotide conjugates for antisense applications," Bioorg. Med. Chem. Let., 1994, 4(8): 1053-1060.
Manoharan et al., "Introduction of a lipophilic thioether tether in the minor groove of nucleic acids for antisense applications," Bioorg. Med. Chem. Let., 1993, 3(12): 2765-2770.
Manoharan et al., "Lipidic Nucleic Acids, " Tetrahedron Lett, 1995, 36: 3651-3654.
Manoharan et al., "Oligonucleotide Conjugates: Alteration of the Pharmacokinetic Properties of Antisense Agents," Nucleosides & Nucleotides, 1995, 14: 969-973.
Martin et al., "A New Access to 2'-O-Alkylated Ribonucleosides and Properties of 2'-O-Alkylated Oligoribonucleotides, " Helv. Chim. Acta, 1995, 78: 486-504.
Mastellos et al., "Inducing and characterizing liver regeneration in mice: Reliable models, essential "readouts" and critical perspectives," Curr Protoc Mouse Biol., 2013, 3(3): 141-170.
Mathews et al., "Expanded sequence dependence of thermodynamic parameters improves prediction of RNA secondary structure," Journal of Molecular Biology, 1999, 288(5): 911-940.
Maurano et al., "Systematic localization of common disease-associated variation in regulatory DNA," Science, 2012, 337: 1190-1195.
Maxwell et al., "A detailed cell-free transcription-translation-based assay to decipher CRISPR protospacer-adjacent motifs," Methods, 2018, 143: 48-57.

(56) References Cited

OTHER PUBLICATIONS

McCarthy et al., "Schaaf-Yang syndrome overview: Report of 78 individuals," Am J Med Genet A, 2018, 176(12): 2564-2574.
McTigue et al., "Sequence-dependent thermodynamic parameters for locked nucleic acid (LNA)-DNA duplex formation," Biochemistry, 2004, 43(18): 5388-5405.
Mevissen et al., "Molecular basis of Lys11-polyubiquitin specificity in the deubiquitinase Cezanne," Nature, 2016, 538(7625): 402-405.
Meyers et al., "Computational correction of copy No. effect improves specificity of CRISPR-Cas9 essentiality screens in cancer cells," Nat. Genet., 2017, 49: 1779-1784.
Min et al., "CRISPR Correction of Duchene Muscular Dystrophy," Annual Review of Medicine, Epub Oct. 2018, 70: 239-255.
Mishra et al., "Improved leishmanicidal effect of phosphorotioate antisense oligonucleotides by LDL-mediated delivery," Biochim. Biophys. Acta, 1995, 1264(2): 229-237.
Miyagishi et al., "U6 promoter-driven siRNAs with four uridine 3' overhangs efficiently suppress targeted gene expression in mammalian cells," Nature Biotechnol, 2002, 20(5): 497-500.
Mojica et al., "Intervening sequences of regularly spaced prokaryotic repeats derive from foreign genetic elements," J Molec Evolution, 2005, 60(2): 174-182.
Mojica et al., "Short motif sequences determine the targets of the prokaryotic CRISPR defence system," Microbiology, 2009, 155: 733-740.
Moore et al., "Transcription Activator-like Effectors: A Toolkit for Synthetic Biology," ACS Synth Biol, 2014, 3(10): 708-716.
Murray et al., "Codon usage in plant genes," Nucl. Acids Res., 1989, 17:477-498.
Naguibneva et al., "An LNA-based loss-of-function assay for micro-RNAs, " Biomed Pharmacother, 2006, 60: 633-638.
Nam et al., "Cas5d protein processes pre-crRNA and assembles into a Cascade-like interference complex in Subtype I-C/Dvulg CRISPR-Cas system," Structure, 2012, 20:1574-1584.
Nasevicius et al., "Effective targeted gene 'knockdown' in zebrafish," Nat. Genet., 2000, 26(2): 216-220.
Nguyen et al., "Transcriptional Enhancers in the Regulation of T Cell Differentiation," Front. Immunol., 2015, 6: 462.
Nielsen et al., "Sequence-selective recognition of DNA by strand displacement with a thymine-substituted polyamide," Science, 1991, 254: 1497-1500.
Nikfarjam et al., "A Model of Partial Hepatectomy in Mice," Journal of Investigative Surgery, 2004, 17(5): 291-294.
Nowotny et al., "Crystal structures of RNase H bound to an RNA/DNA hybrid: substrate specificity and metal-dependent catalysis," Cell, 2005, 121(7): 1005-1016.
Nuñez et al., "Genome-wide programmable transcriptional memory by CRISPR-based epigenome editing," Cell, 2021, 184(9): P2503-2519.
O'Brien et al., "GT-Scan: identifying unique genomic targets," Bioinformatics, 2014, 30: 2673-2675.
Oberhauser et al., "Effective incorporation of 2'-O-methyl-oligoribonucleotides into liposomes and enhanced cell association through modification with thiocholesterol," Nucl. Acids Res., 1992, 20(3): 533-538.
Obika et al., "Stability and structural features of the duplexes containing nucleoside analogues with a fixed N-type conformation, 2'-0,4'-C-methyleneribonucleosides," Tetrahedron Lett. 1998, 39(30): 5401-5404.
O'Connell et al., "Programmable RNA recognition and cleavage by CRISPR/Cas9," Nature, 2014, 516: 263-266.
O'Geen et al., "dCas9-based epigenome editing suggests acquisition of histone methylation is not sufficient for target gene repression," Nucleic Acids Res, 2017, 45: 9901-9916.
Orgel, "Selection in vitro," Proc. R. Soc. B, 1979, 205: 435-442.
Orlando et al., "Promoter capture Hi-C-based identification of recurrent noncoding mutations in colorectal cancer," Nat. Genet., 2018, 50: 1375-1380.
Orom et al., "LNA-modified oligonucleotides mediate specific inhibition of microRNA function," Gene, 2006, 372: 137-141.

Ousterout, "Genetic Correction of Duchenne Muscular Dystrophy using Engineered Nucleases," Dept. of Biomedical Engineering Duke University (Dissertation), 2014, pp. 1-204.
Paddison et al., "Short hairpin RNAs (shRNAs) induce sequence-specific silencing in mammalian cells," Genes & Dev, 2002, 16(8): 948-958.
Paez-Espino et al., "CRISPR immunity drives rapid phage genome evolution in *Streptococcus thermophilus*," mBio, 2015, 6(2): e00262-15.
Paul et al., "Effective expression of small interfering RNA in human cells," Nature Biotechnol, 2002, 20(5): 505-508.
Penczek et al., "Three-dimensional reconstruction of single particles embedded in ice," Ultramicroscopy, 1992, 40, 33-53.
Perez-Pinera et al., "Synergistic and tunable human gene activation by combinations of synthetic transcription factors," Nat Methods, 2013, 10: 239-242.
Pinello et al., "Analyzing CRISPR genome-editing experiments with CRISPResso," Nat Biotechnol, 2016, 34(7):695-697.
Ponting et al., "Evolution and functions of long noncoding RNAs," Cell, 2009, 136(4): 629-641.
Povero et al., "Lipid-induced toxicity stimulates hepatocytes to release angiogenic microparticles that require Vanin-1 for uptake by endothelial cells," Sci Signal, 2013, 6(296): ra88.
Powell et al., "A Prader-Willi locus lncRNA cloud modulates diurnal genes and energy expenditure," Hum Molec Genet, 2013, 22: 4318-4328.
Puccini et al., "Colorectal cancer: epigenetic alterations and their clinical implications", Biochim Biophys Acta, 2017, vol. 1868, No. 2, pp. 439-448.
Raeburn et al., "Techniques for drug delivery to the airways, and the assessment of lung function in animal models," J. Pharmacol. Toxicol. Meth., 1992, 27:143-159.
Rajagopal et al., "High-throughput mapping of regulatory DNA," Nat. Biotechnol, 2016, 34: 167-174.
Ran et al., "Genome engineering using the CRISPR-Cas9 system," Nature Protocols, 2013, 8(11): 2281-2308.
Ratcliff et al., "A novel single-molecule study to determine protein-protein-protein association constants," Journal of the American Chemical Society, 2001, 123(24): 5632-5635.
Rauscher et al., "GenomeCRISPR—a database for high-throughput CRISPR/Cas9 screens," Nucleic Acids Res, 2017, 45: D679-D686.
Rheinbay et al., "Analyses of non-coding somatic drivers in 2,658 cancer whole genomes," Nature, 2020, 578: 102-111.
Rhodes et al., "G-quadruplexes and their regulatory roles in biology," Nucleic Acids Res, 2015, 43: 8627-8637.
Richter et al., "Phage-assisted evolution of an adenine base editor with improved Cas domain compatibility and activity," Nat Biotechnol, Jul. 2020, 38(7): 883-891.
Rmilah et al., "Understanding the marvels behind liver regeneration," Wiley Interdiscip Rev Dev Biol., 2019, 8(3): e340.
Rodriguez et al., "Clustering by fast search and find of density peaks," Science, 2014, 344(6191): 1492-1496.
Russa et al. "The New State of the Art: Cas9 for Gene Activation and Repression," Molecular and Cellular Biology, 2015, 35(22):3800-3809.
Rutkauskas et al., "Directional R-loop formation by the CRISPR-Cas surveillance complex cascade provides efficient off-target site rejection," Cell reports, 2015, 10, 1534-1543.
Sahoo et al., "Prader-Willi phenotype caused by paternal deficiency for the HBII-85 C/D box small nucleolar RNA cluster," Nat Genet, 2008, 40: 719-721.
Saitoh et al., "Parent-of-Origin Histone Acetylation and Reactivation of a Key Imprinted Gene Locus in Prader-Willi Syndrome," Am J Hum Genet, 2000, 66: 1958-1962.
Sanghvi et al., "Heterocyclic Base Modifications in Nucleic Acids and their Applications in Antisense Oligonucleotides, " 1993, Antisense Research and Applications, Chapter 15, pp. 274-285.
Sanjana et al., "High-resolution interrogation of functional elements in the noncoding genome," Science, 2016, 353: 1545-1549.
Santalucia et al., "Improved nearest-neighbor parameters for predicting DNA duplex stability," Biochemistry, 1996, 35(11): 3555-3562.

(56) References Cited

OTHER PUBLICATIONS

Schaaf et al., "Truncating mutations of MAGEL2 cause Prader-Willi phenotypes and autism," Nat Genet, 2013, 45(11): 1405-1408.
Schifrut et al., "Genome-wide CRISPR Screens in Primary Human T Cells Reveal Key Regulators of Immune Function," Cell, 2018, 175(7): 1958-1971.e15.
Schmidt et al., "GenomeRNAi: a database for cell-based and in vivo RNAi phenotypes, 2013 update," Nucleic Acids Res, 2013, 41: D1021-6.
Schmittgen et al., "Analyzing real-time PCR data by the comparative CT method," Nature Protocols, 2008, 3(6): 1101-1108.
Schreck et al., "DNA hairpins destabilize duplexes primarily by promoting melting rather than by inhibiting hybridization," Nucleic Acids Research, 2015, 43(13): 6181-6190.
Schreck et al., "DNA hairpins primarily promote duplex melting rather than inhibiting hybridization," 2014, arXiv preprint arXiv:1408.4401.
Segal and Meckler, "Genome Engineering at the Dawn of the Golden Age," Annu. Rev. Genomics Hum. Genet., 2013, 14: 135-158.
Semenova et al., "The Cas6e ribonuclease is not required for interference and adaptation by the *E. coli* type I-E CRISPR-Cas system," Nucleic Acids Res, 2015, 43(12):6049-61.
Sengupta et al., "Super-Enhancer-Driven Transcriptional Dependencies in Cancer," Trends Cancer Res, 2017, 3: 269-281.
Sentmanat et al., "A Survey of Validation Strategies for CRISPR-Cas9 Editing," Scientific Reports, 2018, 8: 888.
Serra et al., "Predicting thermodynamic properties of RNA," Methods in Enzymology, 1995, 259: 242-261.
Shalem et al., "Genome-scale CRISPR-Cas9 knockout screening in human cells," Science, 2014, 343: 84-87.
Shea et al., "Synthesis, hybridization properties and antiviral activity of lipid-oligodeoxynucleotide conjugates," Nucl. Acids Res, 1990, 18: 3777-3783.
Shlyakhtenko et al., "Silatrane-based surface chemistry for immobilization of DNA, protein-DNA complexes and other biological materials," Ultramicroscopy, 2003, 97: 279-287.
Siddique et al., "Targeted methylation and gene silencing of VEGF-A in human cells by using a designed Dnmt3a-Dnmt3L single-chain fusion protein with increased DNA methylation activity," J. Mol. Biol., 2013, 425(3): 479-491.
Simpson, "Contacts between *Escherichia coli* RNA polymerase and thymines in the lac UV5 promoter," Proc. Natl. Acad. Sci. USA, 1979, 76: 3233-3237.
Singh et al. "Protein Engineering Approaches in the Post-Genomic Era," Current Protein and Peptide Science, 2017, 18: 1-11.
Soejima et al., "Imprinting centers, chromatin structure, and disease," J Cell Biochem, 2005, 95(2): 226-233.
Stanton et al., "Chemical modification study of antisense gapmers," Nucleic Acid Ther., 2012, 22(5): 344-359.
Stemmer et al., "CCTop: An Intuitive, Flexible and Reliable CRISPR/Cas9 Target Prediction Tool," PLoS One, 2015, 10(4): e0124633.
Stephens, "False discovery rates: a new deal," Biostatistics, 2017, 18: 275-294.
Stepper et al., "Efficient targeted DNA methylation with chimeric dCas9-Dnmt3a-Dnmt3L methyltransferase," Nucleic Acids Res., 2017, 45(4): 1703-1713.
Stolzenburg et al., "Targeted silencing of the oncogenic transcription factor SOX2 in breast cancer," Nucleic Acids Res., 2012, 40(14): 6725-6740.
Su et al., "Identification of biologically relevant enhancers in human erythroid cells," J Biol Chem, 2013, 288: 8433-8444.
Sugimoto et al., "Thermodynamic parameters to predict stability of RNA/DNA hybrid duplexes," Biochemistry, 1995, 34: 11211-11216.
Sugimoto et al., "Thermodynamics-structure relationship of single mismatches in RNA/DNA duplexes," Biochemistry, 2000, 39: 11270-11281.
Sui et al., "A DNA vector-based RNAi technology to suppress gene expression in mammalian cells," PNAS, 2002, 99(8): 5515-5520.
Sun et al., "Phage mutations in response to CRISPR diversification in a bacterial population," Environmental microbiology, 2013, 15(2): 463-470.
Sur et al., "The role of enhancers in cancer," Nat. Rev. Cancer., 2016, 16: 483-493.
Sutcliffe et al., "Deletions of a differentially methylated CpG island at the SNRPN gene define a putative imprinting control region," Nature Genetics, 1994, 8: 52-58.
Svinarchuk et al., "Inhibition of HIV proliferation in MT-4 cells by antisense oligonucleotide conjugated to lipophilic groups," Biochimie, 1993, 75: 49-54.
Szczelkun et al., "Direct observation of R-loop formation by single RNA-guided Cas9 and Cascade effector complexes," Proceedings of the National Academy of Sciences, 2014, 6 pages.
Szostak, "in Vitro Genes," TIBS, 1993, 17: 89-93.
Szymczak et al., "Correction of multi-gene deficiency in vivo using a single 'self-cleaving' 2A peptide-based retroviral vector," Nature Biotechnology, 2004, 22(5): 589-594.
Takami et al., "Complete Genome Sequence of the Alkaliphilic Bacterium Bacillus halodurans and Genomic Sequence Comparison with Bacillus subtilis," Nucleic Acids Research, 2000, 28(21): 4317-4331.
Tam et al., "Benefits and limitations of genome-wide association studies," Nat. Rev. Genet., 2019, 20: 467-484.
Tan et al., "Rationally engineered Staphylococcus aureus Cas9 nucleases with high genome-wide specificity," Proc. Nat. Acad. Sci. USA, 2019, 116(46): 20969-20976.
Tracy, "Human DNA sequence from clone RP11-34D15 on chromosome 10, complete sequence," Genbank entry, National Center for Biotechnology Information, <https://www.ncbi.nlm.nih.gov/nucleotide/AL139819.8> 2012.
Tsai et al., "GUIDE-seq enables genome-wide profiling of off-target cleavage by CRISPR-Cas nucleases," Nature biotechnology, 2015, 33(2): 187-197.
Tyle, "Iontophoretic Devices for Drug Delivery," Pharm. Res., 1986, 3: 318-326.
U.S. Appl. No. 17/471,935, filed Sep. 10, 2021, by Gersbach et al. (Copy not submitted herewith pursuant to the waiver of 37 C.F.R. § 1.98(a)(2)(iii) issued by the Office on Sep. 21, 2004).
U.S. Appl. No. 17/636,750, filed Feb. 18, 2022, by Gersbach et al. (Copy not submitted herewith pursuant to the waiver of 37 C.F.R. § 1.98(a)(2)(iii) issued by the Office on Sep. 21, 2004).
U.S. Appl. No. 17/636,754, filed Feb. 18, 2022, by Gersbach et al. (Copy not submitted herewith pursuant to the waiver of 37 C.F.R. § 1.98(a)(2)(iii) issued by the Office on Sep. 21, 2004).
Urrutia, "KRAB-containing zinc-finger repressor proteins," Genome Biol., 2003, 4(10): 231.
Usman et al., "Catalytic RNA (Ribozymes) as Drugs," Ann. Rep. Med. Chem., 1995, Chapter 30, pp. 285-294.
van der Oost et al., "Unravelling the structural and mechanistic basis of CRISPR-Cas systems," Nature Reviews Microbiology, 2014, 12: 479-492.
Wada et al., "Codon usage tabulated from the GenBank genetic sequence data," Nucl. Acids Res., 1990, 18: 2367-2411.
Wang et al., "Cyclohexene Nucleic Acids (CeNA): Serum Stable Oligonucleotides that Activate RNase H and Increase Duplex Stability with Complementary RNA," J. Am. Chem. Soc., 2000, 122: 8595-8602.
Wang et al., "Gene Essentiality Profiling Reveals Gene Networks and Synthetic Lethal Interactions with Oncogenic Ras," Cell, 2017, 168: 890-903.e15.
Wang et al., "Genetic screens in human cells using the CRISPR-Cas9 system," Science, 2014, 343: 80-84.
Wang et al., "Identification and characterization of essential genes in the human genome," Science, 2015, 350: 1096-1101.
Wang et al., "Potential of Epigenetic Therapy for Pader-Willi Syndrome," Trends in Pharmacological Sciences, 2019, 40(9): 605-608.
Wang et al., "Unbiased detection of off-target cleavage by CRISPR-Cas9 and TALENs using integrase-defective lentiviral vectors," Nature biotechnology, 2015, 33(2): 175-8.

(56) References Cited

OTHER PUBLICATIONS

Watkins et al., "Thermodynamic contributions of single internal rA.dA, rC.dC, rG.dG and rU.dT mismatches in RNA/DNA duplexes," Nucleic acids research, 2011, 39(5): 1894-1902.
Wei et al., "Targeting Regnase-1 programs long-lived effector T cells for cancer therapy," Nature, 2019, 576(7787): 471-476.
Wherry, "T cell exhaustion," Nat. Immunology, 2011, 12: 492-499.
Wiggins et al., "High flexibility of DNA on short length scales probed by atomic force microscopy," Nature nanotechnology, 2006, 1(2): 137-141.
Wilbie et al., "Delivery Aspects of CRISPR/Cas for in Vivo Genome Editing," Acc Chem Res, 2019, 52(6): 1555-1564.
Wiles et al., "CRISPR-Cas9_mediated genome editing and guide RNA design," Mammalian Genome, 2015, 26(9): 501-510.
Wu et al., "Genome-wide binding of the CRISPR endonuclease Cas9 in mammalian cells," Nature biotechnology, 2014, 32(7): 670-6.
Wu et al., "Induction of anion exchanger-1 translation and its opposite roles in the carcinogenesis of gastric cancer cells and differentiation of K562 cells," Oncogene, 2010, 29: 1987-1996.
Wu et al., "Unusual Processing Generates SPA LncRNAs that Sequester Multiple RNA Binding Proteins," Mol Cell, 2016, 64: 534-548.
Xie et al., "Multiplexed Engineering and Analysis of Combinatorial Enhancer Activity in Single Cells," Mol. Cell, 2017, 66: 285-299. e5.
Yang et al., "Determination of protein-DNA binding constants and specificities from statistical analyses of single molecules: MutS-DNA interactions," Nucleic acids research, 2005, 33(13): 4322-4334.
Yang et al., "Gene Reactivation by 5-Aza-2'-Deoxycytidine-Induced Demethylation Requires SRCAP-Mediated HZA.Z Insertion to Establish Nucleosome Depleted Regions", PLoS Genetics, 2012, vol. 8, Issue 3, e1002604, 12 pages.
Yin et al., "Long noncoding RNAs with snoRNA ends," Mol Cell, 2012, 48(2): 219-230.
Yin et al., "Programming biomolecular self-assembly pathways," Nature, 2008, 451(7176): 318-323.
You et al., "Design of LNA probes that improve mismatch discrimination," Nuc. Acids. Res., 2006, 34(8): e60.
Younossi et al., "Epidemiology of chronic liver diseases in the USA in the past three decades," Gut, 2020, 69(3): 564-568.
Yu et al., "RNA interference by expression of short-interfering RNAs and hairpin RNAs in mammalian cells," PNAS, 2002, 99(9): 6047-6052.
Zenser et al., "A new TAP system for isolation of plant protein complexes and subsequent mass-spec analysis," <https://www.sigmaaldrich.com/deepweb/assets/sigmaaldrich/product/documents/388/028/flag_ ha_tap_poster.pdf> published 2008, printed as pp. 1/4-4/4.
Zhang et al., "Gene activation in human cells using CRISPR/Cpf1-p300 and CRISPR/Cpf1-SunTag systems," Protein Cell, 2018, 9: 380-383.
Zhang et al., "Myoediting: Toward Prevention of Muscular Dystrophy by Therapeutic Genome Editing," Physiological Reviews, 2018, 98(3): 1205-1240.
Zhang et al., "Propagated Perturbations from a Peripheral Mutation Show Interactions Supporting WW Domain Thermostability," Structure, 2018, 26: 1474-1485.
Zhao et al., "High-efficiency transfection of primary human and mouse T lymphocytes using RNA electroporation," Mol. Ther., 2006, 13: 151-159.
Zhao et al., "Intracellular delivery of artificial transcription factors fused to the protein transduction domain of HIV-1 Tat," Protein Expr Purif, 2013, 90(1): 27-33.
Zheng et al., "Foxp3 in control of the regulatory T cell lineage," Nat. Immunol. 2007, 8: 457-462.
Zhu et al., "The role of histone deacetylase 7 (HDAC7) in cancer cell proliferation: regulation on c-Myc," J. Mol. Med, 2011, 89: 279-289.
United States Patent Office Action for U.S. Appl. No. 16/098,464 dated Nov. 3, 2022 (13 pages).
NCBI Reference Sequence XM011532698.1 (2015).
NCBI Reference Sequence NM_004020.2 (2010).
NCBI Reference Sequence NG_028016.2 (2013).
United States Patent Office Action for U.S. Appl. No. 15/779,633 dated Dec. 21, 2022 (10 pages).
Ifuku et al., "Restoration of Dystrophin Protein Expression by Exon Skipping Utilizing CRISPR-Cas9 in Myoblasts Derived from DMD Patient iPS Cells," Methods Mol Biol, 2018, Chapter 12, pp. 191-217.
Min et al., "CRISPR Correction of Duchene Muscular Dystrophy Exon 44 Deletion Mutations in Mice and Human Cells," Science Advances, 2019, 5: eaav4324.
Robinson-Hamm et al., "Gene therapies that restore dystrophin expression for the treatment of Duchenne muscular dystrophy," Human Genetics, 2016, 135(9): 1029-1040.
Yu et al., "Dystrophin-deficient large animal models: translational research and exon skipping," Am J Transl Res, 2015, 7(8): 1314-1331.
United States Patent Office Action for U.S. Appl. No. 15/779,633 dated Apr. 19, 2023 (12 pages).
Park et al., "Cas-Designer: a web-based tool for choice of CRISPR-Cas9 target sites," Bioinformatics, 2015, 31(24): 4014-4016.
Shen et al., "Massively parallel cis-regulatory analysis in the mammalian central nervous system," Genome Research, 2015, 26(2): 238-255.
Chhatwal et al., "Identification of cell-type-specific promoters within the brain using lentiviral vectors," Gene Therapy, 2007, 14(7): 575-583.
Trinklein et al., " Identification and functional analysis of human transcriptional promoters," Genome Research, 2003, 13(2): 308-312.
United States Patent Office Action for U.S. Appl. No. 16/098,464 dated Aug. 1, 2023 (16 pages).
Adikusuma et al., "Versatile single-step-assembly CRISPR/Cas9 vectors for dual gRNA expression," 2017, 12(12): e0187236.
Carcagno et al., "Neurogenin3 Restricts Serotonergic Neuron Differentiation to the Hindbrain," The Journal of Neuroscience, 2014, 34(46): 15223-15233.
Kalsner et al., "Prader-Willi, Angelman, and 15q11-q13 Duplication Syndromes," Pediatric Clinics of North America United States, 2015, 62(3): 587-606.
Ohta et al., "Imprinting-Mutation Mechanisms in Prader-Willi Syndrome," The American Journal of Human Genetics, 1999, 64(2): 397-413.
Yang et al., "A dual AAV system enables the Cas9-mediated correction of a metabolic liver disease in newborn mice," Nature Biotechnology, 2016, 34(3): 334-338.
United States Patent Office Notice of Allowance for U.S. Appl. No. 15/779,633 dated Sep. 28, 2023 (9 pages).
Japanese Patent Office Action for Application No. 2022-105795 dated Aug. 24, 2023 (6 pages, English translation included).
Abaandou et al., "Affecting HEK293 Cell Growth and Production Performance by Modifying the Expression of Specific Genes," Cells, 2021, 10: 1667, 21 pages.
Alerasool et al., "An efficient KRAB domain for CRISPRi applications in human cells," Nat Methods, 2020, 17: 1093-1096.
Alonso-Camino et al., "CARbodies: Human Antibodies Against Cell Surface Tumor Antigens Selected From Repertoires Displayed on T Cell Chimeric Antigen Receptors," Mol Ther Nucl Acids, 2013, 2: e93, 11 pages.
Azuma et al., "Robust expansion of human hepatocytes in Fah-/-/Rag2-/-/Il2rg-/-mice" Nat Biotechnol., 2007, 25(8): 903-910.
Bhakta et al., "The generation of zinc finger proteins by modular assembly," Methods Mol. Biol., 2010, 649: 3-30.
Bloomfield, "Quasi-Elastic Light Scattering Applications in Biochemistry and Biology," Ann. Rev. Biophys. Bioeng., 1981, 10: 421-450.
Boris-Lawrie et al., "Recent advances in retrovirus vector technology," Cur. Opin. Genet. Develop., 1993, 3: 102-109.
Bouhairie et al., "Familial hypercholesterolemia," Cardiol. Clin., 2015, 33(2): 169-179.

(56) References Cited

OTHER PUBLICATIONS

Braliou et al., "The v-ErbA oncoprotein quenches the activity of an erythroid-specific enhancer," Oncogene, 2001, 20(7): 775-87.
Brash et al., "Strontium phosphate transfection of human cells in primary culture: stable expression of the simian virus 40 large-T-antigen gene in primary human bronchial epithelial cells," Mol. Cell Biol., 1987, 7(5): 2031-2034.
Broude et al., "p21 (CDKN1A) is a negative regulator of p53 stability," Cell Cycle, 2007, 6(12): 1468-1471.
Buckingham, M. et al. "The role of Pax genes in the development of tissues and organs: Pax3 and Pax7 regulate muscle progenitor cell functions." Annu. Rev. Cell Dev. Biol. 23 (2007): 645-673.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA, 1993, 90: 8033-8037.
Cano-Rodriguez et al., "Epigenetic Editing: On the Verge of Reprogramming Gene Expression at Will," Curr Genet Med Rep, 2016, 4: 170-179.
Carlens et al., "Ex vivo T lymphocyte expansion for retroviral transduction: influence of serum-free media on variations in cell expansion rates and lymphocyte subset distribution," Exp Hematol, 2000, 28(10): 1137-46.
Cavalieri et al., "Human T lymphocytes transduced by lentiviral vectors in the absence of TCR activation maintain an intact immune competence," Blood, 2003, 102(2): 497-505.
Chakraborty et al. "553. AAV-fVlediated Delivery of HSV-•Specific Homing Endonucleases To Neurons of the Trigeminal Ganglia for HSV-1 Inhibition." Molecular Therapy 22 (2014).
Chen et al., "Fusion protein linkers: property, design and functionality," Adv. Drug Deliv. Rev., 2013, 65(10): 1357-1369.
Chicaybam et al., "An efficient low cost method for gene transfer to T lymphocytes, " PLoS One, 2013, 8(3): e60298, 11 pages.
Chylinski et al., "The tracrRNA and Cas9 families of type II CRISPR-Cas immunity systems," RNA Biol., 2013, 10(5): 726-737.
Cooper et al., "T-cell clones can be rendered specific for CD19: toward the selective augmentation of the graft-versus-B-lineage leukemia effect," Blood, 2003, 101(4): 1637-1644.
Cortés-Mancera et al., "Gene-Targeted DNA Methylation: Towards Long-Lasting Reprogramming of Gene Expression?" Adv Exp Med Biol., 2022, 1389: 515-533.
Das et al., "Tet-On Systems For Doxycycline-inducible Gene Expression," Current Gene Therapy, 2016, 16: 156-167.
Defesche et al., "Familial hypercholesterolaemia," Nat. Rev. Dis. Primers, 2017, 3: 17093, 20 pages.
Deng et al., "Highly sensitive electrochemical methyltransferase activity assay," Anal Chem., 2014, 86: 2117-2123.
Fuks, "DNA methylation and histone modifications: teaming up to silence genes," Current Opinion in Genetics & Development, 2005, 15(5): 490-495.
Gersbach et al., "Synthetic zinc finger proteins: the advent of targeted gene regulation and genome modification technologies," Acc. Chem. Res., 2014, 47(8): 2309-18.
Gowher et al., "Mechanism of stimulation of catalytic activity of Dnmt3A and Dnmt3B DNA-(cytosine-C5)-methyltransferases by Dnmt3L," J. Biol. Chem., 2005, 280(14): 13341-13348.
Gowher et al., "Molecular enzymology of the catalytic domains of the Dnmt3a and Dnmt3b DNA methyltransferases," J. Biol. Chem., 2002, 277(23): 20409-20414.
Hochstrasser et al., "CasA mediates Cas3-catalyzed target degradation during Crispr Rna- guided interference," PNAS, 2014, 111(18): 6618-23.
Huang et al., "Ch 9: DNA transposons for modification of human primary T lymphocytes," Methods Mol Biol, 2009, 506: 115-126.
Jia et al., "Structure of Dnmt3a bound to Dnmt3L suggests a model for de novo DNA methylation," Nature, 2007, 449(7159): 248-251.
Johnston, "Biolistic transformation: microbes to mice," Nature, 1990, 346: 776-777.

Kao et al., "Ectopic DNMT3L triggers assembly of a repressive complex for retroviral silencing in somatic cells," J Virol., 2014, 88(18): 10680-95.
Kim et al., "Zinc-fingers and homeoboxes 1 (ZHX1) binds DNA methyltransferase (DNMT) 3B to enhance DNMT3B-mediated transcriptional repression," Biochemical and Biophysical Research Communications, 2007, 355(2): 318-323.
Koste et al., "T-cell receptor transfer into human T cells with ecotropic retroviral vectors," Gene Ther, 2014, 21(5): 533-538.
Lagace, "PCSK9 and LDLR degradation: regulatory mechanisms in circulation and in cells," Curr. Opin. Lipidol., 2014, 25(5): 387-393.
Lei et al., "Targeted DNA methylation in vivo using an engineered dCas9-MQ1 fusion protein," Nat. Commun, 2017, 8: 16026, 10 pages.
Li et al., "Development of fluorescent methods for DNA methyltransferase assay," Methods Appl. Fluoresc., 2017, 5: 012002, 8 pages.
Li et al., "The histone methyltransferase SETDB1 and the DNA methyltransferase DNMT3A interact directly and localize to promoters silenced in cancer cells," J. Biol. Chem., 2006, 281(28): 19489-19500.
Liu et al., "Design of polydactyl zinc-finger proteins for unique addressing within complex genomes," PNAS, 1997, 94(11): 5525-5530.
Ma et al., "Pol III Promoters to Express Small RNAs: Delineation of Transcription Initiation," Molecular Therapy—Nucleic Acids, 2014, 3: e161, 11 pages.
Makarova et al., "Annotation and Classification of CRISPR-Cas Systems," Methods Mol. Biol, 2015, 1311: 47-75.
Manuri et al., "piggyBac transposon/transposase system to generate CD19-specific T cells for the treatment of B-lineage malignancies," Hum Gene Ther, 2010, 21(4): 427-437.
Mavrothalassitis et al., "Proteins of the ETS family with transcriptional repressor activity," Oncogene, 2000, 19: 6524-6532.
Miller et al., "Improved retroviral vectors for gene transfer and expression," BioTechniques, 1989, 7(9): 980-990.
Miller, "Retrovirus packaging cells," Human Gene Therapy, 1990, 1: 5-14.
Milone et al., "Clinical use of lentiviral vectors," Leukemia, 2018, 32(7): 1529-1541.
Mok et al., "Stabilized plasmid-lipid particles: factors influencing plasmid entrapment and transfection properties," Biochimica et Biophysica Acta, 1999, 1419(2): 137-150.
Moon et al., "Recent advances in the CRISPR genome editing tool set," Exp. Mol. Med., 2019, 51(11): 130, 11 pages.
Moussa et al., "Here to stay: Writing lasting epigenetic memories," Cell, 2021, 184(9): 2281- 2283.
Murphy et al., "The Transcriptional Repressive Activity of KRAB Zinc Finger Proteins Does Not Correlate with Their Ability to Recruit TRIM28, " PLoS One, 2016, 11(9): e0163555, 19 pages.
O'Geen et al., "Determinants of heritable gene silencing for KRAB-dCas9 + DNMT3 and Ezh2-dCas9 + DNMT3 hit-and-run epigenome editing, " Nucleic Acids Res, 2022, 50(6): 3239-3253.
Orth et al., "Structural basis of gene regulation by the tetracycline inducible Tet repressor-operator system," natural structural biology, 2000, 7(3): 215-219.
Park et al., "Treating cancer with genetically engineered T cells," Trends Biotechnol, 2011, 29(11): 550-557.
Peterson et al., "PCSK9 function and physiology," J. Lipid Res., 2008, 49(6): 1152-1156.
Pickar-Oliver et al., "The next generation of CRISPR-Cas technologies and applications," Nature Reviews Molecular Cell Biology, 2019, 20(8): 490-507.
Poh et al., "DNA Methyltransferase Activity Assays: Advances and Challenges," Theranostics, 2016, 6(3): 369-391.
Poirier et al., "The proprotein convertase PCSK9 induces the degradation of low density lipoprotein receptor (LDLR) and its closest family members VLDLR and ApoER2"J. Biol. Chem., 2008, 283: 2363-2372.
Policarpi et al., "Epigenetic editing: Dissecting chromatin function in context," Bioessays, 2021, 43(5): e2000316, 16 pages.
Saha et al., "The NIH Somatic Cell Genome Editing program," Nature, 2021, 592: 195-204.

(56) References Cited

OTHER PUBLICATIONS

Scarpa et al., "Characterization of recombinant helper retroviruses from moloney-based vectors in ecotropic and amphotropic packaging cell lines," Virology, 1991, 180: 849-852.
Schellenberger et al., "A recombinant polypeptide extends the in vivo half-life of peptides and proteins in a tunable manner," Nature Biotechnology, 2009, 27(12): 1186-1190.
Sharma et al., "Efficient Sleeping Beauty DNA Transposition From DNA Minicircles," Molec Ther Nucl Acids, 2013, 2(2): e74, 10 pages.
Stepper, "Dissertation: CRISPR-Cas9 fusions for synthetic epigenetics," Von der Fakultat 4: Energie-, Verfahrens-und Biotechnik, Institut für Biochemie und Technische Biochemie der Universität Stuttgart, 2020, 148 pages.
Thakore et al., "385. Inhibiting the Myostatin Signaling Pathway using CRISPR/Cas9-Based Repressors." Molecular Therapy 2016, 24: S153.
Tycko et al., "High-Throughput Discovery and Characterization of Human Transcriptional Effectors," Cell, 2020, 183(7): 2020-2035.
Van Tedeloo et al., "High-level transgene expression in primary human T lymphocytes and adult bone marrow CD34+ cells via electroporation-mediated gene delivery," Gene Therapy, 2000, 7(16): 1431-1437.
Verhoeyen et al., "Ch 8: Lentiviral vector gene transfer into human T cells," Methods Mol Biol, 2009, 506: 97-114.
Wang et al., "Phenotypic and functional attributes of lentivirus modified CD19-specific human CD8+ central memory T cells manufactured at clinical scale," J. Immunother, 2012, 35(9): 689-701.
Wright et al., "Rational design of a split-Cas9 enzyme complex," PNAS, 2015, 112(10): 2984-2989.
Wright et al., "Standardized reagents and protocols for engineering zinc finger nucleases by modular assembly," Nat. Protoc., 2006, 1(3): 1637-1652.
Zetsche et al., "A split-Cas9 architecture for inducible genome editing and transcription modulation," Nat. Biotechnol, 2015, 33(2): 139-142.
European Patent Office Extended Search Report for Application No. 23195343.1 dated Jan. 2, 2024 (17 pages).
Japanese Patent Office Action for Application No. 2019-502579 dated Nov. 27, 2023 (6 pages, English translation included).
Echevarria et al., "Exon-skipping advances for Duchenne muscular dystrophy," Human Molecular Genetics, 2018, 27 (R2): R163-R172.
Miller, "Non-viral CRISPR/Cas gene editing in vitro and in vivo enabled by synthetic nanoparticle co-delivery of Cas9 mRNA and sgRNA," Angew Chem Int Engl, 2017, 56(4): 1059-1063.
Ryu et al., "Adenine base editing in mouse embryos and an adult mouse model of Duchenne muscular dystrophy," Nature Biotechnology, 2018, 36(6): 536-539.
Rees et al., "Base editing: precision chemistry on the genome and transcriptome of living cells," Nature Reviews Genetics, 2018, 19(12): 770-788.
Young, "Development of a Therapeutic CRISPR/Cas9 Plataform for Duchenne Muscular Dystrophy," UCLA Electronic Theses and Dissertations, Jan. 1, 2018, 136 pages.
United States Patent Office Action for U.S. Appl. No. 16/098,464 dated Feb. 12, 2024 (16 pages).
United States Patent Office Action for U.S. Appl. No. 15/779,633 dated Mar. 7, 2024 (5 pages).
Chen et al., "In vivo CD8+ T cell CRISPR screening reveals control by Fli1 in infection and cancer," Cell, 2021, 184(5): 1262-1280.
Corces et al., "An improved ATAC-seq protocol reduces background and enables interrogation of frozen tissues," Nature Methods. 2017, 14: 959-962.
Galletti et al., "Two subsets of stem-like CD8+ memory T cell progenitors with distinct fate commitments in humans," Nature Immunology, 2020, 21: 1552-1562.
Hao et al., "Integrated analysis of multimodal single-cell data," Cell, 2021, 184: 3573-3587.e29.
Hart et al., "Kruppel-like factors in lymphocyte biology," J Immunol, 2012, 188(2): 521-526.
Joung et al., "Transcription Factor Atlas of Directed Differentiation," Cell, 2023, 186(1): 209-229.e26.
Jung et al. "BLIMP1 and NR4A3 transcription factors reciprocally regulate antitumor Car T cell stemness and exhaustion," Cancer Immunotherapy, 2022, 14: eabn7336.
Kaminskiy et al., "Neglected, yet significant role of FOXP1 in T-cell quiescence, differentiation and exhaustion," Front. Immunol, 2022, 13: 971045.
Krishna et al., "Stem-like CD8 T cells mediate response of adoptive cell immunotherapy against human cancer," Science, 2020, 370: 1328-1334.
Kuleshov et al., "Enrichr: a comprehensive gene set enrichment analysis web server 2016 update," Nucleic Acids Research, 2016, 44: 90-97.
Liao et al., "featureCounts: an efficient general purpose program for assigning sequence reads to genomic features," Bioinformatics, 2013, 30(7): 923-930.
Mimitou et al., "Expanding the CITE-seq tool-kit: Detection of proteins, transcriptomes, clonotypes and CRISPR perturbations with multiplexing, in a single assay," Nat. Methods, 2019, 16: 409-412.
Philip et al., "Chromatin states define tumour-specific T cell dysfunction and reprogramming," Nature, 2017, 545: 452-456.
Pritykin et al., "A unified atlas of CD8 T cell dysfunctional states in cancer and infection," Mol. Cell 2021, 81: 2477-2493.
Ramirez et al., "deepTools: a flexible platform for exploring deep-sequencing data," Nucleic Acids Research, 2014, 42: W187-91.
Sen et al., "The epigenetic landscape of T cell exhaustion," Science, 2016, 354(6316): 1165-1169.
Wherry et al., "Molecular Signature of CD8+ T Cell Exhaustion during Chronic Viral Infection," Immunity, 2007, 27(4): 670-684.
Woolf et al., "Runx3 and Runx1 are required for CD8 T cell development during thymopoiesis," PNAS, 2003, 100(13): 7731-7736.
Yang et al., "The transcriptional regulators Id2 and Id3 control the formation of distinct memory CD8+ T cell subsets," Nat Immunol, 2011, 12: 1221-1229.
Yu et al., "ChIPseeker: an R/Bioconductor package for ChIP peak annotation, comparison and visualization," Bioinformatics, 2015, 31(14): 2382-2383.
Zhang et al., "Model-based analysis of ChIP-Seq (MACS)," Genome Biology, 2008, 9(9): R137.
Zheng et al., "Landscape of Infiltrating T Cells in Liver Cancer Revealed by Single-Cell Sequencing," Cell, 2017, 169: 1342-1356.
Vojta et al., "Repurposing the CRISPR-Cas9 system for targeted DNA methylation," Nucleic Acids Research, 2016, 44 (12): 5615-5628.
Chao et al., "Several log increase in therapeutic transgene delivery by distinct adeno-associated viral serotype vectors," (2000) Molecular Therapy 2:619.
Gao et al., "Clades of Adeno-Associated Viruses Are Widely Disseminated in Human Tissues," (2004) J. Virology 78:6381-6388.
GenBank Accession No. AF028704.1, (1998).
GenBank Accession No. AF028705.1, (1998).
GenBank Accession No. AF043303.1, (2010).
GenBank Accession No. AF063497.1, (1999).
GenBank Accession No. AF288061.1, (2001).
GenBank Accession No. AF513851.1, (2002).
GenBank Accession No. AFS13852.1, (2015).
GenBank Accession No. AH009962.2, (2016).
GenBank Accession No. AY028223.1, (2001).
GenBank Accession No. AY028226.1, (2001).
GenBank Accession No. AY530579.1, (2004).
GenBank Accession No. J01901.1, (1993).
GenBank Accession No. J02275.1, (1995).
Japanese Patent Office Action for Application No. 2022-105795 dated May 30, 2024 (3 pages, English translation included).
GenBank Accession No. NC_000883.2, (2018).
GenBank Accession No. NC_001358.1, (2015).
GenBank Accession No. NC_001401, (2018).
GenBank Accession No. NC_001510.1, (2018).

(56) References Cited

OTHER PUBLICATIONS

GenBank Accession No. NC_001540.1, (2018).
GenBank Accession No. NC_001701.1, (2018).
GenBank Accession No. NC_001729, (2018).
GenBank Accession No. NC_001829.1, (2018).
GenBank Accession No. NC_001862.1, (2004).
GenBank Accession No. NC_001863.1, (2004).
GenBank Accession No. NC_002077, (2018).
GenBank Accession No. NC_006152.1, (2018).
GenBank Accession No. NC_006261.1, (2018).
GenBank Accession No. U89790.1, (1997).
GenBank Accession No. X01457.1, (2005).
Martin et al., "CCR7 Deficiency in NOD Mice Leads to Thyroiditis and Primary Hyperthyroidism," The Journal of Immunology, 2009, 183(5): 3073-3080.
Mori et al., "Two novel adeno-associated viruses from cynomolgus monkey: pseudotyping characterization of capsid protein," (2004) Virology 330:375-383.
Muzyczka, "Use of adeno-associated virus as a general transduction vector for mammalian cells," (1992) Curr. Topics Microbial. Immunol. 158: 97-129.
Schubert et al., "Autosomal dominant immune dysregulation syndrome in humans with CTLA4 mutations," Nature Medicine, 2014, 20(2): 1410-1416.
Yuan et al., "Genetic Modulation of RNA Splicing with a CRISPR-Guided Cytidine Deaminase," Molecular Cell, 2018, 72(2): 380-394.
International Search Report and Written Opinion for Application No. PCT/US2023/076920 dated Apr. 29, 2024 (12 pages).
Bulcha et al., "Viral vector platforms within the gene therapy landscape," Signal Transduction and Targeted Therapy, 2021, 6: 53.
Duchêne et al., "CRISPR-Induced Deletion with SaCas Restores Dystrophin Expression in Dystrophic Models In Vitro and In Vivo," Molecular Therapy: The Journal of the American Society of Gene Therapy, 2018, 26(11): 2604-2616.
Hideki et al., Geneseq Accession No. BFK30060, 2018. Reference cited by examiner in U.S. Appl. No. 16/963,034, U. S. Patent Office Action dated Jun. 27, 2024.
Kotterman et al., "Engineering adeno-associated viruses for clinical gene therapy," Nature Reviews, 2014, 15(7): 445-451.
Lenzi et al., "Oversight and Review of Clinical Gene Transfer Protocols: Assessing the Role of the Recombinant DNA Advisory Committee," NCBI Bookshelf, A Service of the National Library of Medicine, National Institute of Health, Washington, DC, National Academies Press, US, 2014, pp. 1-16.
Liao, "Targeted disruption of DNMT1, DNMT3A and DNMT3B in human embryonic stem cells," Nature Genetics, 2015, 47(5): 469-478.
Long et al., "Correction of Diverse Muscular Dystrohpy Mutations in Human Engineered Heart Muscle by Single-Site Genome Editing," Sci Adv, 2018, 4(1): eaap9004.
Maggio et al., "Adenoviral vectors encoding CRISPR/Cas9 multiplexes rescue dystrophin synthesis in unselected populations of DMD muscle cells," Scientific Reports, 2016, 6: 37051.
Shim et al., "Nonviral Delivery Systems for Cancer Gene Therapy: Strategies and Challenges," Current Gene Therapy, 2017, 17(5): 1-18.
Swiech et al., "In vivo interrogation of gene function in the mammalian brain using CRISPR-Cas9," Nature Biotechnology, 2014, 33(1): 102-106 (Supplementary Information included).
Thule et al., "Engineered Insulin Secretion in Human Primary Thyroid Cells," Molecular Therapy, 2012, 20(Supplement 1): S164, Article 421.
United States Patent Office Notice of Allowance for U.S. Appl. No. 15/779,633 dated Sep. 5, 2024 (8 pages).
Liu et al., "A CRISPR-Cas9 Strategy for Activating the Saccharopolyspora erythraea Erythromycin Biosynthetic Gene Cluster with Knock-in Bidirectional Promoters," ACS Synth. Biol. 2019, 8(5): 1134-1143.
Miyazaki et al., "Characterization of deletion breakpoints in patients with dystrophinopathy carrying a deletion of exons 45-55 of the Duchenne muscular dystrophy (DMD) gene," Journal of Human Genetics, 2009, 54: 127-130.
Razzouk, "CRISPR-Cas9: A cornerstone for the evolution of precision medicine," Annal of Human Genetics, 2018, 82(6): 331-357.
Simeonov et al., "Discovery of stimulation-responsive immune enhancers with CRISPR activation," Nature, 2017, 549(7670): 111-115.

\* cited by examiner

SEQUENCE LISTING

<160> NUMBER OF SEQ ID NOS: 125

<210> SEQ ID NO 1
<211> LENGTH: 27
<212> TYPE: DNA

<213> ORGANISM: Homo sapiens

<400> SEQUENCE: 1
tttgcaaaaa cccaaaatat tttagct 27

<210> SEQ ID NO 2
<211> LENGTH: 27
<212> TYPE: DNA
<213> ORGANISM: Homo sapiens

<400> SEQUENCE: 2 tttgccttttt tggtatctta caggaac 27

<210> SEQ ID NO 3
<211> LENGTH: 27
<212> TYPE: DNA
<213> ORGANISM: Homo sapiens

<400> SEQUENCE: 3
tccaggatgg cattgggcag cggcaaa 27

<210> SEQ ID NO 4
<211> LENGTH: 27
<212> TYPE: DNA
<213> ORGANISM: Homo sapiens

<400> SEQUENCE: 4 tttattttc cttttattct agttgaa 27

<210> SEQ ID NO 5
<211> LENGTH: 27
<212> TYPE: DNA
<213> ORGANISM: Homo sapiens

<400> SEQUENCE: 5
tttcttgatc catatgcttt tacctgc 27

<210> SEQ ID NO 6
<211> LENGTH: 27
<212> TYPE: DNA
<213> ORGANISM: Homo sapiens

<400> SEQUENCE: 6
aggcgatttg acagatctgt tgagaaa 27

<210> SEQ ID NO 7
<211> LENGTH: 27
<212> TYPE: DNA
<213> ORGANISM: Homo sapiens

<400> SEQUENCE: 7
tttattcttc tttctccagg ctagaag 27

<210> SEQ ID NO 8
<211> LENGTH: 27
<212> TYPE: DNA
<213> ORGANISM: Homo sapiens

<400> SEQUENCE: 8
ttctttctcc aggctagaag aacaaaa 27

<210> SEQ ID NO 9
<211> LENGTH: 27

<212> TYPE: DNA
<213> ORGANISM: Homo sapiens

<400> SEQUENCE: 9
tacaggcaac aatgcaggat ttggaac                                              27

<210> SEQ ID NO 10
<211> LENGTH: 27
<212> TYPE: DNA
<213> ORGANISM: Homo sapiens

<400> SEQUENCE: 10
ttttctgtta aagaggaagt tagaaga                                              27

<210> SEQ ID NO 11
<211> LENGTH: 27
<212> TYPE: DNA
<213> ORGANISM: Homo sapiens

<400> SEQUENCE: 11
ttttaaaatt tttatattac agaatat                                              27

<210> SEQ ID NO 12
<211> LENGTH: 27
<212> TYPE: DNA
<213> ORGANISM: Homo sapiens

<400> SEQUENCE: 12
agaatataaa agatagtcta caacaaa                                              27

<210> SEQ ID NO 13
<211> LENGTH: 27
<212> TYPE: DNA
<213> ORGANISM: Homo sapiens

<400> SEQUENCE: 13
tttattttgc attttagatg aaagaga                                              27

<210> SEQ ID NO 14
<211> LENGTH: 27
<212> TYPE: DNA
<213> ORGANISM: Homo sapiens

<400> SEQUENCE: 14
ttttagatga aagagaagat gttcaaa                                              27

<210> SEQ ID NO 15
<211> LENGTH: 27
<212> TYPE: DNA
<213> ORGANISM: Homo sapiens

<400> SEQUENCE: 15
gatgaaagag aagatgttca aaagaaa                                              27

<210> SEQ ID NO 16
<211> LENGTH: 27
<212> TYPE: DNA
<213> ORGANISM: Homo sapiens

<400> SEQUENCE: 16
tttgcaaaaa cccaaaatat tttagct                                              27

<210> SEQ ID NO 17

```
<211> LENGTH: 27
<212> TYPE: DNA
<213> ORGANISM: Homo sapiens

<400> SEQUENCE: 17
tttagcttgt gtttctaatt tttcttt                                           27

<210> SEQ ID NO 18
<211> LENGTH: 27
<212> TYPE: DNA
<213> ORGANISM: Homo sapiens

<400> SEQUENCE: 18
tttgacttat tgttattgaa attggct                                           27

<210> SEQ ID NO 19
<211> LENGTH: 27
<212> TYPE: DNA
<213> ORGANISM: Homo sapiens

<400> SEQUENCE: 19
tttctaccat gtattgctaa acaaagt                                           27

<210> SEQ ID NO 20
<211> LENGTH: 27
<212> TYPE: DNA
<213> ORGANISM: Homo sapiens

<400> SEQUENCE: 20
tttagtatca attcacacca gcaagtt                                           27

<210> SEQ ID NO 21
<211> LENGTH: 27
<212> TYPE: DNA
<213> ORGANISM: Homo sapiens

<400> SEQUENCE: 21
ataatcgcca ctttacagag gagtaaa                                           27

<210> SEQ ID NO 22
<211> LENGTH: 27
<212> TYPE: DNA
<213> ORGANISM: Homo sapiens

<400> SEQUENCE: 22
tttctttaaa atgaagattt tccacca                                           27

<210> SEQ ID NO 23
<211> LENGTH: 27
<212> TYPE: DNA
<213> ORGANISM: Homo sapiens

<400> SEQUENCE: 23
tttaaaatga agattttcca ccaatca                                           27

<210> SEQ ID NO 24
<211> LENGTH: 27
<212> TYPE: DNA
<213> ORGANISM: Homo sapiens

<400> SEQUENCE: 24
ttttccacca atcactttac tctccta                                           27
```

```
<210> SEQ ID NO 25
<211> LENGTH: 27
<212> TYPE: DNA
<213> ORGANISM: Homo sapiens

<400> SEQUENCE: 25
tttcccacca gttcttaggc aactgtt                                        27

<210> SEQ ID NO 26
<211> LENGTH: 27
<212> TYPE: DNA
<213> ORGANISM: Homo sapiens

<400> SEQUENCE: 26
ataatcaagg atataaatta atgcaaa                                        27

<210> SEQ ID NO 27
<211> LENGTH: 27
<212> TYPE: DNA
<213> ORGANISM: Homo sapiens

<400> SEQUENCE: 27
ttttgttgtt gttgttaagg tcaaagt                                        27

<210> SEQ ID NO 28
<211> LENGTH: 27
<212> TYPE: DNA
<213> ORGANISM: Homo sapiens

<400> SEQUENCE: 28
tttaaaatta ccctagatct taaagtt                                        27

<210> SEQ ID NO 29
<211> LENGTH: 28
<212> TYPE: DNA
<213> ORGANISM: Homo sapiens

<400> SEQUENCE: 29
cacgccccca ccctaatcag aggccaaa                                       28

<210> SEQ ID NO 30
<211> LENGTH: 28
<212> TYPE: DNA
<213> ORGANISM: Homo sapiens

<400> SEQUENCE: 30
ccaaacccct tcctggagcct gtgataaa                                      28

<210> SEQ ID NO 31
<211> LENGTH: 28
<212> TYPE: DNA
<213> ORGANISM: Homo sapiens

<400> SEQUENCE: 31
ccttccgaaa gaggccccccc tgggcaaa                                      28

<210> SEQ ID NO 32
<211> LENGTH: 28
<212> TYPE: DNA
<213> ORGANISM: Homo sapiens

<400> SEQUENCE: 32
tctccatcac caagagagcc ttccgaaa                                       28
```

<210> SEQ ID NO 33
<211> LENGTH: 28
<212> TYPE: DNA
<213> ORGANISM: Homo sapiens

<400> SEQUENCE: 33
tgttagcttg cactagacta gcttcaaa                                          28

<210> SEQ ID NO 34
<211> LENGTH: 28
<212> TYPE: DNA
<213> ORGANISM: Homo sapiens

<400> SEQUENCE: 34
ttttctggcc tatgttatta cctgtatg                                          28

<210> SEQ ID NO 35
<211> LENGTH: 28
<212> TYPE: DNA
<213> ORGANISM: Homo sapiens

<400> SEQUENCE: 35
tttctggcct atgttattac ctgtatgg                                          28

<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
caaaaaccca aaatatttta gct                                               23

<210> SEQ ID NO 37
<211> LENGTH: 23
<212> TYPE: DNA
<213> ORGANISM: Artificial Sequence
<220> FEATURE:
<223> OTHER INFORMATION: Synthetic

<400> SEQUENCE: 37 ccttttggt atcttacagg aac                                                23

<210> SEQ ID NO 38
<211> LENGTH: 23
<212> TYPE: DNA
<213> ORGANISM: Artificial Sequence
<220> FEATURE:
<223> OTHER INFORMATION: Synthetic

<400> SEQUENCE: 38
ccgctgccca atgccatcct gga                                               23

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
tttttccttt tattctagtt gaa                                               23

```
<210> SEQ ID NO 40
<211> LENGTH: 23
<212> TYPE: DNA
<213> ORGANISM: Artificial Sequence
<220> FEATURE:
<223> OTHER INFORMATION: Synthetic

<400> SEQUENCE: 40
ttgatccata tgcttttacc tgc                                              23

<210> SEQ ID NO 41
<211> LENGTH: 23
<212> TYPE: DNA
<213> ORGANISM: Artificial Sequence
<220> FEATURE:
<223> OTHER INFORMATION: Synthetic

<400> SEQUENCE: 41
tcaacagatc tgtcaaatcg cct                                              23

<210> SEQ ID NO 42
<211> LENGTH: 23
<212> TYPE: DNA
<213> ORGANISM: Artificial Sequence
<220> FEATURE:
<223> OTHER INFORMATION: Synthetic

<400> SEQUENCE: 42
ttcttctttc tccaggctag aag                                              23

<210> SEQ ID NO 43
<211> LENGTH: 23
<212> TYPE: DNA
<213> ORGANISM: Artificial Sequence
<220> FEATURE:
<223> OTHER INFORMATION: Synthetic

<400> SEQUENCE: 43
gttcttctag cctggagaaa gaa                                              23

<210> SEQ ID NO 44
<211> LENGTH: 23
<212> TYPE: DNA
<213> ORGANISM: Artificial Sequence
<220> FEATURE:
<223> OTHER INFORMATION: Synthetic

<400> SEQUENCE: 44
caaatcctgc attgttgcct gta                                              23

<210> SEQ ID NO 45
<211> LENGTH: 23
<212> TYPE: DNA
<213> ORGANISM: Artificial Sequence
<220> FEATURE:
<223> OTHER INFORMATION: Synthetic

<400> SEQUENCE: 45
ctgttaaaga ggaagttaga aga                                              23

<210> SEQ ID NO 46
<211> LENGTH: 23
<212> TYPE: DNA
<213> ORGANISM: Artificial Sequence
<220> FEATURE:
<223> OTHER INFORMATION: Synthetic
```

<400> SEQUENCE: 46
aaaattttta tattacagaa tat                                          23

<210> SEQ ID NO 47
<211> LENGTH: 23
<212> TYPE: DNA
<213> ORGANISM: Artificial Sequence
<220> FEATURE:
<223> OTHER INFORMATION: Synthetic

<400> SEQUENCE: 47
ttgtagacta tcttttatat tct                                          23

<210> SEQ ID NO 48
<211> LENGTH: 23
<212> TYPE: DNA
<213> ORGANISM: Artificial Sequence
<220> FEATURE:
<223> OTHER INFORMATION: Synthetic

<400> SEQUENCE: 48
ttttgcattt tagatgaaag aga                                          23

<210> SEQ ID NO 49
<211> LENGTH: 23
<212> TYPE: DNA
<213> ORGANISM: Artificial Sequence
<220> FEATURE:
<223> OTHER INFORMATION: Synthetic

<400> SEQUENCE: 49
aacatcttct ctttcatcta aaa                                          23

<210> SEQ ID NO 50
<211> LENGTH: 23
<212> TYPE: DNA
<213> ORGANISM: Artificial Sequence
<220> FEATURE:
<223> OTHER INFORMATION: Synthetic

<400> SEQUENCE: 50
ttttgaacat cttctctttc atc                                          23

<210> SEQ ID NO 51
<211> LENGTH: 23
<212> TYPE: DNA
<213> ORGANISM: Artificial Sequence
<220> FEATURE:
<223> OTHER INFORMATION: Synthetic

<400> SEQUENCE: 51
caaaaaccca aaatatttta gct                                          23

<210> SEQ ID NO 52
<211> LENGTH: 23
<212> TYPE: DNA
<213> ORGANISM: Artificial Sequence
<220> FEATURE:
<223> OTHER INFORMATION: Synthetic

<400> SEQUENCE: 52
gcttgtgttt ctaattttc ttt                                           23

<210> SEQ ID NO 53
<211> LENGTH: 23

```
<212> TYPE: DNA
<213> ORGANISM: Artificial Sequence
<220> FEATURE:
<223> OTHER INFORMATION: Synthetic

<400> SEQUENCE: 53
acttattgtt attgaaattg gct                                              23

<210> SEQ ID NO 54
<211> LENGTH: 23
<212> TYPE: DNA
<213> ORGANISM: Artificial Sequence
<220> FEATURE:
<223> OTHER INFORMATION: Synthetic

<400> SEQUENCE: 54
taccatgtat tgctaaacaa agt                                              23

<210> SEQ ID NO 55
<211> LENGTH: 23
<212> TYPE: DNA
<213> ORGANISM: Artificial Sequence
<220> FEATURE:
<223> OTHER INFORMATION: Synthetic

<400> SEQUENCE: 55
gtatcaattc acaccagcaa gtt                                              23

<210> SEQ ID NO 56
<211> LENGTH: 23
<212> TYPE: DNA
<213> ORGANISM: Artificial Sequence
<220> FEATURE:
<223> OTHER INFORMATION: Synthetic

<400> SEQUENCE: 56
ctcctctgta aagtggcgat tat                                              23

<210> SEQ ID NO 57
<211> LENGTH: 23
<212> TYPE: DNA
<213> ORGANISM: Artificial Sequence
<220> FEATURE:
<223> OTHER INFORMATION: Synthetic

<400> SEQUENCE: 57
tttaaaatga agattttcca cca                                              23

<210> SEQ ID NO 58
<211> LENGTH: 23
<212> TYPE: DNA
<213> ORGANISM: Artificial Sequence
<220> FEATURE:
<223> OTHER INFORMATION: Synthetic

<400> SEQUENCE: 58
aaatgaagat tttccaccaa tca                                              23

<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
```
ccaccaatca ctttactctc cta                                              23

<210> SEQ ID NO 60
<211> LENGTH: 23
<212> TYPE: DNA
<213> ORGANISM: Artificial Sequence
<220> FEATURE:
<223> OTHER INFORMATION: Synthetic

<400> SEQUENCE: 60
ccaccagttc ttaggcaact gtt                                              23

<210> SEQ ID NO 61
<211> LENGTH: 23
<212> TYPE: DNA
<213> ORGANISM: Artificial Sequence
<220> FEATURE:
<223> OTHER INFORMATION: Synthetic

<400> SEQUENCE: 61
cattaattta tatccttgat tat                                              23

<210> SEQ ID NO 62
<211> LENGTH: 23
<212> TYPE: DNA
<213> ORGANISM: Artificial Sequence
<220> FEATURE:
<223> OTHER INFORMATION: Synthetic

<400> SEQUENCE: 62
gttgttgttg ttaaggtcaa agt                                              23

<210> SEQ ID NO 63
<211> LENGTH: 23
<212> TYPE: DNA
<213> ORGANISM: Artificial Sequence
<220> FEATURE:
<223> OTHER INFORMATION: Synthetic

<400> SEQUENCE: 63
aaattaccct agatcttaaa gtt                                              23

<210> SEQ ID NO 64
<211> LENGTH: 24
<212> TYPE: DNA
<213> ORGANISM: Artificial Sequence
<220> FEATURE:
<223> OTHER INFORMATION: Synthetic

<400> SEQUENCE: 64
gcctctgatt agggtggggg cgtg                                             24

<210> SEQ ID NO 65
<211> LENGTH: 24
<212> TYPE: DNA
<213> ORGANISM: Artificial Sequence
<220> FEATURE:
<223> OTHER INFORMATION: Synthetic

<400> SEQUENCE: 65
tcacaggctc caggaagggt ttgg                                             24

<210> SEQ ID NO 66
<211> LENGTH: 24
<212> TYPE: DNA
<213> ORGANISM: Artificial Sequence

```
<220> FEATURE:
<223> OTHER INFORMATION: Synthetic

<400> SEQUENCE: 66 cccaggggg cctctttcgg aagg                                          24

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggaaggctct cttggtgatg gaga                                         24

<210> SEQ ID NO 68
<211> LENGTH: 24
<212> TYPE: DNA
<213> ORGANISM: Artificial Sequence
<220> FEATURE:
<223> OTHER INFORMATION: Synthetic

<400> SEQUENCE: 68
aagctagtct agtgcaagct aaca                                         24

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
ctggcctatg ttattacctg tatg                                         24

<210> SEQ ID NO 70
<211> LENGTH: 24
<212> TYPE: DNA
<213> ORGANISM: Artificial Sequence
<220> FEATURE:
<223> OTHER INFORMATION: Synthetic

<400> SEQUENCE: 70
tggcctatgt tattacctgt atgg                                         24

<210> SEQ ID NO 71
<211> LENGTH: 23
<212> TYPE: DNA
<213> ORGANISM: Artificial Sequence
<220> FEATURE:
<223> OTHER INFORMATION: Synthetic

<400> SEQUENCE: 71
ttccattcta atgggtggct gtt                                          23

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
ctcctctgta aagtggcgat                                              20
```

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
ttccattcta atgggtggct                                               20

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
gtatcaattc acaccagcaa                                               20

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
taccatgtat tgctaaacaa                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
acttattgtt attgaaattg                                               20

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
gcttgtgttt ctaattttc                                                20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
caaaaaccca aaatatttta                                               20

<210> SEQ ID NO 79
<211> LENGTH: 20
<212> TYPE: DNA
<213> ORGANISM: Artificial Sequence
<220> FEATURE:
<223> OTHER INFORMATION: Synthetic

```
<400> SEQUENCE: 79
tttaaaatga agattttcca                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
aaatgaagat tttccaccaa                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
ccaccaatca ctttactctc                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
ccaccagttc ttaggcaact                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
cattaattta tatccttgat                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
agttatagct ctctttcaat                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
atgtataaca attccaacat                                               20

<210> SEQ ID NO 86
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 86
aaattaccct agatcttaaa                                              20

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
gttgttgttg ttaaggtcaa                                              20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
gcttgtgttt ctaattttc                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89 taattttct ttttcttctt                                               20

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
gcaaaaagga aaaagaaga                                               20

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
gggtttttgc aaaaaggaaa                                              20

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
```
agctcctact cagactgtta                                              20

<210> SEQ ID NO 93
<211> LENGTH: 20
<212> TYPE: DNA
<213> ORGANISM: Artificial Sequence
<220> FEATURE:
<223> OTHER INFORMATION: Synthetic

<400> SEQUENCE: 93
tgcaaaaacc caaatatttt                                              20

<210> SEQ ID NO 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
tgtcaccaga gtaacagtct                                              20

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
cttagtaacc acaggttgtg                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic

<400> SEQUENCE: 96
tagtttggag atggcagttt                                              20

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
gagatggcag tttccttagt                                              20

<210> SEQ ID NO 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
cttgatgttg gaggtacctg                                              20

<210> SEQ ID NO 99
<211> LENGTH: 20
<212> TYPE: DNA

```
<213> ORGANISM: Artificial Sequence
<220> FEATURE:
<223> OTHER INFORMATION: Synthetic

<400> SEQUENCE: 99
atgttggagg tacctgctct                                                 20

<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
taacttgatc aagcagagaa                                                 20

<210> SEQ ID NO 101
<211> LENGTH: 20
<212> TYPE: DNA
<213> ORGANISM: Artificial Sequence
<220> FEATURE:
<223> OTHER INFORMATION: Synthetic

<400> SEQUENCE: 101
tctgcttgat caagttataa                                                 20

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
taaaatcaca gagggtgatg                                                 20

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
atatcctcaa ggtcacccac                                                 20

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104
atgatcatct cgttgatatc                                                 20

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105 tcatacctt c tgcttgatga                                                20
```

<210> SEQ ID NO 106
<211> LENGTH: 20
<212> TYPE: DNA
<213> ORGANISM: Artificial Sequence
<220> FEATURE:
<223> OTHER INFORMATION: Synthetic

<400> SEQUENCE: 106 tcatttttc tcataccttc                                                    20

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
tgccaacttt tatcattttt                                                   20

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
aatcagaaag aagatcttat                                                   20

<210> SEQ ID NO 109
<211> LENGTH: 20
<212> TYPE: DNA
<213> ORGANISM: Artificial Sequence
<220> FEATURE:
<223> OTHER INFORMATION: Synthetic

<400> SEQUENCE: 109
atttccctag ggtccagctt                                                   20

<210> SEQ ID NO 110
<211> LENGTH: 20
<212> TYPE: DNA
<213> ORGANISM: Artificial Sequence
<220> FEATURE:
<223> OTHER INFORMATION: Synthetic

<400> SEQUENCE: 110
gctcaaattg ttactcttca                                                   20

<210> SEQ ID NO 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
agctcctact cagactgtta                                                   20

<210> SEQ ID NO 112
<211> LENGTH: 20
<212> TYPE: DNA
<213> ORGANISM: Artificial Sequence
<220> FEATURE:

<223> OTHER INFORMATION: Synthetic

<400> SEQUENCE: 112
attctagtac tatgcatctt                                               20

<210> SEQ ID NO 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
acttaagtta cttgtccagg                                               20

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
ccaaggtccc agagttccta                                               20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
tttccctggc aaggtctgaa                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
gctcattctc atgcctggac                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
tttagcaata catggtagaa                                               20

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118
agccaaactc ttattcatga                                               20

```
<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
taacaatgtg gatactttgt                                                   20

<210> SEQ ID NO 120
<211> LENGTH: 4
<212> TYPE: DNA
<213> ORGANISM: Artificial Sequence
<220> FEATURE:
<223> OTHER INFORMATION: Synthetic

<400> SEQUENCE: 120 ttta                                                                     4

<210> SEQ ID NO 121
<211> LENGTH: 4
<212> TYPE: DNA
<213> ORGANISM: Artificial Sequence
<220> FEATURE:
<223> OTHER INFORMATION: Synthetic

<400> SEQUENCE: 121 tttg                                                                     4

<210> SEQ ID NO 122
<211> LENGTH: 4
<212> TYPE: DNA
<213> ORGANISM: Artificial Sequence
<220> FEATURE:
<223> OTHER INFORMATION: Synthetic

<400> SEQUENCE: 122 tttc                                                                     4

<210> SEQ ID NO 123
<211> LENGTH: 4
<212> TYPE: DNA
<213> ORGANISM: Artificial Sequence
<220> FEATURE:
<223> OTHER INFORMATION: Synthetic

<400> SEQUENCE: 123 tttt                                                                     4

<210> SEQ ID NO 124
<211> LENGTH: 9464
<212> TYPE: DNA
<213> ORGANISM: Artificial Sequence
<220> FEATURE:
<223> OTHER INFORMATION: Synthetic AsCpf1

<400> SEQUENCE: 124
gacggatcgg gagatctccc gatcccctat ggtgcactct cagtacaatc tgctctgatg        60
ccgcatagtt aagccagtat ctgctccctg cttgtgtgtt ggaggtcgct gagtagtgcg       120
cgagcaaaat ttaagctaca acaaggcaag gcttgaccga caattgcatg aagaatctgc       180
ttagggttag gcgttttgcg ctgcttcgcg atgtacgggc cagatatacg cgttgacatt       240
gattattgac tagttattaa tagtaatcaa ttacggggtc attagttcat agcccatata       300
```

```
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgccaccat gacacagttc gagggcttta ccaacctgta    960
tcaggtgagc aagacactgc ggtttgagct gatcccacag ggcaagaccc tgaagcacat   1020
ccaggagcag ggcttcatcg aggaggacaa ggcccgcaat gatcactaca aggagctgaa   1080
gcccatcatc gatcggatct acaagaccta tgccgaccag tgcctgcagc tggtgcagct   1140
ggattgggag aacctgagcg ccgccatcga ctcctataga aaggagaaaa ccgaggagac   1200
aaggaacgcc ctgatcgagg agcaggccac atatcgcaat gccatccacg actacttcat   1260
cggccggaca gacaacctga ccgatgccat caataagaga cacgccgaga tctacaaggg   1320
cctgttcaag gccgagctgt ttaatggcaa ggtgctgaag cagctgggca ccgtgaccac   1380
aaccgagcac gagaacgccc tgctgcggag cttcgacaag tttacaacct acttctccgg   1440
cttttatgag aacaggaaga acgtgttcag cgccgaggat atcagcacag ccatcccaca   1500
ccgcatcgtg caggacaact tccccaagtt taaggagaat tgtcacatct tcacacgcct   1560
gatcaccgcc gtgcccagcc tgcgggagca ctttgagaac gtgaagaagg ccatcggcat   1620
cttcgtgagc acctccatcg aggaggtgtt ttccttccct tttataaacc agctgctgac   1680
acagacccag atcgacctgt ataaccagct gctgggagga atctctcggg aggcaggcac   1740
cgagaagatc aagggcctga cgaggtgctg aatctggcc atccagaaga atgatgagac   1800
agcccacatc atcgcctccc tgccacacag attcatcccc ctgtttaagc agatcctgtc   1860
cgataggaac accctgtctt tcatcctgga ggagtttaag agcgacgagg aagtgatcca   1920
gtccttctgc aagtacaaga cactgctgag aaacgagaac gtgctggaga cagccgaggc   1980
cctgtttaac gagctgaaca gcatcgacct gacacacatc ttcatcagcc acaagaagct   2040
ggagacaatc agcagcgccc tgtgcgacca ctgggataca ctgaggaatg ccctgtatga   2100
gcggagaatc tccgagctga caggcaagat caccaagtct gccaaggaga aggtgcagcg   2160
cagcctgaag cacgaggata tcaacctgca ggagatcatc tctgccgcag gcaaggagct   2220
gagcgaggcc ttcaagcaga aaaccagcga gatcctgtcc cacgcacacg ccgccctgga   2280
tcagccactg cctacaaccc tgaagaagca ggaggagaag gagatcctga agtctcagct   2340
ggacagcctg ctgggcctgt accacctgct ggactggttt gccgtggatg agtccaacga   2400
ggtggacccc gagttctctg cccggctgac cggcatcaag ctggagatgg agccttctct   2460
gagcttctac aacaaggcca gaattatgc caccaagaag ccctactccg tggagaagtt   2520
caagctgaac tttcagatgc ctacactggc ctctggctgg gacgtgaata aggagaagaa   2580
caatggcgcc atcctgtttg tgaagaacgg cctgtactat ctgggcatca tgccaaagca   2640
gaagggcagg tataaggccc tgagcttcga gcccacagag aaaaccagcg agggctttga   2700
```

| | |
|---|---|
| taagatgtac tatgactact tccctgatgc cgccaagatg atcccaaagt gcagcaccca | 2760 |
| gctgaaggcc gtgacagccc actttcagac ccacacaacc cccatcctgc tgtccaacaa | 2820 |
| tttcatcgag cctctggaga tcacaaagga gatctacgac ctgaacaatc ctgagaagga | 2880 |
| gccaaagaag tttcagacag cctacgccaa gaaaaccggc gaccagaagg ctacagaga | 2940 |
| ggccctgtgc aagtggatcg acttcacaag ggattttctg tccaagtata ccaagacaac | 3000 |
| ctctatcgat ctgtctagcc tgcggccatc ctctcagtat aaggacctgg gcgagtacta | 3060 |
| tgccgagctg aatcccctgc tgtaccacat cagcttccag agaatcgccg agaaggagat | 3120 |
| catggatgcc gtggagacag gcaagctgta cctgttccag atctataaca aggactttgc | 3180 |
| caagggccac cacggcaagc ctaatctgca cactgtatat ggaccggcc tgttttctcc | 3240 |
| agagaacctg gccaagacaa gcatcaagct gaatggccag gccgagctgt ctaccgccc | 3300 |
| taagtccagg atgaagagga tggcacaccg gctgggagag aagatgctga caagaagct | 3360 |
| gaaggatcag aaaaccccaa tccccgacac cctgtaccag gagctgtacg actatgtgaa | 3420 |
| tcacagactg tcccacgacc tgtctgatga ggccagggcc ctgctgccca cgtgatcac | 3480 |
| caaggaggtg tctcacgaga tcatcaagga taggcgcttt accagcgaca gttcttttt | 3540 |
| ccacgtgcct atcacactga actatcaggc cgccaattcc ccatctaagt tcaaccagag | 3600 |
| ggtgaatgcc tacctgaagg agcaccccga gacacctatc atcggcatcg atcgggcga | 3660 |
| gagaaacctg atctatatca cagtgatcga ctccaccggc aagatcctgg agcagcggag | 3720 |
| cctgaacacc atccagcagt ttgattacca gaagaagctg gacaacaggg agaaggagag | 3780 |
| ggtggcagca aggcaggcct ggtctgtggt gggcacaatc aaggatctga gcagggcta | 3840 |
| tctgagccag gtcatccacg agatcgtgga cctgatgatc cactaccagg ccgtggtggt | 3900 |
| gctggagaac ctgaatttcg cctttaagag caagaggacc ggcatcgccg agaaggccgt | 3960 |
| gtaccagcag ttcgagaaga tgctgatcga taagctgaat tgcctggtgc tgaaggacta | 4020 |
| tccagcagag aaagtgggag cgtgctgaa cccataccag ctgacagacc agttcacctc | 4080 |
| ctttgccaag atgggcaccc agtctggctt cctgttttac gtgcctgccc catatacatc | 4140 |
| taagatcgat cccctgaccg gcttcgtgga ccccttcgtg tggaaaacca tcaagaatca | 4200 |
| cgagagccgc aagcacttcc tggagggctt cgactttctg cactacgacg tgaaaaccgg | 4260 |
| cgacttcatc ctgcacttta agatgaacag aaatctgtcc ttccagaggg gcctgcccgg | 4320 |
| cttttatgcct gcatgggata tcgtgttcga gaagaacgag acacagtttg acgccaaggg | 4380 |
| caccccttc atcgccggca agagaatcgt gccagtgatc gagaatcaca gattcaccgg | 4440 |
| cagatacccgg gacctgtatc ctgccaacga gctgatcgcc ctgctggagg agaagggcat | 4500 |
| cgtgttcagg gatggctcca acatcctgcc aaagctgctg gagaatgacg attctcacgc | 4560 |
| catcgacacc atggtggccc tgatccgcag cgtgctgcag atgcggaact ccaatgccgc | 4620 |
| cacaggcgag gactatatca cagcccccgt gcgcgatctg aatggcgtgt gcttcgactc | 4680 |
| ccggtttcag aacccagagt ggcccatgga cgccgatgcc aatggcgcct accacatcgc | 4740 |
| cctgaagggc cagctgctgc tgaatcacct gaaggagagc aaggatctga gctgcagaa | 4800 |
| cggcatctcc aatcaggact ggctggccta catccaggag ctgcgcaaca aaaggccggc | 4860 |
| ggccacgaaa aaggccggcc aggcaaaaaa gaaaaaggga tcctacccat acgatgttcc | 4920 |
| agattacgct tatccctacg acgtgcctga ttatgcatac ccatatgatg tccccgacta | 4980 |
| tgcctaagaa ttctgcagat atccagcaca gtggcggccg ctcgagtcta gagggcccgt | 5040 |

```
ttaaacccgc tgatcagcct cgactgtgcc ttctagttgc cagccatctg ttgtttgccc    5100
ctcccccgtg ccttccttga ccctggaagg tgccactccc actgtccttt cctaataaaa    5160
tgaggaaatt gcatcgcatt gtctgagtag gtgtcattct attctggggg gtggggtggg    5220
gcaggacagc aaggggagg attgggaaga caatagcagg catgctgggg atgcggtggg     5280
ctctatggct tctgaggcgg aaagaaccag ctggggctct aggggtatc cccacgcgcc     5340
ctgtagcggc gcattaagcg cggcgggtgt ggtggttacg cgcagcgtga ccgctacact    5400
tgccagcgcc ctagcgcccg ctcctttcgc tttcttccct tcctttctcg ccacgttcgc    5460
cggcttccc cgtcaagctc taaatcgggg gctccctta gggttccgat ttagtgcttt      5520
acggcacctc gaccccaaaa aacttgatta gggtgatggt tcacgtagtg ggccatcgcc    5580
ctgatagacg gttttcgcc ctttgacgtt ggagtccacg ttctttaata gtggactctt     5640
gttccaaact ggaacaacac tcaaccctat ctcggtctat tcttttgatt tataagggat    5700
tttgccgatt tcggcctatt ggttaaaaaa tgagctgatt taacaaaaat ttaacgcgaa    5760
ttaattctgt ggaatgtgtg tcagttaggg tgtggaaagt ccccaggctc cccagcaggc    5820
agaagtatgc aaagcatgca tctcaattag tcagcaacca ggtgtggaaa gtccccaggc    5880
tccccagcag gcagaagtat gcaaagcatg catctcaatt agtcagcaac catagtcccg    5940
cccctaactc cgcccatccc gcccctaact ccgcccagtt ccgcccattc tccgccccat    6000
ggctgactaa ttttttttat ttatgcagag gccgaggccg cctctgcctc tgagctattc    6060
cagaagtagt gaggaggctt ttttggaggc ctaggctttt gcaaaaagct cccgggagct    6120
tgtatatcca ttttcggatc tgatcaagag acaggatgag gatcgtttcg catgattgaa    6180
caagatggat tgcacgcagg ttctccggcc gcttgggtgg agaggctatt cggctatgac    6240
tgggcacaac agacaatcgg ctgctctgat gccgccgtgt tccggctgtc agcgcagggg    6300
cgcccggttc tttttgtcaa gaccgacctg tccggtgccc tgaatgaact gcaggacgag    6360
gcagcgcggc tatcgtggct ggccacgacg ggcgttcctt gcgcagctgt gctcgacgtt    6420
gtcactgaag cgggaaggga ctggctgcta ttgggcgaag tgccggggca ggatctcctg    6480
tcatctcacc ttgctcctgc cgagaaagta tccatcatgg ctgatgcaat gcggcggctg    6540
catacgcttg atccggctac ctgcccattc gaccaccaag cgaaacatcg catcgagcga    6600
gcacgtactc ggatggaagc cggtcttgtc gatcaggatg atctggacga agagcatcag    6660
gggctcgcgc cagccgaact gttcgccagg ctcaaggcgc gcatgcccga cggcgaggat    6720
ctcgtcgtga cccatggcga tgcctgcttg ccgaatatca tggtggaaaa tggccgcttt    6780
tctggattca tcgactgtgg ccggctgggt gtggcggacc gctatcagga catagcgttg    6840
gctacccgtg atattgctga agagcttggc ggcgaatggg ctgaccgctt cctcgtgctt    6900
tacggtatcg ccgctcccga ttcgcagcgc atcgccttct atcgccttct tgacgagttc    6960
ttctgagcgg gactctgggg ttcgaaatga ccgaccaagc gacgcccaac ctgccatcac    7020
gagatttcga ttccaccgcc gccttctatg aaaggttggg cttcggaatc gttttccggg    7080
acgccggctg gatgatcctc cagcgcgggg atctcatgct ggagttcttc gcccacccca    7140
acttgtttat tgcagcttat aatggttaca aataaagcaa tagcatcaca aatttcacaa    7200
ataaagcatt tttttcactg cattctagtt gtggtttgtc caaactcatc aatgtatctt    7260
atcatgtctg tataccgtcg acctctagct agagcttggc gtaatcatgg tcatagctgt    7320
ttcctgtgtg aaattgttat ccgctcacaa ttccacacaa catacgagcc ggaagcataa    7380
agtgtaaagc ctggggtgcc taatgagtga gctaactcac attaattgcg ttgcgctcac    7440
```

```
tgcccgcttt ccagtcggga aacctgtcgt gccagctgca ttaatgaatc ggccaacgcg    7500
cggggagagg cggtttgcgt attgggcgct cttccgcttc ctcgctcact gactcgctgc    7560
gctcggtcgt tcggctgcgg cgagcggtat cagctcactc aaaggcggta atacggttat    7620
ccacagaatc aggggataac gcaggaaaga acatgtgagc aaaaggccag caaaaggcca    7680
ggaaccgtaa aaaggccgcg ttgctggcgt ttttccatag gctccgcccc cctgacgagc    7740
atcacaaaaa tcgacgctca agtcagaggt ggcgaaaccc gacaggacta taaagatacc    7800
aggcgtttcc ccctggaagc tccctcgtgc gctctcctgt tccgaccctg ccgcttaccg    7860
gatacctgtc cgcctttctc ccttcgggaa gcgtggcgct ttctcatagc tcacgctgta    7920
ggtatctcag ttcggtgtag gtcgttcgct ccaagctggg ctgtgtgcac gaaccccccg    7980
ttcagcccga ccgctgcgcc ttatccggta actatcgtct tgagtccaac ccggtaagac    8040
acgacttatc gccactggca gcagccactg gtaacaggat tagcagagcg aggtatgtag    8100
gcggtgctac agagttcttg aagtggtggc ctaactacgg ctacactaga agaacagtat    8160
ttggtatctg cgctctgctg aagccagtta ccttcggaaa aagagttggt agctcttgat    8220
ccggcaaaca aaccaccgct ggtagcggtt tttttgtttg caagcagcag attacgcgca    8280
gaaaaaaagg atctcaagaa gatcctttga tcttttctac ggggtctgac gctcagtgga    8340
acgaaaactc acgttaaggg attttggtca tgagattatc aaaaaggatc ttcacctaga    8400
tccttttaaa ttaaaaatga agttttaaat caatctaaag tatatatgag taaacttggt    8460
ctgacagtta ccaatgctta atcagtgagg cacctatctc agcgatctgt ctatttcgtt    8520
catccatagt tgcctgactc cccgtcgtgt agataactac gatacgggag ggcttaccat    8580
ctggccccag tgctgcaatg ataccgcgag acccacgctc accggctcca gatttatcag    8640
caataaacca gccagccgga agggccgagc gcagaagtgg tcctgcaact ttatccgcct    8700
ccatccagtc tattaattgt tgccgggaag ctagagtaag tagttcgcca gttaatagtt    8760
tgcgcaacgt tgttgccatt gctacaggca tcgtggtgtc acgctcgtcg tttggtatgg    8820
cttcattcag ctccggttcc caacgatcaa ggcgagttac atgatccccc atgttgtgca    8880
aaaaagcggt tagctccttc ggtcctccga tcgttgtcag aagtaagttg gccgcagtgt    8940
tatcactcat ggttatggca gcactgcata attctcttac tgtcatgcca tccgtaagat    9000
gcttttctgt gactggtgag tactcaacca agtcattctg agaatagtgt atgcggcgac    9060
cgagttgctc ttgcccggcg tcaatacggg ataataccgc gccacatagc agaactttaa    9120
aagtgctcat cattggaaaa cgttcttcgg ggcgaaaact ctcaaggatc ttaccgctgt    9180
tgagatccag ttcgatgtaa cccactcgtg cacccaactg atcttcagca tcttttactt    9240
tcaccagcgt ttctgggtga gcaaaaacag gaaggcaaaa tgccgcaaaa aagggaataa    9300
gggcgacacg gaaatgttga atactcatac tcttcctttt tcaatattat tgaagcattt    9360
atcagggtta ttgtctcatg agcggataca tatttgaatg tatttagaaa aataaacaaa    9420 tagggggttcc gcgcacattt ccccgaaaag tgccacctga cgtc                   9464
```

<210> SEQ ID NO 125
<211> LENGTH: 9227
<212> TYPE: DNA
<213> ORGANISM: Artificial Sequence
<220> FEATURE:
<223> OTHER INFORMATION: Synthetic LbCpf1

<400> SEQUENCE: 125

```
gacggatcgg gagatctccc gatccccdat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggta ccgccaccat gagcaagctg gagaagttta caaactgcta   960
ctccctgtct aagaccctga ggttcaaggc catccctgtg gcaagaccc aggagaacat  1020 cgacaataag cggctgctgg tggaggacga aagagagcc gaggattata agggcgtgaa  1080
gaagctgctg gatcgctact atctgtcttt tatcaacgac gtgctgcaca gcatcaagct  1140
gaagaatctg aacaattaca tcagcctgtt ccggaagaaa accagaaccg agaaggagaa  1200
taaggagctg gagaacctgg agatcaatct gcggaaggga atcgccaagg ccttcaaggg  1260
caacgagggc tacaagtccc tgtttaagaa ggatatcatc gagacaatcc tgccagagtt  1320
cctggacgat aaggacgaga tcgccctggt gaacagcttc aatggcttta ccacagcctt  1380
caccggcttc tttgataaca gagagaatat gttttccgag gaggccaaga gcacatccat  1440
cgccttcagg tgtatcaacg agaatctgac ccgctacatc tctaatatgg acatcttcga  1500
gaaggtggac gccatctttg ataagcacga ggtgcaggag atcaaggaga agatcctgaa  1560
cagcgactat gatgtggagg atttctttga gggcgagttc tttaactttg tgctgacaca  1620
ggagggcatc gacgtgtata acgccatcat cggcggcttc gtgaccgaga gcggcgagaa  1680
gatcaagggc ctgaacgagt acatcaacct gtataatcag aaaaccaagc agaagctgcc  1740
taagtttaag ccactgtata gcaggtgct gagcgatcgg gagtctctga gcttctacgg  1800
cgagggctat acatccgatg aggaggtgct ggaggtgttt agaaacaccc tgaacaagaa  1860
cagcgagatc ttcagctcca tcaagaagct ggagaagctg ttcaagaatt ttgacgagta  1920
ctctagcgcc ggcatctttg tgaagaacgg ccccgccatc agcacaatct ccaaggatat  1980
cttcggcgag tggaacgtga tccgggacaa gtggaatgcc gagtatgacg atatccacct  2040
gaagaagaag gccgtggtga ccgagaagta cgaggacgat cggagaaagt ccttcaagaa  2100
gatcggctcc ttttctctgg agcagctgca ggagtacgcc gacgccgatc tgtctgtggt  2160
ggagaagctg aaggagatca tcatccagaa ggtggatgag atctacaagg tgtatggctc  2220
ctctgagaag ctgttccacg ccgatttttt gctggagaag agcctgaaga agaacgacgc  2280
cgtggtggcc atcatgaagg acctgctgga ttctgtgaag agcttcgaga attacatcaa  2340
ggccttcttt ggcgagggca aggagacaaa cagggacgag tccttctatg cgattttgt  2400
```

```
gctggcctac gacatcctgc tgaaggtgga ccacatctac gatgccatcc gcaattatgt   2460
gacccagaag ccctactcta aggataagtt caagctgtat tttcagaacc ctcagttcat   2520
gggcggctgg gacaaggata aggagacaga ctatcgggcc accatcctga gatacggctc   2580
caagtactat ctggccatca tggataagaa gtacgccaag tgcctgcaga gatcgacaa    2640
ggacgatgtg aacggcaatt acgagaagat caactataag ctgctgcccg ccctaataa    2700
gatgctgcca aaggtgttct tttctaagaa gtggatggcc tactataacc ccagcgagga   2760
catccagaag atctacaaga atggcacatt caagaagggc gatatgttta acctgaatga   2820
ctgtcacaag ctgatcgact tctttaagga tagcatctcc cggtatccaa agtggtccaa   2880
tgcctacgat ttcaactttt ctgagacaga gaagtataag gacatcgccg cttttacag    2940
agaggtggag gagcagggct ataaggtgag cttcgagtct gccagcaaga aggaggtgga   3000
taagctggtg gaggagggca agctgtatat gttccagatc tataacaagg acttttccga   3060
taagtctcac ggcacaccca atctgcacac catgtacttc aagctgctgt ttgacgagaa   3120
caatcacgga cagatcaggc tgagcggagg agcagagctg ttcatgaggc gcgcctccct   3180
gaagaaggag gagctggtgg tgcacccagc caactcccct atcgccaaca gaatccaga    3240
taatcccaag aaaaccacaa ccctgtccta cgacgtgtat aaggataaga ggttttctga   3300
ggaccagtac gagctgcaca tcccaatcgc catcaataag tgcccaaga acatcttcaa    3360
gatcaataca gaggtgcgcg tgctgctgaa gcacgacgat aacccctatg tgatcggcat   3420
cgataggggc gagcgcaatc tgctgtatat cgtggtggtg gacggcaagg caacatcgt    3480
ggagcagtat tccctgaacg agatcatcaa caacttcaac ggcatcagga tcaagacaga   3540
ttaccactct ctgctggaca gaaggagaa ggagaggttc gaggcccgcc agaactggac    3600
ctccatcgag aatatcaagg agctgaaggc cggctatatc tctcaggtgg tgcacaagat   3660
ctgcgagctg gtggagaagt acgatgccgt gatcgccctg gaggacctga actctggctt   3720
taagaatagc cgcgtgaagg tggagaagca ggtgtatcag aagttcgaga gatgctgat    3780
cgataagctg aactacatgg tggacaagaa gtctaatcct tgtgcaacag gcggcgccct   3840
gaagggctat cagatcacca ataagttcga gagctttaag tccatgtcta cccagaacgg   3900
cttcatcttt tacatccctg cctggctgac atccaagatc gatccatcta ccggctttgt   3960
gaacctgctg aaaaccaagt ataccagcat cgccgattcc aagaagttca tcagctcctt   4020
tgacaggatc atgtacgtgc ccgaggagga tctgttcgag tttgccctgg actataagaa   4080
cttctctcgc acagacgccg attacatcaa gaagtggaag ctgtactcct acggcaaccg   4140
gatcagaatc ttccggaatc ctaagaagaa caacgtgttc gactgggagg aggtgtgcct   4200
gaccagcgcc tataaggagc tgttcaacaa gtacggcatc aattatcagc agggcgatat   4260
cagagccctg ctgtgcgagc agtccgacaa ggccttctac tctagctttta tggccctgat   4320
gagcctgatg ctgcagatgc ggaacagcat cacaggccgc accgacgtgg attttctgat   4380
cagccctgtg aagaactccg acggcatctt ctacgatagc cggaactatg aggcccagga   4440
gaatgccatc ctgccaaaga cgccgacgc caatggcgcc tataacatcg ccagaaaggt   4500
gctgtgggcc atcggccagt tcaagaaggc cgaggacaga agctggata aggtgaagat    4560
cgccatctct aacaaggagt ggctggagta cgcccagacc agcgtgaagc acaaaaggcc   4620
ggcgccacg aaaaaggccg gccaggcaaa aagaaaaag ggatcctacc catacgatgt    4680
tccagattac gcttatccct acgacgtgcc tgattatgca tacccatatg atgtccccga   4740
```

```
ctatgcctaa gaattctgca gatatccagc acagtggcgg ccgctcgagt ctagagggcc    4800
cgtttaaacc cgctgatcag cctcgactgt gccttctagt tgccagccat ctgttgtttg    4860
cccctccccc gtgccttcct tgaccctgga aggtgccact cccactgtcc tttcctaata    4920
aaatgaggaa attgcatcgc attgtctgag taggtgtcat tctattctgg ggggtggggt    4980
ggggcaggac agcaagggg aggattggga agacaatagc aggcatgctg gggatgcggt    5040
gggctctatg gcttctgagg cggaaagaac cagctgggc tctagggggt atccccacgc    5100
gccctgtagc ggcgcattaa gcgcggcggg tgtggtggtt acgcgcagcg tgaccgctac    5160
acttgccagc gccctagcgc ccgctccttt cgctttcttc ccttcctttc tcgccacgtt    5220
cgccggcttt ccccgtcaag ctctaaatcg ggggctccct ttagggttcc gatttagtgc    5280
tttacggcac ctcgacccca aaaaacttga ttagggtgat ggttcacgta gtgggccatc    5340
gccctgatag acgttttttc gccctttgac gttggagtcc acgttcttta atagtggact    5400
cttgttccaa actggaacaa cactcaaccc tatctcggtc tattcttttg atttataagg    5460
gattttgccg atttcggcct attggttaaa aaatgagctg atttaacaaa aatttaacgc    5520
gaattaattc tgtggaatgt gtgtcagtta gggtgtggaa agtccccagg ctccccagca    5580
ggcagaagta tgcaaagcat gcatctcaat tagtcagcaa ccaggtgtgg aaagtcccca    5640
ggctccccag caggcagaag tatgcaaagc atgcatctca attagtcagc aaccatagtc    5700 ccgccctaa ctccgcccat cccgcccta actccgccca gttccgccca ttctccgccc    5760
catggctgac taattttttt tatttatgca gaggccgagg ccgcctctgc ctctgagcta    5820
ttccagaagt agtgaggagg cttttttgga ggcctaggct tttgcaaaaa gctcccggga    5880
gcttgtatat ccattttcgg atctgatcaa gagacaggat gaggatcgtt tcgcatgatt    5940
gaacaagatg gattgcacgc aggttctccg gccgcttggg tggagaggct attcggctat    6000
gactgggcac aacagacaat cggctgctct gatgccgccg tgttccggct gtcagcgcag    6060
gggcgcccgg ttcttttgt caagaccgac ctgtccggtg ccctgaatga actgcaggac    6120
gaggcagcgc ggctatcgtg gctggccacg acgggcgttc cttgcgcagc tgtgctcgac    6180
gttgtcactg aagcgggaag ggactggctg ctattgggcg aagtgccggg gcaggatctc    6240
ctgtcatctc accttgctcc tgccgagaaa gtatccatca tggctgatgc aatgcggcgg    6300
ctgcatacgc ttgatccggc tacctgccca ttcgaccacc aagcgaaaca tcgcatcgag    6360
cgagcacgta ctcggatgga agccggtctt gtcgatcagg atgatctgga cgaagagcat    6420
caggggctcg cgccagccga actgttcgcc aggctcaagg cgcgcatgcc cgacggcgag    6480
gatctcgtcg tgacccatgg cgatgcctgc ttgccgaata tcatggtgga aaatggccgc    6540
ttttctggat tcatcgactg tggccggctg ggtgtggcgg accgctatca ggacatagcg    6600
ttggctaccc gtgatattgc tgaagagctt ggcggcgaat gggctgaccg cttcctcgtg    6660
ctttacggta tcgccgctcc cgattcgcag cgcatcgcct tctatcgcct tcttgacgag    6720
ttcttctgag cgggactctg ggggttcgaaa tgaccgacca agcgacgccc aacctgccat    6780
cacgagattt cgattccacc gccgccttct atgaaaggtt gggcttcgga atcgttttcc    6840
gggacgccgg ctgatgatc ctccagcgcg ggatctcat gctggagttc ttcgcccacc    6900
ccaacttgtt tattgcagct tataatggtt acaaataaag caatagcatc acaaatttca    6960
caaataaagc atttttttca ctgcattcta gttgtggttt gtccaaactc atcaatgtat    7020
cttatcatgt ctgtataccg tcgacctcta gctagagctt ggcgtaatca tggtcatagc    7080
tgtttcctgt gtgaaattgt tatccgctca caattccaca caacatacga gccggaagca    7140
```

```
taaagtgtaa agcctggggt gcctaatgag tgagctaact cacattaatt gcgttgcgct    7200
cactgcccgc tttccagtcg ggaaacctgt cgtgccagct gcattaatga atcggccaac    7260
gcgcggggag aggcggtttg cgtattgggc gctcttccgc ttcctcgctc actgactcgc    7320
tgcgctcggt cgttcggctg cggcgagcgg tatcagctca ctcaaaggcg gtaatacggt    7380
tatccacaga atcaggggat aacgcaggaa agaacatgtg agcaaaaggc cagcaaaagg    7440
ccaggaaccg taaaaaggcc gcgttgctgg cgttttttcca taggctccgc cccctgacg    7500
agcatcacaa aaatcgacgc tcaagtcaga ggtggcgaaa cccgacagga ctataaagat    7560
accaggcgtt tccccctgga agctccctcg tgcgctctcc tgttccgacc ctgccgctta    7620
ccggatacct gtccgccttt ctcccttcgg gaagcgtggc gctttctcat agctcacgct    7680
gtaggtatct cagttcggtg taggtcgttc gctccaagct gggctgtgtg cacgaaccc     7740
ccgttcagcc cgaccgctgc gccttatccg gtaactatcg tcttgagtcc aacccggtaa    7800
gacacgactt atcgccactg gcagcagcca ctggtaacag gattagcaga gcgaggtatg    7860
taggcggtgc tacagagttc ttgaagtggt ggcctaacta cggctacact agaagaacag    7920
tatttggtat ctgcgctctg ctgaagccag ttaccttcgg aaaaagagtt ggtagctctt    7980
gatccggcaa acaaaccacc gctggtagcg gtttttttgt ttgcaagcag cagattacgc    8040
gcagaaaaaa aggatctcaa gaagatcctt tgatcttttc tacggggtct gacgctcagt    8100
ggaacgaaaa ctcacgttaa gggattttgg tcatgagatt atcaaaaagg atcttcacct    8160
agatcctttt aaattaaaaa tgaagtttta aatcaatcta agtatatat gagtaaactt     8220
ggtctgacag ttaccaatgc ttaatcagtg aggcacctat ctcagcgatc tgtctatttc    8280
gttcatccat agttgcctga ctccccgtcg tgtagataac tacgatacgg gagggcttac    8340
catctggccc cagtgctgca atgataccgc gagacccacg ctcaccggct ccagatttat    8400
cagcaataaa ccagccagcc ggaagggcca agcgcagaag tggtcctgca actttatccg    8460
cctccatcca gtctattaat tgttgccggg aagctagagt aagtagttcg ccagttaata    8520
gtttgcgcaa cgttgttgcc attgctacag gcatcgtggt gtcacgctcg tcgtttggta    8580
tggcttcatt cagctccggt tcccaacgat caaggcgagt tacatgatcc cccatgttgt    8640
gcaaaaaagc ggttagctcc ttcggtcctc cgatcgttgt cagaagtaag ttggccgcag    8700
tgttatcact catggttatg gcagcactgc ataattctct tactgtcatg ccatccgtaa    8760
gatgcttttc tgtgactggt gagtactcaa ccaagtcatt ctgagaatag tgtatgcggc    8820
gaccgagttg ctcttgcccg gcgtcaatac gggataatac cgcgccacat agcagaactt    8880
taaaagtgct catcattgga aaacgttctt cggggcgaaa actctcaagg atcttaccgc    8940
tgttgagatc cagttcgatg taacccactc gtgcacccaa ctgatcttca gcatctttta    9000
ctttcaccag cgtttctggg tgagcaaaaa caggaaggca aaatgccgca aaaagggaa     9060
taagggcgac acggaaatgt tgaatactca tactcttcct ttttcaatat tattgaagca    9120
tttatcaggg ttattgtctc atgagcggat acatatttga atgtatttag aaaaataaac    9180
aaatagggggt tccgcgcaca tttccccgaa aagtgccacc tgacgtc                  9227
```

THERAPEUTIC APPLICATIONS OF CPF1-BASED GENOME EDITING

CROSS REFERENCE TO RELATED APPLICATIONS

This application claims priority to U.S. Provisional Application No. 62/363,888, filed Jul. 19, 2016, which is incorporated herein by reference in its entirety.

STATEMENT OF GOVERNMENT INTEREST

This invention was made with government support under Federal Grant Nos. AR069085 and MD140071 awarded by the NIH and Army/MRMC, respectively. The U.S. Government has certain rights to this invention.

SEQUENCE LISTING

The instant application includes a Sequence Listing which has been submitted electronically in ASCII format and is hereby incorporated by reference in its entirety. Said ASCII copy, created on Jul. 19, 2017, is named 028193-9250-WO00 Sequence Listing.txt and is 46,056 bytes in size.

TECHNICAL FIELD

The present disclosure relates to the field of gene expression alteration, genome engineering and genomic alteration of genes using Clustered Regularly Interspaced Short Palindromic Repeats from *Prevotella* and *Francisella* 1 (CRISPR/Cpf1) based systems and viral delivery systems.

BACKGROUND

RNA-guided nucleases have been adapted for genome modification in human cells including CRISPR/Cpf1 systems derived from *Streptococcus pyogenes* and *Staphylococcus aureus*. Numerous microorganisms have been shown to have DNA-editing or RNA-editing systems. Cas9 derived from *S. pyogenes* and *S. aureus* make blunt-ended double-stranded breaks (DSBs) through genomic DNA which are repaired by non-homologous end-joining (NHEJ) leaving small insertions and deletions (indels) at the repaired site or through homology directed repair in the presence of a template. These indels can be used to knockout a gene, remove a splice acceptor, or dissect genetic regulatory elements.

Hereditary genetic diseases have devastating effects on children in the United States. These diseases currently have no cure and can only be managed by attempts to alleviate the symptoms. For decades, the field of gene therapy has promised a cure to these diseases. However technical hurdles regarding the safe and efficient delivery of therapeutic genes to cells and patients have limited this approach. Duchenne muscular dystrophy (DMD) is a fatal genetic disease, clinically characterized by muscle wasting, loss of ambulation, and death typically in the third decade of life due to the loss of functional dystrophin. DMD is the result of inherited or spontaneous mutations in the dystrophin gene. Most mutations causing DMD are a result of deletions of exon(s), pushing the translational reading frame out of frame.

Dystrophin is a key component of a protein complex that is responsible for regulating muscle cell integrity and function. DMD patients typically lose the ability to physically support themselves during childhood, become progressively weaker during the teenage years, and die in their twenties. Current experimental gene therapy strategies for DMD require repeated administration of transient gene delivery vehicles or rely on permanent integration of foreign genetic material into the genomic DNA. Both of these methods have serious safety concerns. Furthermore, these strategies have been limited by an inability to deliver the large and complex dystrophin gene sequence. There remains a need for more precise and efficient gene editing tools for correcting and treating patients with mutations in the dystrophin gene.

SUMMARY

The present invention is directed to a Cpf1 guide RNA (gRNA) that targets a dystrophin gene and comprises a polynucleotide sequence corresponding to at least one of SEQ ID NOs: 36-64, 71-119, or a complement thereof.

The present invention is directed to a DNA targeting composition comprising a Cpf1 endonuclease and at least one Cpf1 gRNA described above.

The present invention is directed to a DNA targeting composition comprising a first Cpf1 gRNA and a second Cpf1 gRNA, the first Cpf1 gRNA and the second Cpf1 gRNA each comprising a polynucleotide sequence corresponding to at least one of SEQ ID NOs: 36-64, 71-119, or a complement thereof, wherein the first Cpf1 gRNA and the second Cpf1 gRNA comprise different polynucleotide sequences, and wherein the first Cpf1 gRNA and the second Cpf1 gRNA target a dystrophin gene.

The present invention is directed to an isolated polynucleotide comprising the Cpf1 gRNA described above or a polynucleotide sequence encoding the DNA targeting composition described above.

The present invention is directed to a vector comprising the Cpf1 gRNA described above, a polynucleotide sequence encoding the DNA targeting composition described above, or the isolated polynucleotide described above.

The present invention is directed to a vector encoding: (a) a first Cpf1 guide RNA (gRNA), (b) a second Cpf1 gRNA, and (c) at least one Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), wherein the first Cpf1 gRNA and the second Cpf1 gRNA comprises a polynucleotide sequence corresponding to at least one of SEQ ID NOs: 36-64, 71-119, or a complement thereof, and wherein the first Cpf1 gRNA and the second Cpf1 gRNA comprise different polynucleotide sequences.

The present invention is directed to a cell comprising the Cpf1 gRNA described above, a polynucleotide sequence encoding the DNA targeting composition described above, the isolated polynucleotide described above, or the vector described above.

The present invention is directed to a kit comprising the Cpf1 gRNA described above, a polynucleotide sequence encoding the DNA targeting composition described above, the isolated polynucleotide described above, the vector described above, or the cell described above.

The present invention is directed to a composition for deleting a segment of a dystrophin gene comprising exon 51, the composition comprising: (a) a first vector comprising a polynucleotide sequence encoding a first Cpf1 guide RNA (gRNA) and a polynucleotide sequence encoding a first Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), and (b) a second vector comprising a polynucleotide sequence encoding a second Cpf1 gRNA and a polynucleotide sequence encoding a second Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), wherein the first Cpf1 gRNA and the second Cpf1 gRNA comprise a polynucleotide sequence corresponding to at least one of SEQ ID NOs: 36-64, 71-119, or a complement thereof, wherein the first Cpf1 gRNA and the second Cpf1 gRNA comprise different polynucleotide sequences, and wherein the first vector and second vector are configured to form a first and a second double strand break in a first intron and a second intron flanking exon 51 of the human DMD gene, respectively, thereby deleting a segment of the dystrophin gene comprising exon 51.

The present invention is directed to a cell comprising the composition described above.

The present invention is directed to a modified adeno-associated viral vector for genome editing a mutant dystrophin gene in a subject comprising a first polynucleotide sequence encoding the Cpf1 gRNA described above, and a second polynucleotide sequence encoding a Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123).

The present invention is directed to a method of correcting a mutant dystrophin gene in a cell, the method comprising administering to a cell the Cpf1 gRNA described above, a polynucleotide sequence encoding the DNA targeting composition described above, the isolated polynucleotide described above, the vector described above, the composition described above, or the modified adeno-associated viral vector described above.

The present invention is directed to a method of genome editing a mutant dystrophin gene in a subject, the method comprising administering to the subject a genome editing composition comprising the Cpf1 gRNA described above, a polynucleotide sequence encoding the DNA targeting composition described above, the isolated polynucleotide described above, the vector described above, the composition described above, or the modified adeno-associated viral vector described above.

The present invention is directed to a method of treating a subject in need thereof having a mutant dystrophin gene, the method comprising administering to the subject the Cpf1 gRNA described above, a polynucleotide sequence encoding the DNA targeting composition described above, the isolated polynucleotide described above, the vector described above, the composition described above, or the modified adeno-associated viral vector described above.

The present invention is directed to a method of correcting a mutant dystrophin gene in a cell, comprising administering to the cell: (a) a first vector comprising a polynucleotide sequence encoding a first Cpf1 guide RNA (gRNA) and a polynucleotide sequence encoding a first Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), and (b) a second vector comprising a polynucleotide sequence encoding a second Cpf1 gRNA and a polynucleotide sequence encoding a second Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), wherein the first Cpf1 gRNA and the second Cpf1 gRNA comprises a polynucleotide sequence corresponding to at least one of SEQ ID NOs: 36-64, 71-119, or a complement thereof, and the vector is configured to form a first and a second double strand break in a first and a second intron flanking exon 51 of the human dystrophin gene, respectively, thereby deleting a segment of the dystrophin gene comprising exon 51 and correcting the mutant dystrophin gene in a cell.

The present invention is directed to a method of treating a subject in need thereof having a mutant dystrophin gene, the method comprising administering to the subject: (a) a first vector comprising a polynucleotide sequence encoding a first Cpf1 guide RNA (gRNA) and a polynucleotide sequence encoding a first Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), and (b) a second vector comprising a polynucleotide sequence encoding a second Cpf1 gRNA and a polynucleotide sequence encoding a second Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), wherein the first Cpf1 gRNA and the second Cpf1 gRNA comprises a polynucleotide sequence corresponding to at least one of SEQ ID NOs: 36-64, 71-119, or a complement thereof, and the first vector and the second vector are configured to form a first and a second double strand break in a first and a second intron flanking exon 51 of the human dystrophin gene, respectively, thereby deleting a segment of the dystrophin gene comprising exon 51 and treating the subject.

The present invention is directed to a Cpf1 guide RNA (gRNA) that targets an enhancer of the B-cell lymphoma/leukemia 11A (BCL11a) gene and comprises a polynucleotide sequence corresponding to at least one of SEQ ID NOs: 65-70, or a complement thereof.

The present invention is directed to a method of disrupting an enhancer of a B-cell lymphoma/leukemia 11A gene in a cell, the method comprising administering to the cell at least one Cpf1 gRNA described above and a Cpf1 endonuclease.

DETAILED DESCRIPTION

The present disclosure provides, in part, therapeutic applications of CRISPR/Cpf1-based genome editing for the treatment of diseases. Cpf1, a type V CRISPR-Cas effector endonuclease, is involved in the adaptive immunity of prokaryotes, including *Acidaminococcus* and *Lachno-*

*spiraceae* among others, and exhibits gene-editing activity in human cells through a single RNA-guided approach. The present disclosure provides methods in which the CRISPR/Cpf1-based system can be used in the treatment of genetic diseases, such as Duchenne muscular dystrophy (DMD), sickle cell anemia (SCA) and β-thalassemia.

Figure 1:
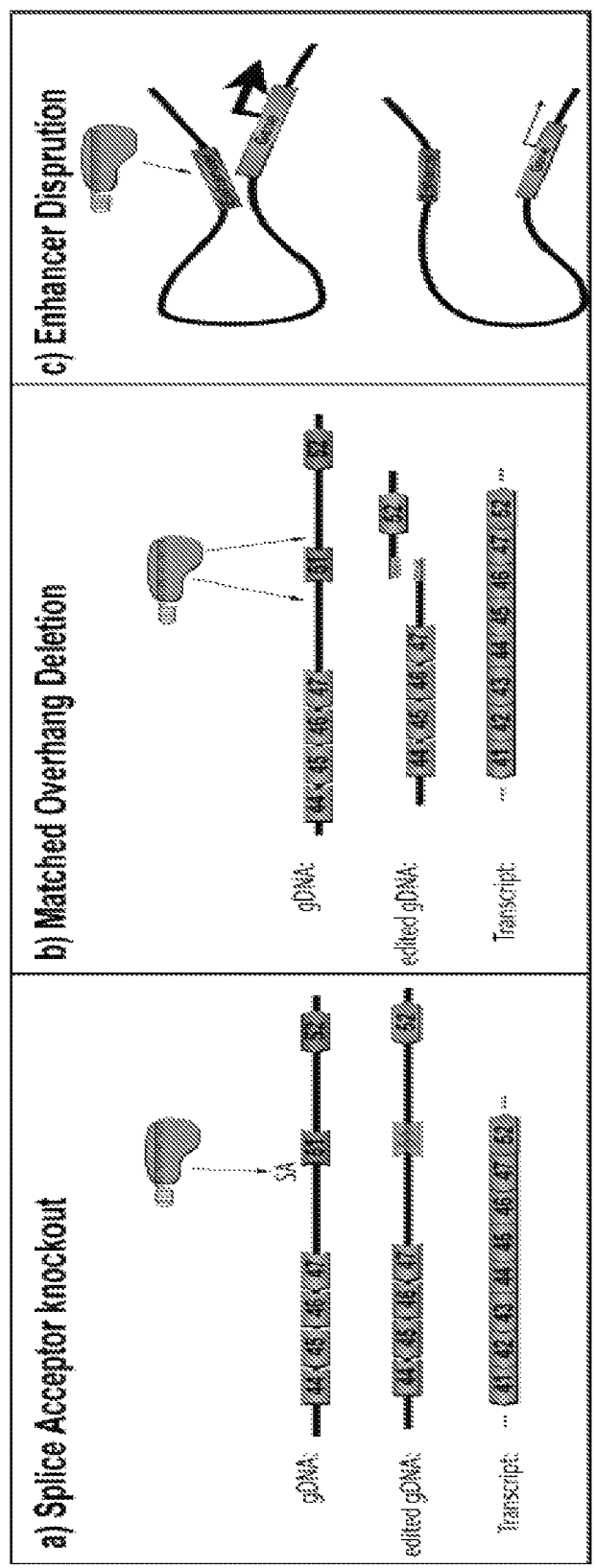
FIG. 1 is a schematic drawing showing the use of Cpf1 in three methods of treatment for genetic diseases, such as DMD and SCA/beta thalassemia, in accordance with some embodiments of the present disclosure.

According to one aspect of the present disclosure, the first method comprises a splice acceptor knockout. Cpf1 produces a larger indel footprint making efficient disruption of splice acceptors and removal of target exons from the transcript (see FIG. 1A). As shown in FIG. 1A, Cpf1 generates a 5-base-pair staggered double-stranded break through the DNA, which may be repaired through non-homologous end joining (NHEJ) and produce a larger insertion or deletion (indel) foot print then *S. pyogenes* or *S. aureus* Cas9. This will allow for more powerful disruption of splice acceptors and removal of targeted exons as the repair may leave a larger indel footprint making knockout of genetic elements, such as splice acceptors and enhancers, more efficient. Cpf1 also has a distinct protospacer-adjacent motif (PAM) sequence that increases the diversity of genomic regions that can be targeted. Cpf1 recognizes TTTN whereas *S. pyogenes* Cas9 recognizes NGG and *S. aureus* Cas9 recognizes NNGRRT. In addition, Cpf1 does not need a tracrRNA, therefore, only crRNA is required, thus also using a small guide RNA.

Another aspect of the present disclosure provides a method comprising a matched overhang deletion. Cpf1 can encourage genetic deletions through matching overhangs to remove genetic elements (see FIG. 1B). As shown in FIG. 1B, Cpf1 generates a 5-base-pair overhang that can be matched with a second double stranded break. Multiplexed Cpf1 guide RNAs can be provided with matched overhangs to encourage seamless genetic deletions. Previous work with *S. aureus* Cas9 has shown ~67% of genetic deletions are seamless with one guide RNA pair. For example, matched overhangs generated by multiplexing Cpf1 around a genetic region of interest (e.g. exon 51 in dystrophin) can encourage seamless deletions. After NHEJ, genetic deletions are made that can restore the reading frame of a mutated gene. By matching the overhangs, very precise ligations could be encouraged.

Yet another aspect of the present disclosure provides a method comprising an enhancer disruption. Cpf1 can produce a larger indel footprint making disruption of enhancers and other genetic regulatory elements more probable (see FIG. 1C). As shown in FIG. 1C, the larger indel footprint generated by Cpf1 could also be harnessed to disrupt enhancers to study enhancer function or as a potential treatment for diseases, such as SCA.

For example, the present disclosure describes the adaption of Cpf1 for the targeted genetic removal of single and multiple exons of the dystrophin gene for the treatment of Duchenne muscular dystrophy (DMD). This is accomplished by targeted mutagenesis of splice acceptors in mutational hotspots for single exon removal or by genetic deletions of single or multiple exons. Through targeted exon removal, the reading frame of dystrophin can be restored leading to improved muscle function and patient phenotype. Genetic enhancers can also be targeted as a therapeutic approach to treating disease, specifically targeting the BCL11a enhancer region or gamma globin promoter as a treatment for sickle cell anemia (SCA) or β-thalassemia. The disclosed Cpf1 gRNAs can be used with the CRISPR/Cpf1-based system to target genetic regions, such as intronic regions surrounding exon 51 of the human dystrophin gene, causing genomic deletions of this region in order to restore expression of functional dystrophin in cells from DMD patients.

Also described herein are genetic constructs, compositions and methods for delivering CRISPR/Cpf1-based gene editing system and multiple gRNAs to target the dystrophin gene. The presently disclosed subject matter also provides for methods for delivering the genetic constructs (e.g., vectors) or compositions comprising thereof to skeletal muscle. The vector can be an AAV, including modified AAV vectors. The presently disclosed subject matter describes a way to deliver active forms of this class of therapeutics to skeletal muscle that is effective, efficient and facilitates successful genome modification, as well as provide a means to rewrite the human genome for therapeutic applications and target model species for basic science applications.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

"Binding region" as used herein refers to the region within a nuclease target region that is recognized and bound by the nuclease.

"Cardiac muscle" or "heart muscle" as used interchangeably herein means a type of involuntary striated muscle found in the walls and histological foundation of the heart, the myocardium. Cardiac muscle is made of cardiomyocytes or myocardiocytes. Myocardiocytes show striations similar to those on skeletal muscle cells but contain only one, unique nucleus, unlike the multinucleated skeletal cells. In certain embodiments, "cardiac muscle condition" refers to a condition related to the cardiac muscle, such as cardiomyopathy, heart failure, arrhythmia, and inflammatory heart disease.

"Coding sequence" or "encoding nucleic acid" as used herein means the nucleic acids (RNA or DNA molecule) that comprise a polynucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimize.

"Complement" or "complementary" as used herein means a nucleic acid can mean Watson-Crick (e.g., A-T/U and C-G) or Hoogsteen base pairing between polynucleotides or polynucleotide analogs of nucleic acid molecules. "Complementarity" refers to a property shared between two nucleic acid sequences, such that when they are aligned antiparallel to each other, the polynucleotide bases at each position will be complementary.

"Correcting", "genome editing" and "restoring" as used herein refers to changing a mutant gene that encodes a truncated protein or no protein at all, such that a full-length functional or partially full-length functional protein expression is obtained. Correcting or restoring a mutant gene may include replacing the region of the gene that has the mutation or replacing the entire mutant gene with a copy of the gene that does not have the mutation with a repair mechanism such as homology-directed repair (HDR). Correcting or restoring a mutant gene may also include repairing a frameshift mutation that causes a premature stop codon, an aberrant splice acceptor site or an aberrant splice donor site, by generating a double stranded break in the gene that is then repaired using non-homologous end joining (NHEJ). NHEJ may add or delete at least one base pair during repair which may restore the proper reading frame and eliminate the premature stop codon. Correcting or restoring a mutant gene may also include disrupting an aberrant splice acceptor site or splice donor sequence. Correcting or restoring a mutant gene may also include deleting a non-essential gene segment by the simultaneous action of two nucleases on the same DNA strand in order to restore the proper reading frame by removing the DNA between the two nuclease target sites and repairing the DNA break by NHEJ.

"Cpf1 endonuclease" or "Cpf1" as used interchangeably herein refers to a single RNA-Guided endonuclease of a Class 2 CRISPR-Cas system that is a smaller and a simpler endonuclease than Cas9. The Cpf1 endonuclease targets and cleaves as a 5-nucleotide staggered cut distal to a 5'T-rich PAM.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein.

"Duchenne Muscular Dystrophy" or "DMD" as used interchangeably herein refers to a recessive, fatal, X-linked disorder that results in muscle degeneration and eventual death. DMD is a common hereditary monogenic disease and occurs in 1 in 3500 males. DMD is the result of inherited or spontaneous mutations that cause nonsense or frame shift mutations in the dystrophin gene. The majority of dystrophin mutations that cause DMD are deletions of exons that disrupt the reading frame and cause premature translation termination in the dystrophin gene. DMD patients typically lose the ability to physically support themselves during childhood, become progressively weaker during the teenage years, and die in their twenties.

"Dystrophin" as used herein refers to a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids.

"Exon 51" as used herein refers to the $51^4$ exon of the dystrophin gene. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

"Frameshift" or "frameshift mutation" as used interchangeably herein refers to a type of gene mutation wherein the addition or deletion of one or more polynucleotides causes a shift in the reading frame of the codons in the mRNA. The shift in reading frame may lead to the alteration in the amino acid sequence at protein translation, such as a missense mutation or a premature stop codon.

"Functional" and "full-functional" as used herein describes protein that has biological activity. A "functional gene" refers to a gene transcribed to mRNA, which is translated to a functional protein.

"Genetic construct" as used herein refers to the DNA or RNA molecules that comprise a polynucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be, but not limited to DMD, Becker Muscular Dystrophy (BMD), hemophilia, cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, such as β-thalassemia, xeroderma pigmentosum, Fanconi's anemia, retinitis pigmentosa, ataxia telangiectasia, Bloom's syndrome, retinoblastoma, and Tay-Sachs disease.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the CRISPR/Cpf1-based gene editing system, then the cellular machinery will repair the break by homologous recombination, which is enhanced several orders of magnitude in the presence of DNA cleavage. When the homologous DNA piece is absent, non-homologous end joining may take place instead.

"Genome editing" as used herein refers to changing a gene. Genome editing may include correcting or restoring a mutant gene. Genome editing may include knocking out a gene, such as a mutant gene or a normal gene. Genome editing may be used to treat disease or enhance muscle repair by changing the gene of interest.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. A "disrupted gene" as used herein refers to a mutant gene that has a mutation that causes a premature stop codon. The disrupted gene product is truncated relative to a full-length undisrupted gene product.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of polynucleotides may also occur, but is much more common when the overhangs are not compatible.

"Normal gene" as used herein refers to a gene that has not undergone a change, such as a loss, gain, or exchange of genetic material. The normal gene undergoes normal gene transmission and gene expression.

"Nuclease mediated NHEJ" as used herein refers to NHEJ that is initiated after a nuclease, such as a Cpf1 endonuclease, cuts double stranded DNA.

"Nucleic acid" or "oligonucleotide" or "polynucleotide" as used herein means at least two polynucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Partially-functional" as used herein describes a protein that is encoded by a mutant gene and has less biological activity than a functional protein but more than a non-functional protein.

"Premature stop codon" or "out-of-frame stop codon" as used interchangeably herein refers to nonsense mutation in a sequence of DNA, which results in a stop codon at location not normally found in the wild-type gene. A premature stop codon may cause a protein to be truncated or shorter compared to the full-length version of the protein.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter, human U6 (hU6) promoter, and CMV IE promoter.

"Skeletal muscle" as used herein refers to a type of striated muscle, which is under the control of the somatic nervous system and attached to bones by bundles of collagen fibers known as tendons. Skeletal muscle is made up of individual components known as myocytes, or "muscle cells", sometimes colloquially called "muscle fibers." Myocytes are formed from the fusion of developmental myoblasts (a type of embryonic progenitor cell that gives rise to a muscle cell) in a process known as myogenesis. These long, cylindrical, multinucleated cells are also called myofibers.

"Skeletal muscle condition" as used herein refers to a condition related to the skeletal muscle, such as muscular dystrophies, aging, muscle degeneration, wound healing, and muscle weakness or atrophy.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target gene" as used herein refers to any polynucleotide sequence encoding a known or putative gene product. The target gene may be a mutated gene involved in a genetic disease. In certain embodiments, the target gene is a human dystrophin gene or a human B-cell lymphoma/leukemia 11A gene. In certain embodiments, the target gene is a mutant human dystrophin gene.

"Target region" as used herein refers to the region of the target gene to which the CRISPR/Cpf1-based gene editing system is designed to bind and cleave.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Variant" used herein with respect to a nucleic acid means (i) a portion or fragment of a referenced polynucleotide sequence; (ii) the complement of a referenced polynucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode a Cpf1 endonuclease and at least one Cpf1 gRNA, such as a Cpf1 gRNA comprising a polynucleotide sequence of any one of SEQ ID NOs: 36-119, or complement thereof.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. CRISPR SYSTEM

A presently disclosed genetic construct (e.g., a vector) encodes a CRISPR/Cpf1-based gene editing system that is specific for a dystrophin gene (e.g., human dystrophin gene). "Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea. The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures.

Three classes of CRISPR systems (Types I, II and III effector systems) are known. The Type II effector system carries out targeted DNA double-strand break in four sequential steps, using a single effector enzyme, such as a Cpf1 endonuclease, to cleave dsDNA. Compared to the Type I and Type III effector systems, which require multiple distinct effectors acting as a complex, the Type II effector system may function in alternative contexts such as eukaryotic cells. Cpf1 endonuclease mediates cleavage of target DNA if a correct PAM is also present on the 5' end of the protospacer.

CRISPR/Cpf1 systems activity has three stages: adaptation, formation of crRNAs, and interference. During adaptation, Cas1 and Cas2 proteins facilitate the adaptation of small fragments of DNA into the CRISPR array. The processing of pre-cr-RNAs occurs during formation of crRNAs to produce mature crRNAs to guide the Cas protein, i.e., the Cpf1 endonuclease. During interference: the Cpf1 is bound to a crRNA to form a binary complex to identify and cleave a target DNA sequence.

In this system, the Cpf1 endonuclease is directed to genomic target sites by a synthetically reconstituted Cpf1 "guide RNA" ("Cpf1 gRNA"). The Cpf1 endonuclease leaves one strand longer than the other, creating 'sticky' ends, for example 4-5 nucleotide long sticky ends, unlike Cas9 which generates blunt ends. The Cpf1 endonuclease also cleaves target DNA further away from PAM compared to Cas9.

The target gene (e.g., a dystrophin gene, e.g., human dystrophin gene) can be involved in differentiation of a cell or any other process in which activation of a gene can be desired, or can have a mutation such as a frameshift mutation or a nonsense mutation. If the target gene has a mutation that causes a premature stop codon, an aberrant splice acceptor site or an aberrant splice donor site, the CRISPR/Cpf1-based gene editing system can be designed to recognize and bind a polynucleotide sequence upstream or downstream from the premature stop codon, the aberrant splice acceptor site or the aberrant splice donor site. The CRISPR/Cpf1-based system can also be used to disrupt normal gene splicing by targeting splice acceptors and donors to induce skipping of premature stop codons or restore a disrupted reading frame. The CRISPR/Cpf1-based gene editing system may or may not mediate off-target changes to protein-coding regions of the genome.

Provided herein are CRISPR/Cpf1-based engineered systems for use in genome editing and treating genetic diseases. A unique capability of the CRISPR/Cpf1-based gene editing system is the straightforward ability to simultaneously target multiple distinct genomic loci by co-expressing a single Cpf1 endonuclease with two or more Cpf1 gRNAs. The CRISPR/Cpf1-based engineered systems can be designed to target any gene, including genes involved in a genetic disease, aging, tissue regeneration, or wound healing. The CRISPR/Cpf1-based gene editing systems can include a Cpf1 endonuclease and at least one Cpf1 gRNA. In certain embodiments, the system comprises two Cpf1 gRNAs.

a. Cpf1 Endonuclease

The CRISPR/Cpf1-based gene editing system can include a Cpf1 endonuclease. Cpf1 endonuclease is an endonuclease that cleaves nucleic acid. The Cpf1 endonuclease cleaves in a staggered fashion, creating a 5 nucleotide 5' overhang 18-23 bases away from the PAM, whereas Cas9 generates blunt ends 3 nucleotide upstream of the PAM site. The Cpf1 endonuclease can be from any bacterial or archaea species, including, but not limited to, *Francisella tularensis* 1, *Francisella tularensis* subsp. *novicida*, *Prevotella albensis*, *Lachnospiraceae bacterium* MC2017 1, *Butyrivibrio proteoclasticus*, *Peregrinibacteria bacterium* GW2011_ GWA2_ 33_10, *Parcubacteria bacterium* GWC2011_GWC2_ 44_17, *Smithella* sp. SCADC, *Acidaminococcus* sp. BV3L6, *Lachnospiraceae bacterium* MA2020, *Candidatus Methanoplasma termitum*, *Eubacterium eligens*, *Moraxella bovoculi* 237, *Leptospira inadai*, *Lachnospiraceae bacterium* ND2006, *Porphyromonas crevioricanis* 3, *Prevotella disiens* or *Porphyromonas macacae*. In certain embodiments, the Cpf1 endonuclease is a Cpf1 endonuclease from *Lachnospiraceae bacterium* ND2006 ("LbCpf1") or from *Acidaminococcus* ("AsCpf1").

In some embodiments, the Cpf1 endonuclease can include a humanized AsCpf1 sequence (SEQ ID NO: 124) as follows:

(SEQ ID NO: 124)
gacggatcgggagatctcccgatccctatggtgcactctcagtacaatc tgctctgatgccgcatagttaagccagtatctgctccctgcttgtgtgtt ggaggtcgctgagtagtgcgcgagcaaaatttaagctacaacaaggcaag gcttgaccgacaattgcatgaagaatctgcttagggttaggcgttttgcg ctgcttcgcgatgtacgggccagatatacgcgttgacattgattattgac tagttattaatagtaatcaattacggggtcattagttcatagcccatata tggagttccgcgttacataacttacggtaaatggcccgcctggctgaccg cccaacgaccccgcccattgacgtcaataatgacgtatgttcccatagt aacgccaatagggactttccattgacgtcaatgggtggagtatttacggt aaactgcccacttggcagtacatcaagtgtatcatatgccaagtacgccc cctattgacgtcaatgacggtaaatggcccgcctggcattatgcccagta catgaccttatgggactttcctacttggcagtacatctacgtattagtca tcgctattaccatggtgatgcggttttggcagtacatcaatgggcgtgga tagcggtttgactcacggggatttccaagtctccacccccattgacgtcaa tgggagtttgttttggcaccaaaatcaacgggactttccaaaatgtcgta acaactccgccccattgacgcaaatgggcggtaggcgtgtacggtgggag gtctatataagcagagctctctggctaactagagaacccactgcttactg gcttatcgaaattaatacgactcactatagggagacccaagctggctagc gtttaaacttaagcttggtaccgccaccATGACACAGTTCGAGGGCTTTA

CCAACCTGTATCAGGTGAGCAAGACACTGCGGTTTGAGCTGATCCCACAG

GGCAAGACCCTGAAGCACATCCAGGAGCAGGGCTTCATCGAGGAGGACAA

GGCCCGCAATGATCACTACAAGGAGCTGAAGCCCATCATCGATCGGATCT

ACAAGACCTATGCCGACCAGTGCCTGCAGCTGGTGCAGCTGGATTGGGAG

AACCTGAGCGCCGCCATCGACTCCTATAGAAAGGAGAAAACCGAGGAGAC

AAGGAACGCCCTGATCGAGGAGCAGGCCACATATCGCAATGCCATCCACG

```
ACTACTTCATCGGCCGGACAGACAACCTGACCGATGCCATCAATAAGAGA

CACGCCGAGATCTACAAGGGCCTGTTCAAGGCCGAGCTGTTTAATGCAA

GGTGCTGAAGCAGCTGGGCACCGTGACCACAACCGAGCACGAGAACGCCC

TGCTGCGGAGCTTCGACAAGTTTACAACCTACTTCTCCGGCTTTTATGAG

AACAGGAAGAACGTGTTCAGCGCCGAGGATATCAGCACAGCCATCCCACA

CCGCATCGTGCAGGACAACTTCCCCAAGTTTAAGGAGAATTGTCACATCT

TCACACGCCTGATCACCGCCGTGCCCAGCCTGCGGGAGCACTTTGAGAAC

GTGAAGAAGGCCATCGGCATCTTCGTGAGCACCTCCATCGAGGAGGTGTT

TTCCTTCCCTTTTTATAACCAGCTGCTGACACAGACCCAGATCGACCTGT

ATAACCAGCTGCTGGGAGGAATCTCTCGGGAGGCAGGCACCGAGAAGATC

AAGGGCCTGAACGAGGTGCTGAATCTGGCCATCCAGAAGAATGATGAGAC

AGCCCACATCATCGCCTCCCTGCCACACAGATTCATCCCCCTGTTTAAGC

AGATCCTGTCCGATAGGAACACCCTGTCTTTCATCCTGGAGGAGTTTAAG

AGCGACGAGGAAGTGATCCAGTCCTTCTGCAAGTACAAGACACTGCTGAG

AAACGAGAACGTGCTGGAGACAGCCGAGGCCCTGTTTAACGAGCTGAACA

GCATCGACCTGACACACATCTTCATCAGCCACAAGAAGCTGGAGACAATC

AGCAGCGCCCTGTGCGACCACTGGGATACACTGAGGAATGCCCTGTATGA

GCGGAGAATCTCCGAGCTGACAGGCAAGATCACCAAGTCTGCCAAGGAGA

AGGTGCAGCGCAGCCTGAAGCACGAGGATATCAACCTGCAGGAGATCATC

TCTGCCGCAGGCAAGGAGCTGAGCGAGGCCTTCAAGCAGAAAACCAGCGA

GATCCTGTCCCACGCACACGCCGCCCTGGATCAGCCACTGCCTACAACCC

TGAAGAAGCAGGAGGAGAAGGAGATCCTGAAGTCTCAGCTGGACAGCCTG

CTGGGCCTGTACCACCTGCTGGACTGGTTTGCCGTGGATGAGTCCAACGA

GGTGGACCCCGAGTTCTCTGCCCGGCTGACCGGCATCAAGCTGGAGATGG

AGCCTTCTCTGAGCTTCTACAACAAGGCCAGAAATTATGCCACCAAGAAG

CCCTACTCCGTGGAGAAGTTCAAGCTGAACTTTCAGATGCCTACACTGGC

CTCTGGCTGGGACGTGAATAAGGAGAAGAACAATGGCGCCATCCTGTTTG

TGAAGAACGGCCTGTACTATCTGGGCATCATGCCAAAGCAGAAGGGCAGG

TATAAGGCCCTGAGCTTCGAGCCCACAGAGAAAACCAGCGAGGGCTTTGA

TAAGATGTACTATGACTACTTCCCTGATGCCGCCAAGATGATCCCAAAGT

GCAGCACCCAGCTGAAGGCCGTGACAGCCCACTTTCAGACCCACACAACC

CCCATCCTGCTGTCCAACAATTTCATCGAGCCTCTGGAGATCACAAAGGA

GATCTACGACCTGAACAATCCTGAGAAGGAGCCAAAGAAGTTTCAGACAG

CCTACGCCAAGAAAACCGGCGACCAGAAGGGCTACAGAGAGGCCCTGTGC

AAGTGGATCGACTTCACAAGGGATTTTCTGTCCAAGTATACCAAGACAAC

CTCTATCGATCTGTCTAGCCTGCGGCCATCCTCTCAGTATAAGGACCTGG

GCGAGTACTATGCCGAGCTGAATCCCCTGCTGTACCACATCAGCTTCCAG

AGAATCGCCGAGAAGGAGATCATGGATGCCGTGGAGACAGGCAAGCTGTA

CCTGTTCCAGATCTATAACAAGGACTTTGCCAAGGGCCACCACGGCAAGC

CTAATCTGCACACACTGTATTGGACCGGCCTGTTTTCTCCAGAGAACCTG

GCCAAGACAAGCATCAAGCTGAATGGCCAGGCCGAGCTGTTCTACCGCCC

TAAGTCCAGGATGAAGAGGATGGCACACCGGCTGGGAGAGAAGATGCTGA

ACAAGAAGCTGAAGGATCAGAAAACCCCAATCCCCGACACCCTGTACCAG

GAGCTGTACGACTATGTGAATCACAGACTGTCCCACGACCTGTCTGATGA

GGCCAGGGCCCTGCTGCCCAACGTGATCACCAAGGAGGTGTCTCACGAGA

TCATCAAGGATAGGCGCTTTACCAGCGACAAGTTCTTTTTCCACGTGCCT

ATCACACTGAACTATCAGGCCGCCAATTCCCCATCTAAGTTCAACCAGAG

GGTGAATGCCTACCTGAAGGAGCACCCCGAGACACCTATCATCGGCATCG

ATCGGGGCGAGAGAAACCTGATCTATATCACAGTGATCGACTCCACCGGC

AAGATCCTGGAGCAGCGGAGCCTGAACACCATCCAGCAGTTTGATTACCA

GAAGAAGCTGGACAACAGGGAGAAGGAGAGGGTGGCAGCAAGGCAGGCCT

GGTCTGTGGTGGGCACAATCAAGGATCTGAAGCAGGGCTATCTGAGCCAG

GTCATCCACGAGATCGTGGACCTGATGATCCACTACCAGGCCGTGGTGGT

GCTGGAGAACCTGAATTTCGGCTTTAAGAGCAAGAGGACCGGCATCGCCG

AGAAGGCCGTGTACCAGCAGTTCGAGAAGATGCTGATCGATAAGCTGAAT

TGCCTGGTGCTGAAGGACTATCCAGCAGAGAAAGTGGGAGGCGTGCTGAA

CCCATACCAGCTGACAGACCAGTTCACCTCCTTTGCCAAGATGGGCACCC

AGTCTGGCTTCCTGTTTTACGTGCCTGCCCCATATACATCTAAGATCGAT

CCCCTGACCGGCTTCGTGGACCCCTTCGTGTGGAAAACCATCAAGAATCA

CGAGAGCCGCAAGCACTTCCTGGAGGGCTTCGACTTTCTGCACTACGACG

TGAAAACCGGCGACTTCATCCTGCACTTTAAGATGAACAGAAATCTGTCC

TTCCAGAGGGGCCTGCCCGGCTTTATGCCTGCATGGGATATCGTGTTCGA

GAAGAACGAGACACAGTTTGACGCCAAGGGCACCCCCTTCATCGCCGGCA

AGAGAATCGTGCCAGTGATCGAGAATCACAGATTCACCGGCAGATACCGG

GACCTGTATCCTGCCAACGAGCTGATCGCCCTGCTGGAGGAGAAGGGCAT

CGTGTTCAGGGATGGCTCCAACATCCTGCCAAAGCTGCTGGAGAATGACG

ATTCTCACGCCATCGACACCATGGTGGCCCTGATCCGCAGCGTGCTGCAG

ATGCGGAACTCCAATGCCGCCACAGGCGAGGACTATATCAACAGCCCCGT

GCGCGATCTGAATGGCGTGTGCTTCGACTCCCGGTTTCAGAACCCAGAGT

GGCCCATGGACGCCGATGCCAATGGCGCCTACCACATCGCCCTGAAGGGC

CAGCTGCTGCTGAATCACCTGAAGGAGAGCAAGGATCTGAAGCTGCAGAA

CGGCATCTCCAATCAGGACTGGCTGGCCTACATCCAGGAGCTGCGCAACA

AAAGGCCGGCGGCCACGAAAAAGGCCGGCCAGGCAAAAAAGAAAAAGGGA

TCCTACCCATACGATGTTCCAGATTACGCTTATCCCTACGACGTGCCTGA

TTATGCATACCCATATGATGTCCCCGACTATGCCTAAGaattctgcagat atccagcacagtggcggccgctcgagtctagagggcccgtttaaacccgc tgatcagcctcgactgtgccttctagttgccagccatctgttgtttgccc ctcccccgtgccttccttgaccctggaaggtgccactcccactgtccttt cctaataaaatgaggaaattgcatcgcattgtctgagtaggtgtcattct attctgggggtggggtggggcaggacagcaagggggaggattgggaaga caatagcaggcatgctggggatgcggtgggctctatggcttctgaggcgg
```

-continued aaagaaccagctggggctctagggggtatccccacgcgccctgtagcggc
gcattaagcgcggcgggtgtggtggttacgcgcagcgtgaccgctacact
tgccagcgccctagcgcccgctcctttcgctttcttcccttcctttctcg
ccacgttcgccggctttccccgtcaagctctaaatcgggggctcccttta
gggttccgatttagtgctttacggcacctcgaccccaaaaaacttgatta
gggtgatggttcacgtagtgggccatcgcccgatagacggttttttcgcc
ctttgacgttggagtccacgttctttaatagtggactatgttccaaactg
gaacaacactcaaccctatctcggtctattcttttgatttataagggatt
ttgccgatttcggcctattggttaaaaaatgagctgatttaacaaaaatt
taacgcgaattaattctgtggaatgtgtgtcagttagggtgtggaaagtc
cccaggctccccagcaggcagaagtatgcaaagcatgcatctcaattagt
cagcaaccaggtgtggaaagtccccaggctccccagcaggcagaagtatg
caaagcatgcatctcaattagtcagcaaccatagtcccgcccctaactcc
gcccatcccgcccctaactccgcccagttccgcccattctccgcccatg
gctgactaattttttttatttatgcagaggccgaggccgcctctgcctct
gagctattccagaagtagtgaggaggcttttttggaggcctaggatttgc
aaaaagctcccgggagcttgtatatccattttcggatctgatcaagagac
aggatgaggatcgtttcgcatgattgaacaagatggattgcacgcaggtt
ctccggccgcttgggtggagaggctattcggctatgactgggcacaacag
acaatcggctgctctgatgccgccgtgttccggctgtcagcgcaggggcg
cccggttcttttttgtcaagaccgacctgtccggtgccctgaatgaactgc
aggacgaggcagcgcggctatcgtggctggccacgacgggcgttccttgc
gcagctgtgctcgacgttgtcactgaagcgggaagggactggctgctatt
gggcgaagtgccggggcaggatctcctgtcatctcaccttgctcctgccg
agaaagtatccatcatggctgatgcaatgcggcggctgcatacgcttgat
ccggctacctgcccattcgaccaccaagcgaaacatcgcatcgagcgagc
acgtactcggatggaagccggtcttgtcgatcaggatgatctggacgaag
agcatcaggggctcgcgccagccgaactgttcgccaggctcaaggcgcgc
atgcccgacggcgaggatctcgtcgtgacccatggcgatgcctgcttgcc
gaatatcatggtggaaaatggccgcttttctggattcatcgactgtggcc
ggctgggtgtggcggaccgctatcaggacatagcgttggctacccgtgat
attgctgaagagcttggcggcgaatgggctgaccgcttcctcgtgcttta
cggtatcgccgctcccgattcgcagcgcatcgccttctatcgccttcttg
acgagttcttctgagcgggactctggggttcgaaatgaccgaccaagcga
cgcccaacctgccatcacgagatttcgattccaccgccgccttctatgaa
aggttgggcttcggaatcgttttccgggacgccggctggatgatcctcca
gcgcggggatctcatgctggagttcttcgcccaccccaacttgtttattg
cagcttataatggttacaaataaagcaatagcatcacaaatttcacaaat
aaagcatttttttcactgcattctagttgtggtttgtccaaactcatcaa
tgtatcttatcatgtctgtataccgtcgacctctagctagagcttggcgt aatcatggtcatagctgtttcctgtgtgaaattgttatccgctcacaatt
ccacacaacatacgagccggaagcataaagtgtaaagcctggggtgccta
atgagtgagctaactcacattaattgcgttgcgctcactgcccgctttcc
agtcgggaaacctgtcgtgccagctgcattaatgaatcggccaacgcgcg
gggagaggcggtttgcgtattgggcgctcttccgcttcctcgctcactga
ctcgctgcgctcggtcgttcggctgcggcgagcggtatcagctcactcaa
aggcggtaatacggttatccacagaatcaggggataacgcaggaaagaac
atgtgagcaaaaggccagcaaaaggccaggaaccgtaaaaaggccgcgtt
gctggcgtttttccataggctccgcccccctgacgagcatcacaaaaatc
gacgctcaagtcagaggtggcgaaacccgacaggactataaagataccag
gcgtttccccctggaagctccctcgtgcgctctcctgttccgaccctgcc
gcttaccggatacctgtccgcctttctcccttcgggaagcgtggcgcttt
ctcatagctcacgctgtaggtatctcagttcggtgtaggtcgttcgctcc
aagctgggctgtgtgcacgaaccccccgttcagcccgaccgctgcgcctt
atccggtaactatcgtcttgagtccaacccggtaagacacgacttatcgc
cactggcagcagccactggtaacaggattagcagagcgaggtatgtaggc
ggtgctacagagttcttgaagtggtggcctaactacggctacactagaag
aacagtatttggtatctgcgctctgctgaagccagttaccttcggaaaaa
gagttggtagctcttgatccggcaaacaaaccaccgctggtagcggtttt
tttgtttgcaagcagcagattacgcgcagaaaaaaaggatctcaagaaga
tcctttgatcttttctacggggtctgacgctcagtggaacgaaaactcac
gttaagggattttggtcatgagattatcaaaaaggatcttcacctagatc
cttttaaattaaaaatgaagttttaaatcaatctaaagtatatatgagta
aacttggtctgacagttaccaatgcttaatcagtgaggcacctatctcag
cgatctgtctatttcgttcatccatagttgcctgactccccgtcgtgtag
ataactacgatacgggagggcttaccatctggccccagtgctgcaatgat
accgcgagacccacgctcaccggctccagatttatcagcaataaaccagc
cagccggaagggccgagcgcagaagtggtcctgcaactttatccgcctcc
atccagtctattaattgttgccgggaagctagagtaagtagttcgccagt
taatagtttgcgcaacgttgttgccattgctacaggcatcgtggtgtcac
gctcgtcgtttggtatggcttcattcagctccggttcccaacgatcaagg
cgagttacatgatcccccatgttgtgcaaaaaagcggttagctccttcgg
tcctccgatcgttgtcagaagtaagttggccgcagtgttatcactcatgg
ttatggcagcactgcataattctcttactgtcatgccatccgtaagatgc
ttttctgtgactggtgagtactcaaccaagtcattctgagaatagtgtat
gcggcgaccgagttgctcttgcccggcgtcaatacgggataataccgcgc
cacatagcagaactttaaaagtgctcatcattggaaaacgttcttcgggg
cgaaaactctcaaggatcttaccgctgttgagatccagttcgatgtaacc
cactcgtgcacccaactgatcttcagcatcttttactttcaccagcgttt
ctgggtgagcaaaaacaggaaggcaaaatgccgcaaaaaagggaataagg
gcgacacggaaatgttgaatactcatactcttcctttttcaatattattg aagcatttatcagggttattgtctcatgagcggatacatatttgaatgta
tttagaaaaataaacaaatagggggttccgcgcacatttccccgaaaagtg
ccacctgacgtc.

In some embodiments, the Cpf1 endonuclease can include a humanized LbCpf1 sequence (SEQ ID NO: 125) as follows:

(SEQ ID NO: 125)
gacggatcgggagatctcccgatcccctatggtgcactctcagtacaatc tgctctgatgccgcatagttaagccagtatctgctccctgcttgtgtgtt ggaggtcgctgagtagtgcgcgagcaaaatttaagctacaacaaggcaag gcttgaccgacaattgcatgaagaatctgatagggttaggcgttttgcgc tgatcgcgatgtacgggccagatatacgcgttgacattgattattgacta gttattaatagtaatcaattacggggtcattagttcatagcccatatatg gagttccgcgttacataacttacggtaaatggcccgcctggctgaccgcc caacgaccccgcccattgacgtcaataatgacgtatgttcccatagtaa cgccaatagggactttccattgacgtcaatgggtggagtatttacggtaa actgcccacttggcagtacatcaagtgtatcatatgccaagtacgcccc tattgacgtcaatgacggtaaatggcccgcctggcattatgcccagtaca tgaccttatgggactttcctacttggcagtacatctacgtattagtcatc gctattaccatggtgatgcggttttggcagtacatcaatgggcgtggata gcggtttgactcacggggatttccaagtctccaccccattgacgtcaatg ggagtttgttttggcaccaaaatcaacgggactttccaaatgtcgtaaca actccgccccattgacgcaaatgggcggtaggcgtgtacggtgggaggtc tatataagcagagctctctggctaactagagaacccactgcttactggct tatcgaaattaatacgactcactatagggagacccaagctggctagcgtt taaacttaagcttggtaccgccaccATGAGCAAGCTGGAGAAGTTTACAA

ACTGCTACTCCCTGTCTAAGACCCTGAGGTTCAAGGCCATCCCTGTGGGC

AAGACCCAGGAGAACATCGACAATAAGCGGCTGCTGGTGGAGGACGAGAA

GAGAGCCGAGGATTATAAGGGCGTGAAGAAGCTGCTGGATCGCTACTATC

TGTCTTTTATCAACGACGTGCTGCACAGCATCAAGCTGAAGAATCTGAAC

AATTACATCAGCCTGTTCCGGAAGAAAACCAGAACCGAGAAGGAGAATAA

GGAGCTGGAGAACCTGGAGATCAATCTGCGGAAGGAGATCGCCAAGGCCT

TCAAGGGCAACGAGGGCTACAAGTCCCTGTTTAAGAAGGATATCATCGAG

ACAATCCTGCCAGAGTTCCTGGACGATAAGGACGAGATCGCCCTGGTGAA

CAGCTTCAATGGCTTTACCACAGCCTTCACCGGCTTCTTTGATAACAGAG

AGAATATGTTTTCCGAGGAGGCCAAGAGCACATCCATCGCCTTCAGGTGT

ATCAACGAGAATCTGACCCGCTACATCTCTAATATGGACATCTTCGAGAA

GGTGGACGCCATCTTTGATAAGCACGAGGTGCAGGAGATCAAGGAGAAGA

TCCTGAACAGCGACTATGATGTGGAGGATTTCTTTGAGGGCGAGTTCTTT

AACTTTGTGCTGACACAGGAGGGCATCGACGTGTATAACGCCATCATCGG

CGGCTTCGTGACCGAGAGCGGCGAGAAGATCAAGGGCCTGAACGAGTACA

TCAACCTGTATAATCAGAAAACCAAGCAGAAGCTGCCTAAGTTTAAGCCA

CTGTATAAGCAGGTGCTGAGCGATCGGGAGTCTCTGAGCTTCTACGGCGA

GGGCTATACATCCGATGAGGAGGTGCTGGAGGTGTTTAGAAACACCCTGA

ACAAGAACAGCGAGATCTTCAGCTCCATCAAGAAGCTGGAGAAGCTGTTC

AAGAATTTTGACGAGTACTCTAGCGCCGGCATCTTTGTGAAGAACGGCCC

CGCCATCAGCACAATCTCCAAGGATATCTTCGGCGAGTGGAACGTGATCC

GGGACAAGTGGAATGCCGAGTATGACGATATCCACCTGAAGAAGAAGGCC

GTGGTGACCGAGAAGTACGAGGACGATCGGAGAAAGTCCTTCAAGAAGAT

CGGCTCCTTTTCTCTGGAGCAGCTGCAGGAGTACGCCGACGCCGATCTGT

CTGTGGTGGAGAAGCTGAAGGAGATCATCATCCAGAAGGTGGATGAGATC

TACAAGGTGTATGGCTCCTCTGAGAAGCTGTTCGACGCCGATTTTGTGCT

GGAGAAGAGCCTGAAGAAGAACGACGCCGTGGTGGCCATCATGAAGGACC

TGCTGGATTCTGTGAAGAGCTTCGAGAATTACATCAAGGCCTTCTTTGGC

GAGGGCAAGGAGACAAACAGGGACGAGTCCTTCTATGGCGATTTTGTGCT

GGCCTACGACATCCTGCTGAAGGTGGACCACATCTACGATGCCATCCGCA

ATTATGTGACCCAGAAGCCCTACTCTAAGGATAAGTTCAAGCTGTATTTT

CAGAACCCTCAGTTCATGGGCGGCTGGGACAAGGATAAGGAGACAGACTA

TCGGGCCACCATCCTGAGATACGGCTCCAAGTACTATCTGGCCATCATGG

ATAAGAAGTACGCCAAGTGCCTGCAGAAGATCGACAAGGACGATGTGAAC

GGCAATTACGAGAAGATCAATAAGCTGCTGCCCGGCCCTAATAAGATGC

TGCCAAAGGTGTTCTTTTCTAAGAAGTGGATGGCCTACTATAACCCCAGC

GAGGACATCCAGAAGATCTACAAGAATGGCACATTCAAGAAGGGCGATAT

GTTTAACCTGAATGACTGTCACAAGCTGATCGACTTCTTTAAGGATAGCA

TCTCCCGGTATCCAAAGTGGTCCAATGCCTACGATTTCAACTTTTCTGAG

ACAGAGAAGTATAAGGACATCGCCGGCTTTTACAGAGAGGTGGAGGAGCA

GGGCTATAAGGTGAGCTTCGAGTCTGCCAGCAAGAAGGAGGTGGATAAGC

TGGTGGAGGAGGGCAAGCTGTATATGTTCCAGATCTATAACAAGGACTTT

TCCGATAAGTCTCACGGCACACCCAATCTGCACACCATGTACTTCAAGCT

GCTGTTTGACGAGAACAATCACGGACAGATCAGGCTGAGCGGAGGAGCAG

AGCTGTTCATGAGGCGCGCCTCCCTGAAGAAGGAGGAGCTGGTGGTGCAC

CCAGCCAACTCCCCTATCGCCAACAAGAATCCAGATAATCCCAAGAAAAC

CACAACCCTGTCCTACGACGTGTATAAGGATAAGAGGTTTTCTGAGGACC

AGTACGAGCTGCACATCCCAATCGCCATCAATAAGTGCCCCAAGAACATC

TTCAAGATCAATACAGAGGTGCGCGTGCTGCTGAAGCACGACGATAACCC

CTATGTGATCGGCATCGATAGGGGCGAGCGCAATCTGCTGTATATCGTGG

TGGTGGACGGCAAGGGCAACATCGTGGAGCAGTATTCCCTGAACGAGACT

ATCAACAACTTCAACGGCATCAGGATCAAGACAGATTACCACTCTCTGCT

GGACAAGAAGGAGAAGGAGAGGTTCGAGGCCCGCCAGAACTGGACCTCCA

TCGAGAATATCAAGGAGCTGAAGGCCGGCTATATCTCTCAGGTGGTGCAC

AAGATCTGCGAGCTGGTGGAGAAGTACGATGCCGTGATCGCCCTGGAGGA

CCTGAACTCTGGCTTTAAGAATAGCCGCGTGAAGGTGGAGAAGCAGGTGT
ATCAGAAGTTCGAGAAGATGCTGATCGATAAGCTGAACTACATGGTGGAC
AAGAAGTCTAATCCTTGTGCAACAGGCGGCGCCCTGAAGGGCTATCAGAT
CACCAATAAGTTCGAGAGCTTTAAGTCCATGTCTACCCAGAACGGCTTCA
TCTTTTACATCCCTGCCTGGCTGACATCCAAGATCGATCCATCTACCGGC
TTTGTGAACCTGCTGAAAACCAAGTATACCAGCATCGCCGATTCCAAGAA
GTTCATCAGCTCCTTTGACAGGATCATGTACGTGCCCGAGGAGGATCTGT
TCGAGTTTGCCCTGGACTATAAGAACTTCTCTCGCACAGACGCCGATTAC
ATCAAGAAGTGGAAGCTGTACTCCTACGGCAACCGGATCAGAATCTTCCG
GAATCCTAAGAAGAACAACGTGTTCGACTGGGAGGAGGTGTGCCTGACCA
GCGCCTATAAGGAGCTGTTCAACAAGTACGGCATCAATTATCAGCAGGGC
GATATCAGAGCCCTGCTGTGCGAGCAGTCCGACAAGGCCTTCTACTCTAG
CTTTATGGCCCTGATGAGCCTGATGCTGCAGATGCGGAACAGCATCACAG
GCCGCACCGACGTGGATTTTCTGATCAGCCCTGTGAAGAACTCCGACGGC
ATCTTCTACGATAGCCGGAACTATGAGGCCCAGGAGAATGCCATCCTGCC
AAAGAACGCCGACGCCAATGGCGCCTATAACATCGCCAGAAAGGTGCTGT
GGGCCATCGGCCAGTTCAAGAAGGCCGAGGACGAGAAGCTGGATAAGGTG
AAGATCGCCATCTCTAACAAGGAGTGGCTGGAGTACGCCCAGACCAGCGT
GAAGCACAAAAGGCCGGCGGCCACGAAAAAGGCCGGCCAGGCAAAAAAGA
AAAAGGGATCCTACCCATACGATGTTCCAGATTACGCTTATCCCTACGAC
GTGCCTGATTATGCATACCCATATGATGTCCCCGACTATGCCTAAGaatt
ctgcagatatccagcacagtggcggccgctcgagtctagagggcccgttt
aaacccgctgatcagcctcgactgtgccttctagttgccagccatctgtt
gtttgcccctcccccgtgccttccttgaccctggaaggtgccactcccac
tgtcctttcctaataaaatgaggaaattgcatcgcattgtctgagtaggt
gtcattctattctggggggtggggtggggcaggacagcaagggggaggat
tgggaagacaatagcaggcatgctggggatgcggtgggctctatggatct
gaggcggaaagaaccagctgggggctctaggggtatccccacgcgccctg
tagcggcgcattaagcgcggcgggtgtggtggttacgcgcagcgtgaccg
ctacacttgccagcgccctagcgcccgctcctttcgctttcttccatcat
tctcgccacgttcgccggctttccccgtcaagctctaaatcgggggctcc
ctttagggttccgatttagtgctttacggcacctcgaccccaaaaaactt
gattagggtgatggttcacgtagtgggccatcgccctgatagacggtttt
tcgccctttgacgttggagtccacgttctttaatagtggactcttgttcc
aaactggaacaacactcaaccctatctcggtctattcttttgatttataa
gggattttgccgatttcggcctattggttaaaaaatgagctgatttaaca
aaaatttaacgcgaattaattctgtggaatgtgtgtcagttagggtgtgg
aaagtccccaggctccccagcaggcagaagtatgcaaagcatgcatctca
attagtcagcaaccaggtgtggaaagtccccaggctccccagcaggcaag
agtatgcaaagcatgcatctcaattagtcagcaaccatagtcccgcccct
aactccgcccatcccgcccctaactccgcccagttccgcccattctccgc cccatggctgactaattttttttatttatgcagaggccgaggccgcctct
gcctctgagctattccagaagtagtgaggaggcttttttggaggcctagg
cttttgcaaaaagctcccgggagcttgtatatccattttcggatctgatc
aagagacaggatgaggatcgtttcgcatgattgaacaagatggattgcac
gcaggttctccggccgcttgggtggagaggctattcggctatgactgggc
acaacagacaatcggctgctctgatgccgccgtgttccggctgtcagcgc
aggggcgcccggttcttttttgtcaagaccgacctgtccggtgccctgaat
gaactgcaggacgaggcagcgcggctatcgtggctggccacgacgggcgt
tccttgcgcagctgtgctcgacgttgtcactgaagcgggaagggactggc
tgctattgggcgaagtgccggggcaggatctcctgtcatctcaccttgct
cctgccgagaaagtatccatcatggctgatgcaatgcggcggctgcatac
gcttgatccggctacctgcccattcgaccaccaagcgaaacatcgcatcg
agcgagcacgtactcggatggaagccggtcttgtcgatcaggatgatctg
gacgaagagcatcaggggctcgcgccagccgaactgttcgccaggctcaa
ggcgcgcatgcccgacggcgaggatctcgtcgtgacccatggcgatgcct
gcttgccgaatatcatggtggaaaatggccgcttttctggattcatcgac
tgtggccggctgggtgtggcggaccgctatcaggacatagcgttggctac
ccgtgatattgctgaagagcttggcggcgaatgggctgaccgcttcctcg
tgctttacggtatcgccgctcccgattcgcagcgcatcgccttctatcgc
cttcttgacgagttcttctgagcgggactctggggttcgaaatgaccgac
caagcgacgcccaacctgccatcacgagatttcgattccaccgccgcctt
ctatgaaaggttgggcttcggaatcgttttccgggacgccggctggatga
tcctccagcgcggggatctcatgctggagttcttcgcccaccccaacttg
tttattgcagcttataatggttacaaataaagcaatagcatcacaaattt
cacaaataaagcatttttttcactgcattctagttgtggtttgtccaaca
tcatcaatgtatcttatcatgtctgtataccgtcgacctctagctagagc
ttggcgtaatcatggtcatagctgtttcctgtgtgaaattgttatccgct
cacaattccacacaacatacgagccggaagcataaagtgtaaagcctggg
gtgcctaatgagtgagctaactcacattaattgcgttgcgctcactgccc
gctttccagtcgggaaacctgtcgtgccagctgcattaatgaatcggcca
acgcgcggggagaggcggtttgcgtattgggcgctcttccgcttcctcgc
tcactgactcgctgcgctcggtcgttcggctgcggcgagcggtatcagct
cactcaaaggcggtaatacggttatccacagaatcagggataacgcagg
aaagaacatgtgagcaaaaggccagcaaaaggccaggaaccgtaaaaagg
ccgcgttgctggcgtttttccataggctccgcccccctgacgagcatcac
aaaaatcgacgctcaagtcagaggtggcgaaacccgacaggactataaag
ataccaggcgtttccccctggaagctccctcgtgcgctctcctgttccga
ccctgccgcttaccggatacctgtccgcctttctcccttcgggaagcgtg
gcgctttctcatagctcacgctgtaggtatctcagttcggtgtaggtcgt
tcgctccaagctgggctgtgtgcacgaaccccccgttcagcccgaccgct -continued
```
gcgccttatccggtaactatcgtcttgagtccaacccggtaagacacgac ttatcgccactggcagcagccactggtaacaggattagcagagcgaggta tgtaggcggtgctacagagttcttgaagtggtggcctaactacggctaca ctagaagaacagtatttggtatctgcgctctgctgaagccagttaccttc ggaaaaagagttggtagctcttgatccggcaaacaaaccaccgctggtag cggttttttgtttgcaagcagcagattacgcgcagaaaaaaaggatctc aagaagatcctttgatcttttctacggggtctgacgctcagtggaacgaa aactcacgttaagggatttggtcatgagattatcaaaaaggatcttcac ctagatccttttaaattaaaaatgaagttttaaatcaatctaaagtatat atgagtaaacttggtctgacagttaccaatgcttaatcagtgaggcacct atctcagcgatctgtctatttcgttcatccatagttgcctgactcccgt cgtgtagataactacgatacgggagggcttaccatctggcccagtgctg caatgataccgcgagacccacgctcaccggctccagatttatcagcaata aaccagccagccggaagggccgagcgcagaagtggtcctgcaactttatc cgcctccatccagtctattaattgttgccgggaagctagagtaagtagtt cgccagttaatagtttgcgcaacgttgttgccattgctacaggcatcgtg gtgtcacgctcgtcgtttggtatggcttcattcagctccggttcccaacg atcaaggcgagttacatgatcccccatgttgtgcaaaaaagcggttagct ccttcggtcctccgatcgttgtcagaagtaagttggccgcagtgttatca ctcatggttatggcagcactgcataattctcttactgtcatgccatccgt aagatgcttttctgtgactggtgagtactcaaccaagtcattctgagaat agtgtatgcggcgaccgagttgctcttgcccggcgtcaatacgggataat accgcgccacatagcagaactttaaaagtgctcatcattggaaaacgttc ttcggggcgaaaactctcaaggatcttaccgctgttgagatccagttcga tgtaacccactcgtgcacccaactgatcttcagcatcttttactttcacc agcgtttctgggtgagcaaaaacaggaaggcaaaatgccgcaaaaaggg aataagggcgacacggaaatgttgaatactcatactcttcctttttcaat attattgaagcatttatcagggttattgtctcatgagcggatacatattt gaatgtatttagaaaaataaacaaatagggggttccgcgcacatttccccg aaaagtgccacctgacgtc.
```

A Cpf1 endonuclease can interact with one or more Cpf1 gRNAs and, in concert with the Cpf1 gRNA(s), localizes to a site which comprises a target domain, and in certain embodiments, a PAM sequence. In certain embodiments, the ability of a Cpf1 endonuclease to interact with and cleave a target nucleic acid is PAM sequence dependent. A PAM sequence is a sequence in the target nucleic acid. In certain embodiments, cleavage of the target nucleic acid occurs upstream from the PAM sequence. Cpf1 endonucleases from different bacterial species can recognize different sequence motifs (e.g., PAM sequences). In certain embodiments, a Cpf1 endonuclease recognizes a PAM of TTTA (SEQ ID NO: 120), TTTG (SEQ ID NO: 121), TTTC (SEQ ID NO: 122), or TTTT (SEQ ID NO: 123).

In certain embodiments, the vector encodes at least one Cpf1 endonuclease that recognizes a PAM of TTTA (SEQ ID NO: 120), TTTG (SEQ ID NO: 121), TTTC (SEQ ID NO: 122), or TTTT (SEQ ID NO: 123). In certain embodiments, the at least one Cpf1 endonuclease is a Cpf1 endonuclease from *Lachnospiraceae bacterium* ND2006 ("LbCpf1") or from *Acidaminococcus* ("AsCpf1"). In certain embodiments, the Cpf1 endonuclease is encoded by the polynucleotide sequence of SEQ ID NO: 124 or SEQ ID NO: 125.

A nucleic acid encoding a Cpf1 endonuclease can be a synthetic nucleic acid sequence. For example, the synthetic nucleic acid molecule can be chemically modified. The synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

Additionally or alternatively, a nucleic acid encoding a Cpf1 endonuclease may comprise a nuclear localization sequence (NLS). Nuclear localization sequences are known in the art.

b. Cpf1 gRNAs

The CRISPR/Cpf1-based gene editing system includes at least one Cpf1 gRNA, e.g., one Cpf1 gRNA, two Cpf1 gRNAs, three gRNAs, etc. The gRNA provides the targeting of a CRISPR/Cpf1-based gene editing system. The Cpf1 gRNA may target any desired DNA sequence by exchanging the sequence encoding a protospacer which confers targeting specificity with the desired DNA target. The "target region", "target sequence" or "protospacer" as used interchangeably herein refers to the region of the target gene (e.g., a dystrophin gene) to which the CRISPR/Cpf1-based gene editing system targets. The target sequence or protospacer is preceded by a PAM sequence at the 5' end of the protospacer. In some embodiments, the PAM sequence may be TTTA (SEQ ID NO: 120), TTTG (SEQ ID NO: 121), TTTC (SEQ ID NO: 122), or TTTT (SEQ ID NO: 123).

In some embodiments, the protospacer can be between about 17 bp to about 23 bp. In some embodiments, the Cpf1 gRNA can include a polynucleotide sequence that corresponds to the protospacer or a fragment thereof. In some embodiments, the Cpf1 gRNA can include between about 17 bp to about 23 bp of the protospacer. In some embodiments, the about 17 bp to about 23 bp of the protospacer are consecutive.

In some embodiments, the target region can include a polynucleotide sequence of any one of SEQ ID NOs: 1-35, a fragment of any one of SEQ ID NOs: 1-35, or complement thereof. In some embodiments, the Cpf1 gRNA includes a polynucleotide sequence of any one of SEQ ID NOs: 36-119, a fragment of any one of SEQ ID NOs: 36-119, or complement thereof. In some embodiments, the fragment of any one of SEQ ID NOs: 36-119 is about 17 bp to about 23 bp in length. In some embodiments, the about 17 bp to about 23 bp in the fragment are consecutive.

The CRISPR/Cpf1-based gene editing system may include at least one Cpf1 gRNA, wherein the gRNAs target different DNA sequences. The target DNA sequences may be overlapping. The number of Cpf1 gRNAs encoded by a presently disclosed genetic construct (e.g., an AAV vector) can be at least 1 Cpf1 gRNA, at least 2 different Cpf1 gRNA, at least 3 different Cpf1 gRNA at least 4 different Cpf1 gRNA, at least 5 different Cpf1 gRNA, at least 6 different Cpf1 gRNA, at least 7 different Cpf1 gRNA, at least 8 different Cpf1 gRNA, at least 9 different Cpf1 gRNA, at least 10 different Cpf1 gRNAs, at least 11 different Cpf1 gRNAs, at least 12 different Cpf1 gRNAs, at least 13 different Cpf1 gRNAs, at least 14 different Cpf1 gRNAs, at least 15 different Cpf1 gRNAs, at least 16 different Cpf1 gRNAs, at least 17 different Cpf1 gRNAs, at least 18 different Cpf1 gRNAs, at least 18 different Cpf1 gRNAs, at least 20 different Cpf1 gRNAs, at least 25 different Cpf1 gRNAs, at least 30 different Cpf1 gRNAs, at least 35 different Cpf1 gRNAs, at least 40 different Cpf1 gRNAs, at least 45 different Cpf1 gRNAs, or at least 50 different Cpf1 gRNAs. The number of Cpf1 gRNA encoded by a presently disclosed vector can be between at least 1 Cpf1 gRNA to at least 50 different Cpf1 gRNAs, at least 1 Cpf1 gRNA to at least 45 different Cpf1 gRNAs, at least 1 Cpf1 gRNA to at least 40 different Cpf1 gRNAs, at least 1 Cpf1 gRNA to at least 35 different Cpf1 gRNAs, at least 1 Cpf1 gRNA to at least 30 different Cpf1 gRNAs, at least 1 Cpf1 gRNA to at least 25 different Cpf1 gRNAs, at least 1 Cpf1 gRNA to at least 20 different Cpf1 gRNAs, at least 1 Cpf1 gRNA to at least 16 different Cpf1 gRNAs, at least 1 Cpf1 gRNA to at least 12 different Cpf1 gRNAs, at least 1 Cpf1 gRNA to at least 8 different Cpf1 gRNAs, at least 1 Cpf1 gRNA to at least 4 different Cpf1 gRNAs, at least 4 Cpf1 gRNAs to at least 50 different Cpf1 gRNAs, at least 4 different Cpf1 gRNAs to at least 45 different Cpf1 gRNAs, at least 4 different Cpf1 gRNAs to at least 40 different Cpf1 gRNAs, at least 4 different Cpf1 gRNAs to at least 35 different Cpf1 gRNAs, at least 4 different Cpf1 gRNAs to at least 30 different Cpf1 gRNAs, at least 4 different Cpf1 gRNAs to at least 25 different Cpf1 gRNAs, at least 4 different Cpf1 gRNAs to at least 20 different Cpf1 gRNAs, at least 4 different Cpf1 gRNAs to at least 16 different Cpf1 gRNAs, at least 4 different Cpf1 gRNAs to at least 12 different Cpf1 gRNAs, at least 4 different Cpf1 gRNAs to at least 8 different Cpf1 gRNAs, at least 8 different Cpf1 gRNAs to at least 50 different Cpf1 gRNAs, at least 8 different Cpf1 gRNAs to at least 45 different Cpf1 gRNAs, at least 8 different Cpf1 gRNAs to at least 40 different Cpf1 gRNAs, at least 8 different Cpf1 gRNAs to at least 35 different Cpf1 gRNAs, 8 different Cpf1 gRNAs to at least 30 different Cpf1 gRNAs, at least 8 different Cpf1 gRNAs to at least 25 different Cpf1 gRNAs, 8 different Cpf1 gRNAs to at least 20 different Cpf1 gRNAs, at least 8 different Cpf1 gRNAs to at least 16 different Cpf1 gRNAs, or 8 different Cpf1 gRNAs to at least 12 different Cpf1 gRNAs. In certain embodiments, the genetic construct (e.g., an AAV vector) encodes one Cpf1 gRNA, i.e., a first Cpf1 gRNA, and optionally a Cpf1 endonuclease. In certain embodiments, a first genetic construct (e.g., a first AAV vector) encodes one Cpf1 gRNA, i.e., a first Cpf1 gRNA, and optionally a Cpf1 endonuclease, and a second genetic construct (e.g., a second AAV vector) encodes one Cpf1 gRNA, i.e., a second Cpf1 gRNA, and optionally a Cpf1 endonuclease.

3. CRISPR/Cpf1-BASED GENE EDITING SYSTEM GENETIC CONSTRUCTS FOR GENOME EDITING OF DYSTROPHIN GENE

The present invention is directed to genetic constructs for genome editing, genomic alteration or altering gene expression of a dystrophin gene (e.g., human dystrophin gene). The genetic constructs include at least one Cpf1 gRNA that targets human dystrophin gene sequences, such as Cpf1 endonuclease-compatible targets. The disclosed gRNAs can be included in a CRISPR/Cpf1-based gene editing system, including systems that use Cpf1 endonuclease, to target regions in the dystrophin gene, such as intronic regions surrounding exons, such as exon 51, of the human dystrophin gene, splice acceptor sites, and/or exonic regions, causing genomic deletions of this region in order to restore expression of functional dystrophin in cells from DMD patients.

DMD is a severe muscle wasting disease caused by genetic mutations to the dystrophin gene. Dystrophin is a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane. The dystrophin gene is 2.2 megabases at locus Xp21. The primary transcription measures about 2,400 kb with the mature mRNA being about 14 kb. 79 exons code for the protein which is over 3500 amino acids. Normal skeleton muscle tissue contains only small amounts of dystrophin but its absence of abnormal expression leads to the development of severe and incurable symptoms. Some mutations in the dystrophin gene lead to the production of defective dystrophin and severe dystrophic phenotype in affected patients. Some mutations in the dystrophin gene lead to partially-functional dystrophin protein and a much milder dystrophic phenotype in affected patients.

DMD is the result of inherited or spontaneous mutations that cause nonsense or frame shift mutations in the dystrophin gene. Naturally occurring mutations and their consequences are relatively well understood for DMD. Mutations are typically deletions or duplications of regions of the gene that make the protein out of frame and completely dysfunctional. Removal of single exons can be applied to as many as 83% of patients by frame corrections restoring a nearly functional protein. CPF1 can target dystrophin exons and be used to knockout single exons by targeting splice acceptors or delete genetic regions to remove single or multiple exons.

It is known that in-frame deletions that occur in the exon 45-55 regions (e.g., exon 51) contained within the rod domain can produce highly functional dystrophin proteins, and many carriers are asymptomatic or display mild symptoms. Furthermore, more than 60% of patients may theoretically be treated by targeting exons in this region of the dystrophin gene (e.g., targeting an exon of dystrophin gene, such as exon 51). Efforts have been made to restore the disrupted dystrophin reading frame in DMD patients by skipping non-essential exon(s) (e.g., exon 51 skipping) during mRNA splicing to produce internally deleted but functional dystrophin proteins. The deletion of internal dystrophin exon(s) (e.g., deletion of exon 51) retains the proper reading frame but cause the less severe Becker muscular dystrophy, or BMD. The Becker muscular dystrophy, or BMD, genotype is similar to DMD in that deletions are present in the dystrophin gene. However, these deletions leave the reading frame intact. Thus an internally truncated but partially functional dystrophin protein is created. BMD has a wide array of phenotypes, but often if deletions are between exons 45-55 of dystrophin the phenotype is much milder compared to DMD. Thus changing a DMD genotype to a BMD genotype is a common strategy to correct dystrophin. There are many strategies to correct dystrophin, many of which rely on restoring the reading frame of the endogenous dystrophin. This shifts the disease genotype from DMD to Becker muscular dystrophy. Many BMD patients have intragenic deletions that maintain the translational reading frame, leading to a shorter but largely functional dystrophin protein.

In certain embodiments, modification of exon 51 (e.g., deletion or excision of exon 51 by, e.g., NHEJ) to restore reading frame ameliorates the phenotype DMD subjects, including DMD subjects with deletion mutations. In certain embodiments, exon 51 of a dystrophin gene refers to the 51$^{st}$ exon of the dystrophin gene. Exon 51 is frequently adjacent to frame-disrupting deletions in DMD patients and has been targeted in clinical trials for oligonucleotide-based exon skipping. A clinical trial for the exon 51 skipping compound eteplirsen reported a significant functional benefit across 48 weeks, with an average of 47% dystrophin positive fibers compared to baseline. Mutations in exon 51 are ideally suited for permanent correction by NHEJ-based genome editing.

The presently disclosed vectors can generate deletions in the dystrophin gene, e.g., the human dystrophin gene. In certain embodiments, the vector is configured to form two double stand breaks (a first double strand break and a second double strand break) in two introns (a first intron and a second intron) flanking a target position of the dystrophin gene, thereby deleting a segment of the dystrophin gene comprising the dystrophin target position. A "dystrophin target position" can be a dystrophin exonic target position or a dystrophin intra-exonic target position, as described herein. Deletion of the dystrophin exonic target position can optimize the dystrophin sequence of a subject suffering from Duchenne muscular dystrophy, e.g., it can increase the function or activity of the encoded dystrophin protein, or results in an improvement in the disease state of the subject. In certain embodiments, excision of the dystrophin exonic target position restores reading frame. The dystrophin exonic target position can comprise one or more exons of the dystrophin gene. In certain embodiments, the dystrophin target position comprises exon 51 of the dystrophin gene (e.g., human dystrophin gene).

A presently disclosed genetic construct (e.g., a vector) can mediate highly efficient gene editing at exon 51 of a dystrophin gene (e.g., the human dystrophin gene). A presently disclosed genetic construct (e.g., a vector) can restore dystrophin protein expression in cells from DMD patients. Exon 51 is frequently adjacent to frame-disrupting deletions in DMD. Elimination of exon 51 from the dystrophin transcript by exon skipping can be used to treat approximately 15% of all DMD patients. This class of dystrophin mutations is ideally suited for permanent correction by NHEJ-based genome editing and HDR. The genetic constructs (e.g., vectors) described herein have been developed for targeted modification of exon 51 in the human dystrophin gene. A presently disclosed genetic construct (e.g., a vector) is transfected into human DMD cells and mediates efficient gene modification and conversion to the correct reading frame. Protein restoration is concomitant with frame restoration and detected in a bulk population of CRISPR/Cpf1-based gene editing system-treated cells.

Single or multiplexed gRNAs can be designed to restore the dystrophin reading frame by targeting the mutational hotspot at exon 51 or and introducing either intraexonic small insertions and deletions, or excision of exon 51. Following treatment with a presently disclosed vector, dystrophin expression can be restored in Duchenne patient muscle cells in vitro. Human dystrophin was detected in vivo following transplantation of genetically corrected patient cells into immunodeficient mice. Significantly, the unique multiplex gene editing capabilities of the CRISPR/Cpf1-based gene editing system enable efficiently generating large deletions of this mutational hotspot region that can correct up to 62% of patient mutations by universal or patient-specific gene editing approaches. In some embodiments, candidate gRNAs are evaluated and chosen based on off-target activity, on-target activity as measured by surveyor, and distance from the exon.

The Cpf1 gRNA may target a region of the dystrophin gene (DMD). In certain embodiments, the Cpf1 gRNA can target at least one of exons, introns, the promoter region, the enhancer region, splice acceptor sites, and/or the transcribed region of the dystrophin gene. In some embodiments, the target region comprises a polynucleotide sequence of at least one of SEQ ID NOs: 1-28. In certain embodiments, the Cpf1 gRNA targets intron 50 of the human dystrophin gene. In certain embodiments, the Cpf1 gRNA targets intron 51 of the human dystrophin gene. In certain embodiments, the Cpf1 gRNA targets exon 51 of the human dystrophin gene. The Cpf1 gRNA may include a polynucleotide sequence of any one of SEQ ID NO: 36-64, 71-119, a fragment of any one of SEQ ID NOs: 36-64, 71-119, or a complement thereof.

4. CRISPR/Cpf1-BASED GENE EDITING SYSTEM GENETIC CONSTRUCTS FOR GENOME EDITING OF B-CELL LYMPHOMA/LEUKEMIA 11A (BCL11a) GENE

Sickle cell anemia (SCA) is caused by a point mutation in the β-globin gene, and β-thalassemia is caused by other mutations leading to loss of β-globin expression. BCL11a is a transcriptional repressor that silences embryonic and fetal globin genes. Complete loss of BCL11a is embryonically lethal; however, disrupting the erythroid-specific enhancer region of BCL11a may reduce the abundance of the transcriptional repressor and increase fetal globin levels improving phenotype of the disease. Similarly, a particular mutation to the γ-globin (HBG1/2) promoter leads to loss of transcriptional repression and hereditary persistence of fetal hemoglobin (HPFH). The larger indel footprint generated by Cpf1 can efficiently disrupt the enhancer region of BCL11a or repression regions of HBG1/2. In some embodiments, the Cpf1 gRNAs is designed to disrupt the enhancer region of BCL11a, increase fetal globin levels, and improve phenotype of SCA. In some embodiments, the enhancer region comprises a polynucleotide sequence of at least one of SEQ ID NOs: 29-35. In some embodiments, the Cpf1 gRNA comprises a polynucleotide sequence of any one of SEQ ID NOs: 65-70, a fragment of any one of SEQ ID NOs: 65-70, or a complement thereof.

5. DNA TARGETING COMPOSITIONS

The present invention is also directed to DNA targeting compositions that comprise such genetic constructs. The DNA targeting compositions include at least one Cpf1 gRNA (e.g., one Cpf1 gRNA, two Cpf1 gRNAs, three gRNAs, etc.) that targets a dystrophin gene (e.g., human dystrophin gene), as described above. The at least one Cpf1 gRNA can bind and recognize a target region. The target regions can be chosen immediately upstream of possible out-of-frame stop codons such that insertions or deletions during the repair process restore the dystrophin reading frame by frame conversion. Target regions can also be splice acceptor sites or splice donor sites, such that insertions or deletions during the repair process disrupt splicing and restore the dystrophin reading frame by splice site disruption and exon exclusion. Target regions can also be aberrant stop codons such that insertions or deletions during the repair process restore the dystrophin reading frame by eliminating or disrupting the stop codon.

In certain embodiments, the presently disclosed DNA targeting composition includes a first Cpf1 gRNA and a second Cpf1 gRNA, wherein the first Cpf1 gRNA and the second Cpf1 gRNA comprise a polynucleotide sequence set forth in SEQ ID NOs: 36-119, or a complement thereof. In some embodiments the polynucleotide sequence comprises at least one of SEQ ID NOs: 36-64, 71-119, or a complement thereof. In some embodiments the polynucleotide sequence comprises at least one of SEQ ID NOs: 65-70, or a complement thereof. In certain embodiments, the first Cpf1 gRNA and the second Cpf1 gRNA comprise polynucleotide sequences.

In certain embodiments, the first Cpf1 gRNA and the second Cpf1 gRNA are selected from the group consisting of: (i) a first Cpf1 gRNA comprising a polynucleotide sequence set forth in SEQ ID NO: 54, and a second Cpf1 gRNA comprising a polynucleotide sequence set forth in SEQ ID NO: 62; (ii) a first Cpf1 gRNA comprising a polynucleotide sequence set forth in SEQ ID NO: 55, and a second Cpf1 gRNA comprising a polynucleotide sequence set forth in SEQ ID NO: 63; and (iii) a first Cpf1 gRNA comprising a polynucleotide sequence set forth in SEQ ID NO: 56, and a second Cpf1 gRNA comprising a polynucleotide sequence set forth in SEQ ID NO: 61.

In certain embodiments, the DNA targeting composition may further include at least one Cpf1 endonuclease that recognizes a PAM of TTTA (SEQ ID NO: 120), TTTG (SEQ ID NO: 121), TTTC (SEQ ID NO: 122), or TTTT (SEQ ID NO: 123). In some embodiments, the DNA targeting composition includes a Cpf1 endonuclease encoded by a polynucleotide sequence set forth in SEQ ID NO: 124 or SEQ ID NO: 125. In certain embodiments, the vector is configured to form a first and a second double strand break in a first and a second intron flanking exon 51 of the human dystrophin gene, respectively, thereby deleting a segment of the dystrophin gene comprising exon 51.

The deletion efficiency of the presently disclosed vectors can be related to the deletion size, i.e., the size of the segment deleted by the vectors. In certain embodiments, the length or size of specific deletions is determined by the distance between the PAM sequences in the gene being targeted (e.g., a dystrophin gene). In certain embodiments, a specific deletion of a segment of the dystrophin gene, which is defined in terms of its length and a sequence it comprises (e.g., exon 51), is the result of breaks made adjacent to specific PAM sequences within the target gene (e.g., a dystrophin gene).

In certain embodiments, the deletion size is about 50 to about 2,000 base pairs (bp), e.g., about 50 to about 1999 bp, about 50 to about 1900 bp, about 50 to about 1800 bp, about 50 to about 1700 bp, about 50 to about 1650 bp, about 50 to about 1600 bp, about 50 to about 1500 bp, about 50 to about 1400 bp, about 50 to about 1300 bp, about 50 to about 1200 bp, about 50 to about 1150 bp, about 50 to about 1100 bp, about 50 to about 1000 bp, about 50 to about 900 bp, about 50 to about 850 bp, about 50 to about 800 bp, about 50 to about 750 bp, about 50 to about 700 bp, about 50 to about 600 bp, about 50 to about 500 bp, about 50 to about 400 bp, about 50 to about 350 bp, about 50 to about 300 bp, about 50 to about 250 bp, about 50 to about 200 bp, about 50 to about 150 bp, about 50 to about 100 bp, about 100 to about 1999 bp, about 100 to about 1900 bp, about 100 to about 1800 bp, about 100 to about 1700 bp, about 100 to about 1650 bp, about 100 to about 1600 bp, about 100 to about 1500 bp, about 100 to about 1400 bp, about 100 to about 1300 bp, about 100 to about 1200 bp, about 100 to about 1150 bp, about 100 to about 1100 bp, about 100 to about 1000 bp, about 100 to about 900 bp, about 100 to about 850 bp, about 100 to about 800 bp, about 100 to about 750 bp, about 100 to about 700 bp, about 100 to about 600 bp, about 100 to about 1000 bp, about 100 to about 400 bp, about 100 to about 350 bp, about 100 to about 300 bp, about 100 to about 250 bp, about 100 to about 200 bp, about 100 to about 150 bp, about 200 to about 1999 bp, about 200 to about 1900 bp, about 200 to about 1800 bp, about 200 to about 1700 bp, about 200 to about 1650 bp, about 200 to about 1600 bp, about 200 to about 1500 bp, about 200 to about 1400 bp, about 200 to about 1300 bp, about 200 to about 1200 bp, about 200 to about 1150 bp, about 200 to about 1100 bp, about 200 to about 1000 bp, about 200 to about 900 bp, about 200 to about 850 bp, about 200 to about 800 bp, about 200 to about 750 bp, about 200 to about 700 bp, about 200 to about 600 bp, about 200 to about 2000 bp, about 200 to about 400 bp, about 200 to about 350 bp, about 200 to about 300 bp, about 200 to about 250 bp, about 300 to about 1999 bp, about 300 to about 1900 bp, about 300 to about 1800 bp, about 300 to about 1700 bp, about 300 to about 1650 bp, about 300 to about 1600 bp, about 300 to about 1500 bp, about 300 to about 1400 bp, about 300 to about 1300 bp, about 300 to about 1200 bp, about 300 to about 1150 bp, about 300 to about 1100 bp, about 300 to about 1000 bp, about 300 to about 900 bp, about 300 to about 850 bp, about 300 to about 800 bp, about 300 to about 750 bp, about 300 to about 700 bp, about 300 to about 600 bp, about 300 to about 3000 bp, about 300 to about 400 bp, or about 300 to about 350 bp. In certain embodiments, the deletion size can be about 118 base pairs, about 233 base pairs, about 326 base pairs, about 766 base pairs, about 805 base pairs, or about 1611 base pairs.

6. COMPOSITIONS FOR GENOME EDITING IN MUSCLE

The present invention is directed to genetic constructs (e.g., vectors) or a composition thereof for genome editing a target gene in skeletal muscle or cardiac muscle of a subject. The composition includes a modified AAV vector and a polynucleotide sequence encoding a CRISPR/Cpf1-based gene editing system, e.g., a Cpf1 gRNA and a Cpf1 endonuclease. The composition delivers active forms of CRISPR/Cpf1-based gene editing systems to skeletal muscle or cardiac muscle. The presently disclosed genetic constructs (e.g., vectors) can be used in correcting or reducing the effects of mutations in the dystrophin gene involved in genetic diseases and/or other skeletal or cardiac muscle conditions, e.g., DMD. The composition may further comprise a donor DNA or a transgene. These compositions may be used in genome editing, genome engineering, and correcting or reducing the effects of mutations in genes involved in genetic diseases and/or other skeletal or cardiac muscle conditions.

a. CRISPR/Cpf1-Based Gene Editing System for Targeting Dystrophin

A CRISPR/Cpf1-based gene editing system specific for dystrophin gene are disclosed herein. The CRISPR/Cpf1-based gene editing system may include Cpf1 endonuclease and at least one Cpf1 gRNA to target the dystrophin gene. The CRISPR/Cpf1-based gene editing system may bind and recognize a target region. The target regions may be chosen immediately upstream of possible out-of-frame stop codons such that insertions or deletions during the repair process restore the dystrophin reading frame by frame conversion. Target regions may also be splice acceptor sites or splice donor sites, such that insertions or deletions during the repair process disrupt splicing and restore the dystrophin reading frame by splice site disruption and exon exclusion. Target regions may also be aberrant stop codons such that insertions or deletions during the repair process restore the dystrophin reading frame by eliminating or disrupting the stop codon.

The Cpf1 gRNA may target a polynucleotide sequence selected from the group consisting of SEQ ID NO: 1-35, or a complement thereof. For example, the disclosed CRISPR/Cpf1-based gene editing systems were engineered to mediate highly efficient gene editing at exon 51 of the dystrophin gene. These CRISPR/Cpf1-based gene editing systems restored dystrophin protein expression in cells from DMD patients.

b. Adeno-Associated Virus Vectors

The composition may also include a viral delivery system. In certain embodiments, the vector is an adeno-associated virus (AAV) vector. The AAV vector is a small virus belonging to the genus Dependovirus of the Parvoviridae family that infects humans and some other primate species. AAV vectors may be used to deliver CRISPR/Cpf1-based gene editing systems using various construct configurations. For example, AAV vectors may deliver Cpf1 endonucleases and Cpf1 gRNA expression cassettes on separate vectors or on the same vector. Alternatively, both the Cpf1 endonucleases and up to two gRNA expression cassettes may be combined in a single AAV vector within the 4.7 kb packaging limit.

In certain embodiments, the AAV vector is a modified AAV vector. The modified AAV vector may have enhanced cardiac and skeletal muscle tissue tropism. The modified AAV vector may be capable of delivering and expressing the CRISPR/Cpf1-based gene editing system in the cell of a mammal. For example, the modified AAV vector may be an AAV-SASTG vector (Piacentino et al. (2012) Human Gene Therapy 23:635-646). The modified AAV vector may deliver nucleases to skeletal and cardiac muscle in vivo. The modified AAV vector may be based on one or more of several capsid types, including AAV1, AAV2, AAV5, AAV6, AAV8, and AAV9. The modified AAV vector may be based on AAV2 pseudotype with alternative muscle-tropic AAV capsids, such as AAV2/1, AAV2/6, AAV2/7, AAV2/8, AAV2/9, AAV2.5 and AAV/SASTG vectors that efficiently transduce skeletal muscle or cardiac muscle by systemic and local delivery (Seto et al. Current Gene Therapy (2012) 12:139-151). The modified AAV vector may be AAV2i8G9 (Shen et al. J. Biol. Chem. (2013) 288:28814-28823).

7. METHODS OF GENOME EDITING IN MUSCLE

The present disclosure is directed to a method of genome editing in a skeletal muscle or cardiac muscle of a subject. The method comprises administering to the skeletal muscle or cardiac muscle of the subject the composition for genome editing in skeletal muscle or cardiac muscle, as described above. The genome editing may include correcting a mutant gene or inserting a transgene. Correcting the mutant gene may include deleting, rearranging, or replacing the mutant gene. Correcting the mutant gene may include nuclease-mediated NHEJ or HDR.

8. METHODS OF CORRECTING A MUTANT GENE AND TREATING A SUBJECT

The presently disclosed subject matter provides for methods of correcting a mutant gene (e.g., a mutant dystrophin gene, e.g., a mutant human dystrophin gene) in a cell and treating a subject suffering from a genetic disease, such as DMD. The method can include administering to a cell or a subject a presently disclosed genetic construct (e.g., a vector) or a composition comprising thereof as described above. The method can comprises administering to the skeletal muscle or cardiac muscle of the subject the presently disclosed genetic construct (e.g., a vector) or a composition comprising thereof for genome editing in skeletal muscle or cardiac muscle, as described above. Use of presently disclosed genetic construct (e.g., a vector) or a composition comprising thereof to deliver the CRISPR/Cpf1-based gene editing system to the skeletal muscle or cardiac muscle may restore the expression of a full-functional or partially-functional protein with a repair template or donor DNA, which can replace the entire gene or the region containing the mutation. The CRISPR/Cpf1-based gene editing system may be used to introduce site-specific double strand breaks at targeted genomic loci. Site-specific double-strand breaks are created when the CRISPR/Cpf1-based gene editing system binds to a target DNA sequences, thereby permitting cleavage of the target DNA. This DNA cleavage may stimulate the natural DNA-repair machinery, leading to one of two possible repair pathways: homology-directed repair (HDR) or the non-homologous end joining (NHEJ) pathway.

The present disclosure is directed to genome editing with a CRISPR/Cpf1-based gene editing system without a repair template, which can efficiently correct the reading frame and restore the expression of a functional protein involved in a genetic disease. The disclosed CRISPR/Cpf1-based gene editing systems may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active CRISPR/Cpf1-based gene editing systems with an efficient gene editing method for the treatment of genetic diseases caused by mutations in nonessential coding regions that cause frameshifts, premature stop codons, aberrant splice donor sites or aberrant splice acceptor sites.

a. Nuclease Mediated Non-Homologous End Joining

Restoration of protein expression from an endogenous mutated gene may be through template-free NHEJ-mediated DNA repair. In contrast to a transient method targeting the target gene RNA, the correction of the target gene reading frame in the genome by a transiently expressed CRISPR/Cpf1-based gene editing system may lead to permanently restored target gene expression by each modified cell and all of its progeny. In certain embodiments, NHEJ is a nuclease mediated NHEJ, which in certain embodiments, refers to NHEJ that is initiated a Cpf1 endonuclease, cuts double stranded DNA. The method comprises administering a presently disclosed genetic construct (e.g., a vector) or a composition comprising thereof to the skeletal muscle or cardiac muscle of the subject for genome editing in skeletal muscle or cardiac muscle.

Nuclease mediated NHEJ gene correction may correct the mutated target gene and offers several potential advantages over the HDR pathway. For example, NHEJ does not require a donor template, which may cause nonspecific insertional mutagenesis. In contrast to HDR, NHEJ operates efficiently in all stages of the cell cycle and therefore may be effectively exploited in both cycling and post-mitotic cells, such as muscle fibers. This provides a robust, permanent gene restoration alternative to oligonucleotide-based exon skipping or pharmacologic forced read-through of stop codons and could theoretically require as few as one drug treatment. NHEJ-based gene correction using a CRISPR/Cpf1-based gene editing system, as well as other engineered nucleases including meganucleases and zinc finger nucleases, may be combined with other existing ex vivo and in vivo platforms for cell- and gene-based therapies, in addition to the plasmid electroporation approach described here. For example, delivery of a CRISPR/Cpf1-based gene editing system by mRNA-based gene transfer or as purified cell permeable proteins could enable a DNA-free genome editing approach that would circumvent any possibility of insertional mutagenesis.

b. Homology-Directed Repair

Restoration of protein expression from an endogenous mutated gene may involve homology-directed repair. The method as described above further includes administrating a donor template to the cell. The donor template may include a polynucleotide sequence encoding a full-functional protein or a partially-functional protein. For example, the donor template may include a miniaturized dystrophin construct, termed minidystrophin ("minidys"), a full-functional dystrophin construct for restoring a mutant dystrophin gene, or a fragment of the dystrophin gene that after homology-directed repair leads to restoration of the mutant dystrophin gene.

c. Methods of Correcting a Mutant Gene and Treating a Subject Using CRISPR/Cpf1-Based Gene Editing System The present disclosure is also directed to genome editing with the CRISPR/Cpf1-based gene editing system to restore the expression of a full-functional or partially-functional protein with a repair template or donor DNA, which can replace the entire gene or the region containing the mutation. The CRISPR/Cpf1-based gene editing system may be used to introduce site-specific double strand breaks at targeted genomic loci. Site-specific double-strand breaks are created when the CRISPR/Cpf1-based gene editing system binds to a target DNA sequences using the gRNA, thereby permitting cleavage of the target DNA. The CRISPR/Cpf1-based gene editing system has the advantage of advanced genome editing due to their high rate of successful and efficient genetic modification. This DNA cleavage may stimulate the natural DNA-repair machinery, leading to one of two possible repair pathways: homology-directed repair (HDR) or the non-homologous end joining (NHEJ) pathway. For example, a CRISPR/Cpf1-based gene editing system directed towards the dystrophin gene may include a Cpf1 gRNA having a nucleic acid sequence of any one of SEQ ID NOs: 36-64, 71-119, or complement thereof.

The present disclosure is directed to genome editing with CRISPR/Cpf1-based gene editing system without a repair template, which can efficiently correct the reading frame and restore the expression of a functional protein involved in a genetic disease. The disclosed CRISPR/Cpf1-based gene editing system and methods may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active CRISPR/Cpf1-based gene editing system with an efficient gene editing method for the treatment of genetic diseases caused by mutations in nonessential coding regions that cause frameshifts, premature stop codons, aberrant splice donor sites or aberrant splice acceptor sites.

The present disclosure provides methods of correcting a mutant gene in a cell and treating a subject suffering from a genetic disease, such as DMD. The method may include administering to a cell or subject a CRISPR/Cpf1-based gene editing system, a polynucleotide or vector encoding said CRISPR/Cpf1-based gene editing system, or composition of said CRISPR/Cpf1-based gene editing system as described above. The method may include administering a CRISPR/Cpf1-based gene editing system, such as administering a Cpf1 endonuclease, a polynucleotide sequence encoding said Cpf1 endonuclease, and/or at least one Cpf1 gRNA, wherein the gRNAs target different DNA sequences. The target DNA sequences may be overlapping. The number of gRNA administered to the cell may be at least 1 gRNA, at least 2 different gRNA, at least 3 different gRNA at least 4 different gRNA, at least 5 different gRNA, at least 6 different gRNA, at least 7 different gRNA, at least 8 different gRNA, at least 9 different gRNA, at least 10 different gRNA, at least 15 different gRNA, at least 20 different gRNA, at least 30 different gRNA, or at least 50 different gRNA, as described above. The gRNA may include a nucleic acid sequence of at least one of SEQ ID NOs: 36-64, 71-119, or complement thereof. The method may involve homology-directed repair or non-homologous end joining.

9. METHODS OF TREATING DISEASE

The present disclosure is directed to a method of treating a subject in need thereof. The method comprises administering to a tissue of a subject the presently disclosed genetic construct (e.g., a vector) or a composition comprising thereof, as described above. In certain embodiments, the method may comprises administering to the skeletal muscle or cardiac muscle of the subject the presently disclosed genetic construct (e.g., a vector) or composition comprising thereof, as described above. In certain embodiments, the method may comprises administering to a vein of the subject the presently disclosed genetic construct (e.g., a vector) or composition comprising thereof, as described above. In certain embodiments, the subject is suffering from a skeletal muscle or cardiac muscle condition causing degeneration or weakness or a genetic disease. For example, the subject may be suffering from Duchenne muscular dystrophy, as described above.

a. Duchenne Muscular Dystrophy

The method, as described above, may be used for correcting the dystrophin gene and recovering full-functional or partially-functional protein expression of said mutated dystrophin gene. In some aspects and embodiments the disclosure provides a method for reducing the effects (e.g., clinical symptoms/indications) of DMD in a patient. In some aspects and embodiments the disclosure provides a method for treating DMD in a patient. In some aspects and embodiments the disclosure provides a method for preventing DMD in a patient. In some aspects and embodiments the disclosure provides a method for preventing further progression of DMD in a patient.

10. CONSTRUCTS AND PLASMIDS

The compositions, as described above, may comprise genetic constructs that encodes the CRISPR/Cpf1-based gene editing system, as disclosed herein. The genetic construct, such as a plasmid, may comprise a nucleic acid that encodes the CRISPR/Cpf1-based gene editing system, such as the Cpf1 endonuclease and/or at least one of the Cpf1 gRNAs. The compositions, as described above, may comprise genetic constructs that encodes the modified AAV vector and a nucleic acid sequence that encodes the CRISPR/Cpf1-based gene editing system, as disclosed herein. The genetic construct, such as a plasmid, may comprise a nucleic acid that encodes the CRISPR/Cpf1-based gene editing system. The compositions, as described above, may comprise genetic constructs that encodes the modified lentiviral vector, as disclosed herein.

In some embodiments, the genetic construct may comprise a promoter that operably linked to the polynucleotide sequence encoding the at least one Cpf1 gRNA and/or a Cpf1 endonuclease. In some embodiments, the promoter is operably linked to the polynucleotide sequence encoding a first Cpf1 gRNA, a second Cpf1 gRNA, and/or a Cpf1 endonuclease. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer, an initiation codon, a stop codon, or a polyadenylation signal.

In certain embodiments, the genetic construct is a vector. The vector can be an Adeno-associated virus (AAV) vector, which encode at least one Cpf1 endonuclease and at least one Cpf1 gRNA; the vector is capable of expressing the at least one Cpf1 endonuclease and the at least one Cpf1 gRNA, in the cell of a mammal. The vector can be a plasmid. The vectors can be used for in vivo gene therapy. The vector may be recombinant. The vector may comprise heterologous nucleic acid encoding the CRISPR/Cpf1-based gene editing system. The vector may be a plasmid. The vector may be useful for transfecting cells with nucleic acid encoding the CRISPR/Cpf1-based gene editing system, which the transformed host cell is cultured and maintained under conditions wherein expression of the CRISPR/Cpf1-based gene editing system takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the CRISPR/Cpf1-based gene editing system and may further comprise an initiation codon, which may be upstream of the CRISPR/Cpf1-based gene editing system coding sequence, and a stop codon, which may be downstream of the CRISPR/Cpf1-based gene editing system coding sequence. The initiation and termination codon may be in frame with the CRISPR/Cpf1-based gene editing system coding sequence. The vector may also comprise a promoter that is operably linked to the CRISPR/Cpf1-based gene editing system coding sequence. The promoter that is operably linked to the CRISPR/Cpf1-based gene editing system coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, a U6 promoter, such as the human U6 promoter, or a Rous sarcoma virus (RSV) promoter. The promoter may also be a promoter from a human gene such as human ubiquitin C (hUbC), human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication Nos. US20040175727 and US20040192593, the contents of which are incorporated herein in their entirety. Examples of muscle-specific promoters include a Spc5-12 promoter (described in US Patent Application Publication No. US 20040192593, which is incorporated by reference herein in its entirety; Hakim et al. Mol. Ther. Methods Clin. Dev. (2014) 1:14002: and Lai et al. Hum Mol Genet. (2014) 23(12): 3189-3199), a MHCK7 promoter (described in Salva et al., Mol. Ther. (2007) 15:320-329), a CK8 promoter (described in Park et al. PLoS ONE (2015) 10(4): e0124914), and a CK8e promoter (described in Muir et al., Mol. Ther. Methods Clin. Dev. (2014) 1:14025). In some embodiments, the expression of the gRNA and/or Cpf1 endonuclease is driven by tRNAs.

Each of the polynucleotide sequences encoding the Cpf1 gRNA and/or Cpf1 endonuclease may each be operably linked to a promoter. The promoters that are operably linked to the Cpf1 gRNA and/or Cpf1 endonuclease may be the same promoter. The promoters that are operably linked to the Cpf1 gRNA and/or Cpf1 endonuclease may be different promoters. The promoter may be a constitutive promoter, an inducible promoter, a repressible promoter, or a regulatable promoter.

The vector may also comprise a polyadenylation signal, which may be downstream of the CRISPR/Cpf1-based gene editing system. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, Calif.).

The vector may also comprise an enhancer upstream of the CRISPR/Cpf1-based gene editing system, i.e., the Cpf1 endonuclease coding sequence, Cpf1 gRNAs, or the CRISPR/Cpf1-based gene editing system. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the CRISPR/Cpf1-based gene editing system, including the nucleic acid sequence encoding the Cpf1 endonuclease and the nucleic acid sequence encoding the at least one Cpf1 gRNA comprising the nucleic acid sequence of at least one of SEQ ID NOs: 36-119, or complement thereof.

11. PHARMACEUTICAL COMPOSITIONS

The presently disclosed subject matter provides for compositions comprising the above-described genetic constructs. The pharmaceutical compositions according to the present invention can be formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the composition for genome editing in skeletal muscle or cardiac muscle at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the composition may also include a transfection facilitating agent such as lipids, liposomes, including lecithin liposomes or other liposomes known in the art, as a DNA-liposome mixture (see for example International Patent Publication No. WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

12. METHODS OF DELIVERY

Provided herein is a method for delivering the presently disclosed genetic construct (e.g., a vector) or a composition thereof to a cell. The delivery of the compositions may be the transfection or electroporation of the composition as a nucleic acid molecule that is expressed in the cell and delivered to the surface of the cell. The nucleic acid molecules may be electroporated using BioRad Gene Pulser Xcell or Amaxa Nucleofector IIb devices. Several different buffers may be used, including BioRad electroporation solution, Sigma phosphate-buffered saline product #D8537 (PBS), Invitrogen OptiMEM I (OM), or Amaxa Nucleofector solution V (N. V.). Transfections may include a transfection reagent, such as Lipofectamine 2000.

Upon delivery of the presently disclosed genetic construct or composition to the tissue, and thereupon the vector into the cells of the mammal, the transfected cells will express the Cpf1 gRNA(s) and the Cpf1 endonuclease. The genetic construct or composition may be administered to a mammal to alter gene expression or to re-engineer or alter the genome. For example, the genetic construct or composition may be administered to a mammal to correct the dystrophin gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

The genetic construct (e.g., a vector) encoding the Cpf1 gRNA(s) and the Cpf1 endonuclease can be delivered to the mammal by DNA injection (also referred to as DNA vaccination) with and without in vivo electroporation, liposome mediated, nanoparticle facilitated, and/or recombinant vectors. The recombinant vector can be delivered by any viral mode. The viral mode can be recombinant lentivirus, recombinant adenovirus, and/or recombinant adeno-associated virus.

A presently disclosed genetic construct (e.g., a vector) or a composition comprising thereof can be introduced into a cell to genetically correct a dystrophin gene (e.g., human dystrophin gene). In certain embodiments, a presently disclosed genetic construct (e.g., a vector) or a composition comprising thereof is introduced into a myoblast cell from a DMD patient. In certain embodiments, the genetic construct (e.g., a vector) or a composition comprising thereof is introduced into a fibroblast cell from a DMD patient, and the genetically corrected fibroblast cell can be treated with MyoD to induce differentiation into myoblasts, which can be implanted into subjects, such as the damaged muscles of a subject to verify that the corrected dystrophin protein is functional and/or to treat the subject. The modified cells can also be stem cells, such as induced pluripotent stem cells, bone marrow-derived progenitors, skeletal muscle progenitors, human skeletal myoblasts from DMD patients, CD 133$^+$ cells, mesoangioblasts, and MyoD- or Pax7-transduced cells, or other myogenic progenitor cells. For example, the CRISPR/Cpf1-based gene editing system may cause neuronal or myogenic differentiation of an induced pluripotent stem cell.

13. ROUTES OF ADMINISTRATION

The presently disclosed genetic constructs (e.g., vectors) or a composition comprising thereof may be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. In certain embodiments, the presently disclosed genetic construct (e.g., a vector) or a composition is administered to a subject (e.g., a subject suffering from DMD) intramuscularly, intravenously or a combination thereof. For veterinary use, the presently disclosed genetic constructs (e.g., vectors) or compositions may be administered as a suitably acceptable formulation in accordance with normal veterinary practice. The veterinarian may readily determine the dosing regimen and route of administration that is most appropriate for a particular animal. The compositions may be administered by traditional syringes, needleless injection devices, "microprojectile bombardment gone guns", or other physical methods such as electroporation ("EP"), "hydrodynamic method", or ultrasound.

The presently disclosed genetic construct (e.g., a vector) or a composition may be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus. The composition may be injected into the skeletal muscle or cardiac muscle. For example, the composition may be injected into the tibialis anterior muscle or tail.

In some embodiments, the presently disclosed genetic construct (e.g., a vector) or a composition thereof is administered by 1) tail vein injections (systemic) into adult mice; 2) intramuscular injections, for example, local injection into a muscle such as the TA or gastrocnemius in adult mice; 3) intraperitoneal injections into P2 mice; or 4) facial vein injection (systemic) into P2 mice.

14. CELL TYPES

Any of these delivery methods and/or routes of administration can be utilized with a myriad of cell types, for example, those cell types currently under investigation for cell-based therapies of DMD, including, but not limited to, immortalized myoblast cells, such as wild-type and DMD patient derived lines, for example Δ48-50 DMD, DMD 6594 (del48-50), DMD 8036 (del48-50), C25C14 and DMD-7796 cell lines, primal DMD dermal fibroblasts, induced pluripotent stem cells, bone marrow-derived progenitors, skeletal muscle progenitors, human skeletal myoblasts from DMD patients, CD 133$^+$ cells, mesoangioblasts, cardiomyocytes, hepatocytes, chondrocytes, mesenchymal progenitor cells, hematopoetic stem cells, smooth muscle cells, and MyoD- or Pax7-transduced cells, or other myogenic progenitor cells. Immortalization of human myogenic cells can be used for clonal derivation of genetically corrected myogenic cells. Cells can be modified ex vivo to isolate and expand clonal populations of immortalized DMD myoblasts that include a genetically corrected dystrophin gene and are free of other nuclease-introduced mutations in protein coding regions of the genome. Alternatively, transient in vivo delivery of CRISPR/Cpf1-based systems by non-viral or non-integrating viral gene transfer, or by direct delivery of purified proteins and gRNAs containing cell-penetrating motifs may enable highly specific correction in situ with minimal or no risk of exogenous DNA integration.

15. KITS

Provided herein is a kit, which may be used to correct a mutated dystrophin gene. The kit comprises at least one Cpf1 gRNA for correcting a mutated dystrophin gene and instructions for using the CRISPR/Cpf1-based gene editing system. Also provided herein is a kit, which may be used for genome editing of a dystrophin gene in skeletal muscle or cardiac muscle. The kit comprises genetic constructs (e.g., vectors) or a composition comprising thereof for genome editing in skeletal muscle or cardiac muscle, as described above, and instructions for using said composition.

Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The genetic constructs (e.g., vectors) or a composition comprising thereof for correcting a mutated dystrophin or genome editing of a dystrophin gene in skeletal muscle or cardiac muscle may include a modified AAV vector that includes a Cpf1 gRNA(s) and a Cpf1 endonuclease, as described above, that specifically binds and cleaves a region of the dystrophin gene. The CRISPR/Cpf1-based gene editing system, as described above, may be included in the kit to specifically bind and target a particular region in the mutated dystrophin gene. The kit may further include donor DNA, a different gRNA, or a transgene, as described above.

The kit can also optionally include one or more components, such as reagents required to use the disclosed compositions or to facilitate quality control evaluations, such as standards, buffers, diluents, salts, enzymes, enzyme co-factors, substrates, detection reagents, and the like. Other components, such as buffers and solutions for the isolation and/or treatment of the cells, also can be included in the kit. The kit can additionally include one or more other controls. One or more of the components of the kit can be lyophilized, in which case the kit can further comprise reagents suitable for the reconstitution of the lyophilized components.

16. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present invention has multiple aspects, illustrated by the following non-limiting examples.

Example 1

Guide RNA Design and Material Preparation

Cpf1 from *Acidaminococcus* was obtained from the Addgene non-profit plasmid repository (pY010 (pcDNA3.1-hAsCpf1; "the AsCPF1 plasmid") from Feng Zhang (Addgene plasmid #69982)). The AsCPF1 plasmid was transformed into chemically competent *E. coli* and amplified, after which the sequence was verified. Cpf1 guide RNAs (also known as Cpf1 crRNAs) were designed with the University of California Santa Cruz Genome Browser program to target splice sites on prevalent exon mutations in dystrophin and the BCL11a enhancer, ordered as oligomers from Integrated DNA Technologies (IDT), prepared with PCR, and column purified as previously described (Zetsche et al., Cell 163(3):759-71 (2015)).

Guide RNA validation. Transfections were performed with Lipofectamine 2000 in 24-well plates of HEK293 cells (ATCC) following manufacturer's recommendations. Each well received 400 ng of AsCPF1 plasmid and 100 ng U6::sgRNA PCR products. After 72 hours, cells were isolated and genomic DNA was purified with a DNeasy column (QIAGEN). Surveyor nuclease digestion (IDT) and deletion PCR was performed with primers flanking the genomic region of interest as previously described (Ousterout et al., Nature Communications 6:6244 (2015); Guschin et al., Methods Mol. Biol. 649:247-256 (2010)). Digested PCR products were electrophoresed in TBE gels (Invitrogen) for 30 min at 200V, stained with ethidium bromide (EtBr), and imaged on a Gel Doc™ (Biorad). Deletion PCR products were electrophoresed in 1% agarose gels for 30 min at 120V, stained with EtBr, and imaged on a Gel Doc™ (Biorad).

Example 2

Figure 2:
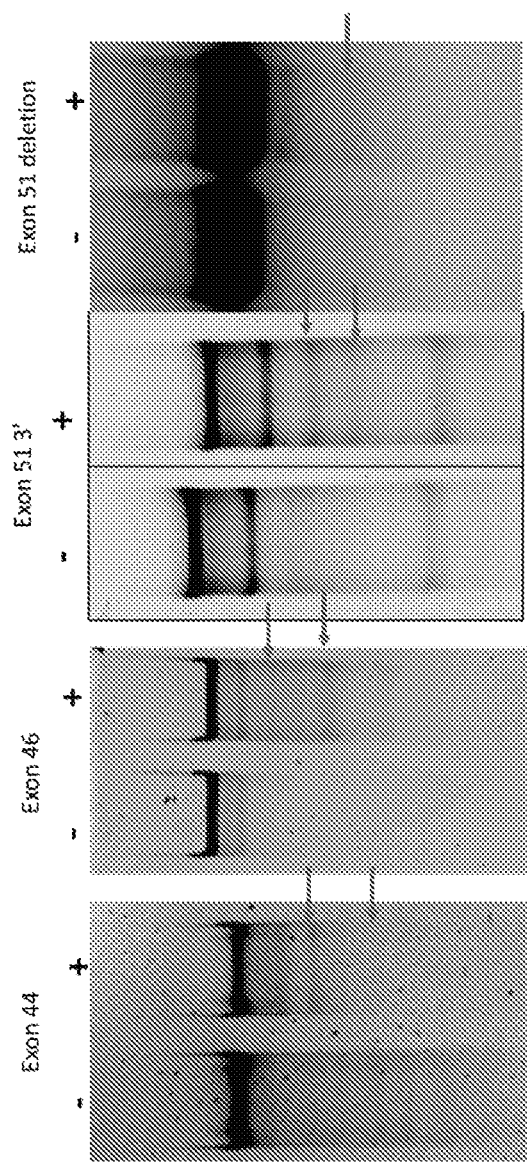
FIG. 2 shows blots showing exon 44, 46 and 51 are targeted gRNAs with detectable activity in accordance with several embodiments of the present disclosure.

Dystrophin Splice-Acceptor Guide RNA 15 guide RNAs targeting the top-ranking highly-mutated dystrophin exons were designed by targeting the cut region as close to the splice acceptor as possible permitted by the presence of an available PAM (Table 1). If possible, multiple guide RNAs were targeted to the same splice acceptor. Candidate guide RNAs were screened in vitro. Guide RNAs that showed immediate positive results include those targeting exon 44, exon 46, and exon 51 (FIGS. 2A-2C). Surveyor nuclease digestion was detected in guide RNAs targeting exon 44 splice acceptor (FIG. 2A), exon 46 splice acceptor (FIG. 2B), and the 3' end of exon 51 (FIG. 2C). FIG. 2D shows that genetic deletions can be created with a guide RNA targeting the splice acceptor of exon 51 and the 3' end of exon 51 implying activity of the exon 51 targeted guide RNA.

Table 1 shows the design of guide RNAs targeting dystrophin exons. The PAM sequence (TTTN) is underlined. Sense guide-RNAs have TTTN on 5' end. Guide RNAs on the antisense strand have NAAA PAMs on the 3' end.

Example 3

Matched Overhang Deletions of Exon 51

Figure 3:
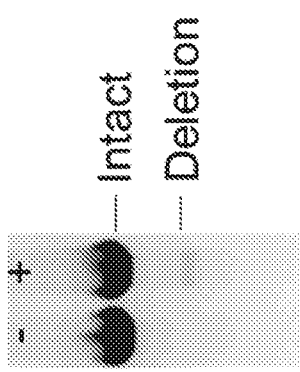
FIG. 3 shows a blot showing 42 guide RNA pairs are screened targeting exon 51 deletion in accordance with one embodiment of the present disclosure.

To determine if guide RNAs with matched overhang sequences encourage seamless deletions, 6 guide RNAs were designed within intron 50 and 7 guide RNAs were designed within intron 51 (Table 2) to generate matched overhang deletions. 42 unique gRNA pairs (6×7) were tested and screened for deletion activity, i.e., targeting exon 51 deletions. Included within this set were three overhang-matched pairs (see Table 2). 7 pairs were validated for activity. FIG. 3 is a representative image showing a smaller band indicating the deletion of exon 51. These results show for the first time Cpf1-targeted splice-acceptor disruption and deletion of exon 51 of the dystrophin gene.

TABLE 1

| Target Sequence | Guide RNA | SEQ ID NO: | Target Exon |
|---|---|---|---|
| TTTGCAAAAACCCAAAATATTTTAGCT (SEQ ID NO: 1) | CAAAAACCCAAAATATTTTAGCT | 36 | Exon 51 |
| TTTGCCTTTTTGGTATCTTACAGGAAC (SEQ ID NO: 2) | CCTTTTTGGTATCTTACAGGAAC | 37 | Exon 45 |
| TCCAGGATGGCATTGGGCAGCGGCAAA (SEQ ID NO: 3) | CCGCTGCCCAATGCCATCCTGGA | 38 | Exon 45 |
| TTTATTTTTCCTTTTATTCTAGTTGAA (SEQ ID NO: 4) | TTTTTCCTTTTATTCTAGTTGAA | 39 | Exon 53 |
| TTTCTTGATCCATATGCTTTTACCTGC (SEQ ID NO: 5) | TTGATCCATATGCTTTTACCTGC | 40 | Exon 44 |
| AGGCGATTTGACAGATCTGTTGAGAAA (SEQ ID NO: 6) | TCAACAGATCTGTCAAATCGCCT | 41 | Exon 44 |
| TTTATTCTTCTTTCTCCAGGCTAGAAG (SEQ ID NO: 7) | TTCTTCTTTCTCCAGGCTAGAAG | 42 | Exon 46 |
| TTCTTTCTCCAGGCTAGAAGAACAAAA (SEQ ID NO: 8) | GTTCTTCTAGCCTGGAGAAAGAA | 43 | Exon 46 |
| TACAGGCAACAATGCAGGATTTGGAAC (SEQ ID NO: 9) | CAAATCCTGCATTGTTGCCTGTA | 44 | Exon 52 |
| TTTTCTGTTAAAGAGGAAGTTAGAAGA (SEQ ID NO: 10) | CTGTTAAAGAGGAAGTTAGAAGA | 45 | Exon 50 |
| TTTTAAAATTTTTATATTACAGAATAT (SEQ ID NO: 11) | AAAATTTTTATATTACAGAATAT | 46 | Exon 43 |
| AGAATATAAAAGATAGTCTACAACAAA (SEQ ID NO: 12) | TTGTAGACTATCTTTTATATTCT | 47 | Exon 43 |
| TTTATTTTGCATTTTAGATGAAAGAGA (SEQ ID NO: 13) | TTTTGCATTTTAGATGAAAGAGA | 48 | Exon 2 |
| TTTTAGATGAAAGAGAAGATGTTCAAA (SEQ ID NO: 14) | AACATCTTCTCTTTCATCTAAAA | 49 | Exon 2 |
| GATGAAAGAGAAGATGTTCAAAAGAA A (SEQ ID NO: 15) | TTTTGAACATCTTCTCTTTCATC | 50 | Exon 2 |

TABLE 2

CPF1 guide RNAs targeting regions flanking exon 51

| TARGET SEQUENCE | Guide RNA | SEQ ID NO: | TARGET | |
|---|---|---|---|---|
| TTTGCAAAAACCCAAAATATTTTAGCT (SEQ ID NO: 16) | CAAAAACCCAAAATATTTTAGCT | 51 | Intron 50 | |
| TTTAGCTTGTGTTTCTAATTTTTCTTT (SEQ ID NO: 17) | GCTTGTGTTTCTAATTTTTCTTT | 52 | Intron 50 | |
| TTTGACTTATTGTTATTGAAATTGGCT (SEQ ID NO: 18) | ACTTATTGTTATTGAAATTGGCT | 53 | Intron 50 | |
| TTTCTACCATGTATTGCTAAACAAAGT (SEQ ID NO: 19) | TACCATGTATTGCTAAACAAAGT | 54 | Intron 50 | Matched pair 1 |
| TTTAGTATCAATTCACACCAGCAAGTT (SEQ ID NO: 20) | GTATCAATTCACACCAGCAAGTT | 55 | Intron 50 | Matched pair 2 |
| ATAATCGCCACTTTACAGAGGAGTAAA (SEQ ID NO: 21) | CTCCTCTGTAAAGTGGCGATTAT | 56 | Intron 50 | Matched pair 3 |
| TTTCTTTAAAATGAAGATTTTCCACCA (SEQ ID NO: 22) | TTTAAAATGAAGATTTTCCACCA | 57 | Intron 51 | |
| TTTAAAATGAAGATTTTCCACCAATCA (SEQ ID NO: 23) | AAATGAAGATTTTCCACCAATCA | 58 | Intron 51 | |
| TTTTCCACCAATCACTTTACTCTCCTA (SEQ ID NO: 24) | CCACCAATCACTTTACTCTCCTA | 59 | Intron 51 | |
| TTTCCCACCAGTTCTTAGGCAACTGTT (SEQ ID NO: 25) | CCACCAGTTCTTAGGCAACTGTT | 60 | Intron 51 | |
| ATAATCAAGGATATAAATTAATGCAAA (SEQ ID NO: 26) | CATTAATTTATATCCTTGATTAT | 61 | Intron 51 | Matched pair 3 |
| TTTTGTTGTTGTTGTTAAGGTCAAAGT (SEQ ID NO: 27) | GTTGTTGTTGTTAAGGTCAAAGT | 62 | Intron 51 | Matched pair 1 |
| TTTAAAATTACCCTAGATCTTAAAGTT (SEQ ID NO: 28) | AAATTACCCTAGATCTTAAAGTT | 63 | Intron 51 | Matched pair 2 |

Example 4

Targeted Deletion of Exon 51 in Patient Derived Myoblasts

Figure 4:
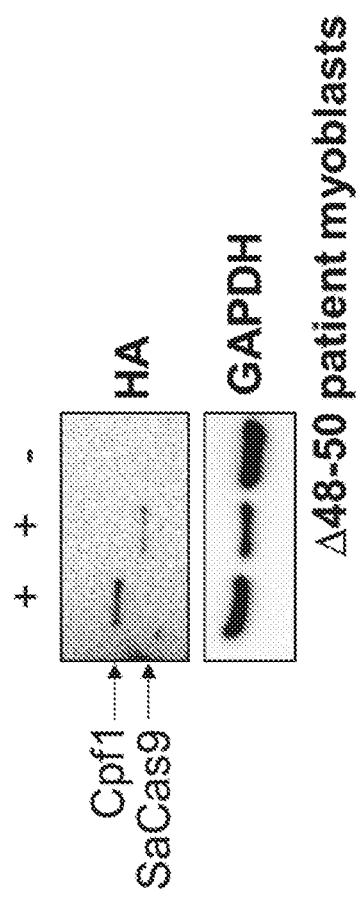
FIG. 4 shows SaCas9 and LbCpf1 are expressed in patient derived myoblasts.
Figure 5:
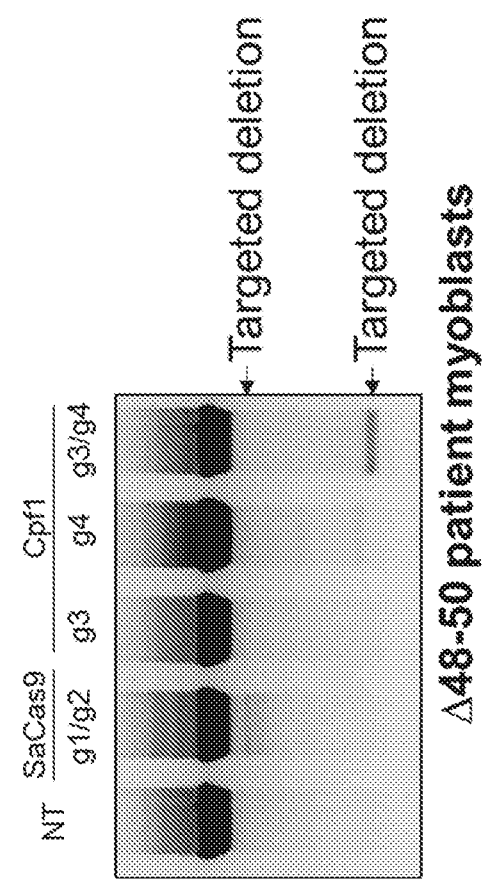
FIG. 5 shows genomic deletions generated by SaCas9 or LbCpf1 in patient myoblasts.

Patient derived myoblasts with an exon 48-50 deletion (Δ48-50) were cultured in skeletal muscle growth media. Electroporations were conducted according to standard lab procedure. Cells were cultured for 3 days and evaluated for protein expression (FIG. 4) and genomic deletion generated by SaCas9 (Cas9 from *Staphylococcus aureus*) or LbCpf1 (CPF1 from *Lachnospiraceae bacterium* ND2006) in patient myoblasts (FIG. 5). FIG. 4 shows a western blot for the HA-tagged SaCas9 and LbCpf1 show expression in extracted protein 72 hours after plasmid transfection. FIG. 5 shows PCR across the targeted genomic region shows a smaller band in bulk-treated myoblasts with SaCas9 gRNAs or Cpf1 crRNAs consistent with removal of exon 51 and portions of the surrounding introns.

Figure 6:
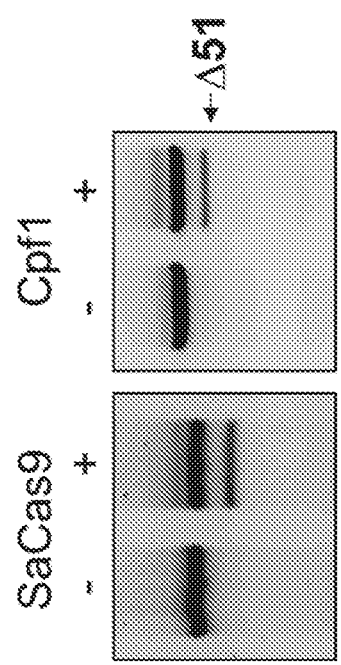
FIG. 6 shows SaCas9 or LbCpf1 targeting exon 51 remove the exon from the transcript.

Myoblasts were then differentiated and evaluated for dystrophin transcript expression and deletion of exon 51 (FIG. 6). FIG. 6 shows that differentiated myoblasts expressed a dystrophin transcript with an absent exon 51 as indicated by the smaller bands produced by RT-PCR, thus indicating that SaCas9 or LbCpf1 targeting of exon 51 removed exon 51 exon from the transcript.

Figure 7:
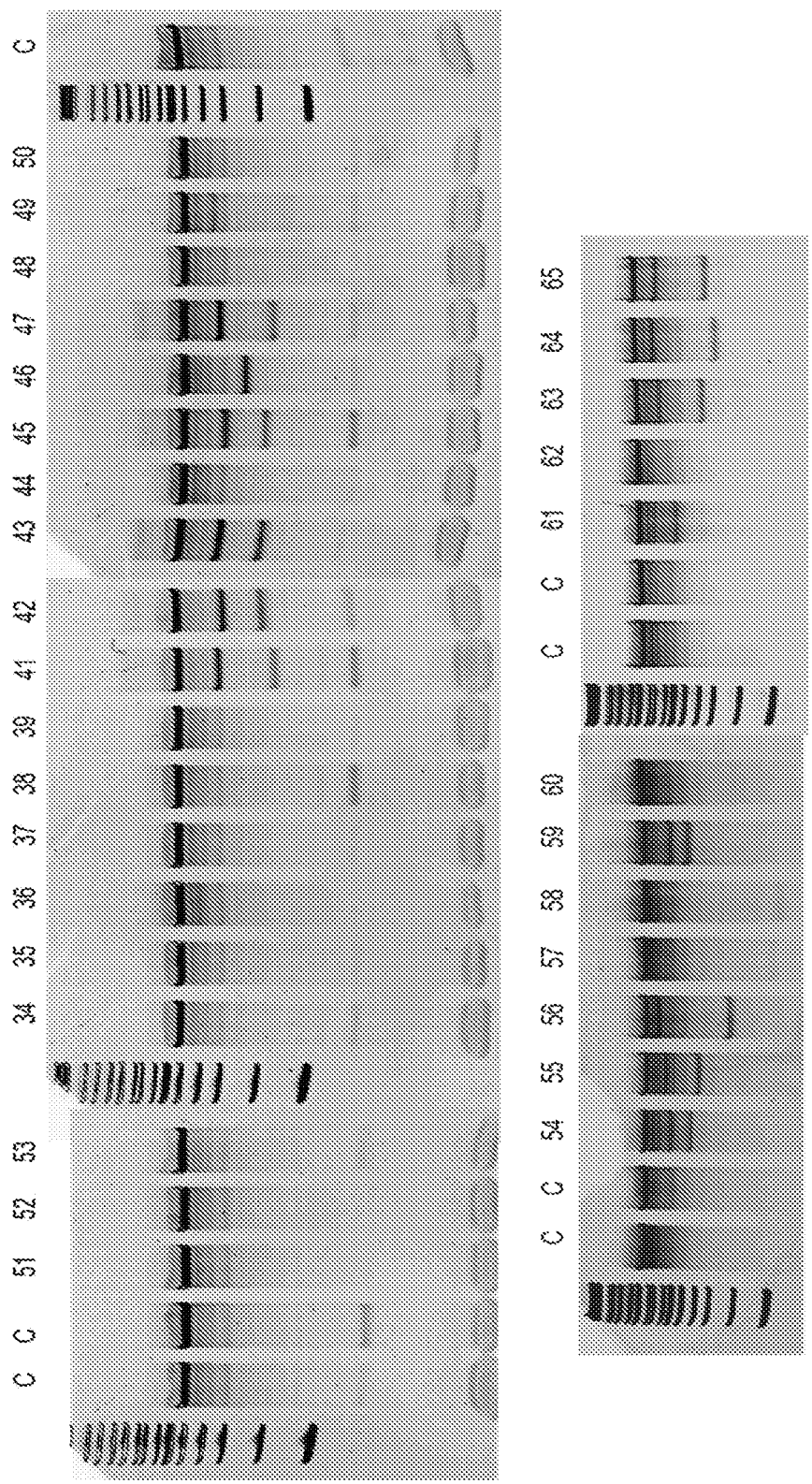
FIG. 7 illustrates a panel of Cpf1 crRNAs showing surveyor nuclease activity throughout the exon.

A large panel of Cpf1 crRNAs were evaluated in HEK293 cells (FIG. 7; see Table 3 for Cpf1 crRNA sequences). All of the Cpf1 crRNAs targeting exon 51 or surrounding introns used are listed in Table 3. As shown in FIG. 7, HEK293 cells treated for 3 days with a panel of crRNAs showed variable activity by the Surveyor® nuclease assay. Cpf1 crRNAs #38, 41, 42, 43, 45, 46, 47, 49, 54, 55, 56, 59, 63, 64, and 65 showed the highest activity indicated by shorted bands.

TABLE 3 crRNA sequences

| # | crRNA Sequence | SEQ ID NO: |
|---|---|---|
| 12 | TTCCATTCTAATGGGTGGCTGTT | 71 |
| 13 | CTCCTCTGTAAAGTGGCGAT | 72 |
| 14 | TTCCATTCTAATGGGTGGCT | 73 |
| 15 | GTATCAATTCACACCAGCAA | 74 |
| 16 | TACCATGTATTGCTAAACAA | 75 |
| 17 | ACTTATTGTTATTGAAATTG | 76 |
| 18 | GCTTGTGTTTCTAATTTTTC | 77 |
| 19 | CAAAAACCCAAAATATTTTA | 78 |
| 20 | TTTAAAATGAAGATTTTCCA | 79 |

TABLE 3-continued crRNA sequences

| # | crRNA Sequence | SEQ ID NO: |
|---|---|---|
| 21 | AAATGAAGATTTTCCACCAA | 80 |
| 22 | CCACCAATCACTTTACTCTC | 81 |
| 23 | CCACCAGTTCTTAGGCAACT | 82 |
| 24 | CATTAATTTATATCCTTGAT | 83 |
| 25 | AGTTATAGCTCTCTTTCAAT | 84 |
| 26 | ATGTATAACAATTCCAACAT | 85 |
| 27 | AAATTACCCTAGATCTTAAA | 86 |
| 28 | GTTGTTGTTGTTAAGGTCAA | 87 |
| 34 | GCTTGTGTTTCTAATTTTTC | 88 |
| 35 | TAATTTTTCTTTTTCTTCTT | 89 |
| 36 | GCAAAAAGGAAAAAGAAGA | 90 |
| 37 | GGGTTTTTGCAAAAAGGAAA | 91 |
| 38 | AGCTCCTACTCAGACTGTTA | 92 |
| 39 | TGCAAAAACCCAAAATATTT | 93 |
| 40 | TGTCACCAGAGTAACAGTCT | 94 |
| 41 | CTTAGTAACCACAGGTTGTG | 95 |
| 42 | TAGTTTGGAGATGGCAGTTT | 96 |
| 43 | GAGATGGCAGTTTCCTTAGT | 97 |
| 44 | CTTGATGTTGGAGGTACCTG | 98 |
| 45 | ATGTTGGAGGTACCTGCTCT | 99 |
| 46 | TAACTTGATCAAGCAGAGAA | 100 |
| 47 | TCTGCTTGATCAAGTTATAA | 101 |
| 48 | TAAAATCACAGAGGGTGATG | 102 |
| 49 | ATATCCTCAAGGTCACCCAC | 103 |
| 50 | ATGATCATCTCGTTGATATC | 104 |
| 51 | TCATACCTTCTGCTTGATGA | 105 |
| 52 | TCATTTTTTCTCATACCTTC | 106 |
| 53 | TGCCAACTTTTATCATTTTT | 107 |
| 54 | AATCAGAAAGAAGATCTTAT | 108 |
| 55 | ATTTCCCTAGGGTCCAGCTT | 109 |
| 56 | GCTCAAATTGTTACTCTTCA | 110 |
| 57 | AGCTCCTACTCAGACTGTTA | 111 |
| 58 | ATTCTAGTACTATGCATCTT | 112 |
| 59 | ACTTAAGTTACTTGTCCAGG | 113 |
| 60 | CCAAGGTCCCAGAGTTCCTA | 114 |
| 61 | TTTCCCTGGCAAGGTCTGAA | 115 |
| 62 | GCTCATTCTCATGCCTGGAC | 116 |
| 63 | TTTAGCAATACATGGTAGAA | 117 |
| 64 | AGCCAAACTCTTATTCATGA | 118 |
| 65 | TAACAATGTGGATACTTTGT | 119 |

Example 5

BCL11a Enhancer Targeting

Potential candidate for increasing fetal globin levels in sickle cell anemia (SCA) were designed. Guide RNAs for Cpf1 were designed to target the BCL11a enhancer region (Table 3) in order to generate potential candidate for increasing fetal globin levels in sickle cell anemia (SCA). These reagents were designed to disrupt the BCL11a enhancer. These reagents will be tested in cell models of SCA.

TABLE 4 guide RNAs targeting the human BCL11a enhancer region

| Target Sequence | Guide RNA | SEQ ID NO |
|---|---|---|
| CACGCCCCACCCTAATCAGAGGCCAAA (SEQ ID NO: 29) | GCCTCTGATTAGGGTGGGGCGTG | 64 |
| CCAAACCCTTCCTGGAGCCTGTGATAAA (SEQ ID NO: 30) | TCACAGGCTCCAGGAAGGGTTTGG | 65 |
| CCTTCCGAAAGAGGCCCCCCTGGGCAAA (SEQ ID NO: 31) | CCCAGGGGGGCCTCTTTCGGAAGG | 66 |
| TCTCCATCACCAAGAGAGCCTTCCGAAA (SEQ ID NO: 32) | GGAAGGCTCTCTTGGTGATGGAGA | 67 |
| TGTTAGCTTGCACTAGACTAGCTTCAAA (SEQ ID NO: 33) | AAGCTAGTCTAGTGCAAGCTAACA | 68 |

TABLE 4-continued guide RNAs targeting the human BCL11a enhancer region

| Target Sequence | Guide RNA | SEQ ID NO |
|---|---|---|
| TTTTCTGGCCTATGTTATTACCTGTATG (SEQ ID NO: 34) | CTGGCCTATGTTATTACCTGTATG | 69 |
| TTTCTGGCCTATGTTATTACCTGTATGG (SEQ ID NO: 35) | TGGCCTATGTTATTACCTGTATGG | 70 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clause:

Clause 1. A Cpf1 guide RNA (gRNA) that targets a dystrophin gene and comprises a polynucleotide sequence corresponding to at least one of SEQ ID NOs: 36-64, 71-119, or a complement thereof.

Clause 2. A DNA targeting composition comprising a Cpf1 endonuclease and at least one Cpf1 gRNA of clause 1.

Clause 3. A DNA targeting composition comprising a first Cpf1 gRNA and a second Cpf1 gRNA, the first Cpf1 gRNA and the second Cpf1 gRNA each comprising a polynucleotide sequence corresponding to at least one of SEQ ID NOs: 36-64, 71-119, or a complement thereof, wherein the first Cpf1 gRNA and the second Cpf1 gRNA comprise different polynucleotide sequences, and wherein the first Cpf1 gRNA and the second Cpf1 gRNA target a dystrophin gene.

Clause 4. The DNA targeting composition of clause 3, wherein the first Cpf1 gRNA comprises a polynucleotide sequence corresponding to SEQ ID NO: 54, SEQ ID NO: 55, or SEQ ID NO: 56, and the second Cpf1 gRNA comprises a polynucleotide sequence corresponding to SEQ ID NO: 62, SEQ ID NO: 63, or SEQ ID NO: 61.

Clause 5. The DNA targeting composition of clause 3 or 4, wherein the first Cpf1 gRNA and the second Cpf1 gRNA are selected from the group consisting of: (i) a first Cpf1 gRNA comprising a polynucleotide sequence set forth in SEQ ID NO: 54 and a second Cpf1 gRNA comprising a polynucleotide sequence set forth in SEQ ID NO: 62; (ii) a first Cpf1 gRNA comprising a polynucleotide sequence set forth in SEQ ID NO: 55 and a second Cpf1 gRNA comprising a polynucleotide sequence set forth in SEQ ID NO: 63; and (iii) a first Cpf1 gRNA comprising a polynucleotide sequence set forth in SEQ ID NO: 56 and a second Cpf1 gRNA comprising a polynucleotide sequence set forth in SEQ ID NO: 61.

Clause 6. The DNA targeting composition of any one of clauses 3 to 5, further comprising a Cpf1 endonuclease.

Clause 7. The DNA targeting composition of clause 2 or 6, wherein the Cpf1 endonuclease recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123).

Clause 8. The DNA targeting composition of clause 7, wherein the Cpf1 endonuclease is derived from a bacterial species selected from the group consisting of *Francisella tularensis* 1, *Francisella tularensis* subsp. *novicida*, *Prevotella albensis*, *Lachnospiraceae bacterium* MC2017 1, *Butyrivibrio proteoclasticus*, *Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum*, *Eubacterium eligens*, *Moraxella bovoculi* 237, *Leptospira inadai*, *Lachnospiraceae bacterium* ND2006, *Porphyromonas crevioricanis* 3, *Prevotella disiens* and *Porphyromonas macacae*.

Clause 9. The DNA targeting composition of any one of clauses 6 to 8, wherein the Cpf1 endonuclease is derived from *Lachnospiraceae bacterium* ND2006 (LbCpf1) or from *Acidaminococcus* (AsCpf1).

Clause 10. The DNA targeting composition of any one of clauses 6 to 9, wherein the Cpf1 endonuclease is encoded by a polynucleotide sequence comprising SEQ ID NO: 124 or SEQ ID NO: 125.

Clause 11. An isolated polynucleotide comprising the Cpf1 gRNA of clause 1 or a polynucleotide sequence encoding the DNA targeting composition of any one of clauses 2 to 10.

Clause 12. A vector comprising the Cpf1 gRNA of clause 1, a polynucleotide sequence encoding the DNA targeting composition of any one of clauses 2 to 10, or the isolated polynucleotide of clause 10.

Clause 13. The vector of clause 12, further comprising a polynucleotide sequence encoding a Cpf1 endonuclease.

Clause 14. A vector encoding: (a) a first Cpf1 guide RNA (gRNA), (b) a second Cpf1 gRNA, and (c) at least one Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), wherein the first Cpf1 gRNA and the second Cpf1 gRNA comprises a polynucleotide sequence corresponding to at least one of SEQ ID NOs: 36-64, 71-119, or a complement thereof, and wherein the first Cpf1 gRNA and the second Cpf1 gRNA comprise different polynucleotide sequences.

Clause 15. The vector of clause 14, wherein the vector is configured to form a first and a second double strand break in a first and a second intron flanking exon 51 of the human DMD gene.

Clause 16. The vector of clause 14 or 15, wherein the first Cpf1 gRNA and the second Cpf1 gRNA are selected from the group consisting of: (i) a first Cpf1 gRNA comprising a polynucleotide sequence set forth in SEQ ID NO: 54 and a second Cpf1 gRNA comprising a polynucleotide sequence set forth in SEQ ID NO: 62; (ii) a first Cpf1 gRNA comprising a polynucleotide sequence set forth in SEQ ID NO: 55 and a second Cpf1 gRNA comprising a polynucleotide sequence set forth in SEQ ID NO: 63; and (iii) a first Cpf1 gRNA comprising a polynucleotide sequence set forth in SEQ ID NO: 56 and a second Cpf1 gRNA comprising a polynucleotide sequence set forth in SEQ ID NO: 61.

Clause 17. The vector of any one of clauses 12 to 16, wherein the vector is a viral vector.

Clause 18. The vector of clause 17, wherein the vector is an Adeno-associated virus (AAV) vector.

Clause 19. The vector of any one of clauses 12 to 18, wherein the vector comprises a tissue-specific promoter operably linked to the polynucleotide sequence encoding the first Cpf1 gRNA, the second Cpf1 gRNA, and/or the Cpf1 endonuclease.

Clause 20. The vector of clause 19, wherein the tissue-specific promoter is a muscle specific promoter.

Clause 21. A cell comprising the Cpf1 gRNA of clause 1, a polynucleotide sequence encoding the DNA targeting composition of any one of clauses 2 to 10, the isolated polynucleotide of clause 11, or the vector of any one of clauses 12 to 20.

Clause 22. A kit comprising the Cpf1 gRNA of clause 1, a polynucleotide sequence encoding the DNA targeting composition of any one of clauses 2 to 10, the isolated polynucleotide of clause 11, the vector of any one of clauses 12 to 20, or the cell of clause 21.

Clause 23. A composition for deleting a segment of a dystrophin gene comprising exon 51, the composition comprising: (a) a first vector comprising a polynucleotide sequence encoding a first Cpf1 guide RNA (gRNA) and a polynucleotide sequence encoding a first Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), and (b) a second vector comprising a polynucleotide sequence encoding a second Cpf1 gRNA and a polynucleotide sequence encoding a second Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), wherein the first Cpf1 gRNA and the second Cpf1 gRNA comprise a polynucleotide sequence corresponding to at least one of SEQ ID NOs: 36-64, 71-119, or a complement thereof, wherein the first Cpf1 gRNA and the second Cpf1 gRNA comprise different polynucleotide sequences, and wherein the first vector and second vector are configured to form a first and a second double strand break in a first intron and a second intron flanking exon 51 of the human DMD gene, respectively, thereby deleting a segment of the dystrophin gene comprising exon 51.

Clause 24. The composition of clause 23, wherein the first Cpf1 gRNA and the second Cpf1 gRNA are selected from the group consisting of: (i) a first Cpf1 gRNA comprising a polynucleotide sequence set forth in SEQ ID NO: 54 and a second Cpf1 gRNA comprising a polynucleotide sequence set forth in SEQ ID NO: 62; (ii) a first Cpf1 gRNA comprising a polynucleotide sequence set forth in SEQ ID NO: 55 and a second Cpf1 gRNA comprising a polynucleotide sequence set forth in SEQ ID NO: 63; and (iii) a first Cpf1 gRNA comprising a polynucleotide sequence set forth in SEQ ID NO: 56 and a second Cpf1 gRNA comprising a polynucleotide sequence set forth in SEQ ID NO: 61.

Clause 25. The composition of clause 23 or 24, wherein the first Cpf1 endonuclease and the second Cpf1 endonuclease are the same.

Clause 26. The composition of clause 23 or 24, wherein the first Cpf1 endonuclease and the second Cpf1 endonuclease are different.

Clause 27. The composition of clause 25 or 26, wherein the first Cpf1 endonuclease and/or the second Cpf1 endonuclease are CPF1 endonuclease from *Lachnospiraceae bacterium* ND2006 (LbCpf1) and/or from *Acidaminococcus* (AsCpf1).

Clause 28. The composition of any one of clauses 25 to 27, wherein the first Cpf1 endonuclease and/or the second Cpf1 endonuclease are encoded by a polynucleotide sequence comprising SEQ ID NO: 124 or SEQ ID NO: 125.

Clause 29. The composition of any one of clauses 23 to 28, wherein the first vector and/or the second vector is a viral vector.

Clause 30. The composition of clause 29, wherein the first vector and/or the second vector is an Adeno-associated virus (AAV) vector.

Clause 31. The composition of clause 30, wherein the AAV vector is an AAV8 vector or an AAV9 vector.

Clause 32. The composition of any one of clauses 23 to 31, wherein the dystrophin gene is a human dystrophin gene.

Clause 33. The composition of any one of clauses 23 to 32, for use in a medicament.

Clause 34. The composition of any one of clauses 23 to 32, for use in the treatment of Duchenne Muscular Dystrophy.

Clause 35. A cell comprising the composition of any one of clauses 23 to 34.

Clause 36. A modified adeno-associated viral vector for genome editing a mutant dystrophin gene in a subject comprising a first polynucleotide sequence encoding the Cpf1 gRNA of clause 1, and a second polynucleotide sequence encoding a Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123).

Clause 37. A method of correcting a mutant dystrophin gene in a cell, the method comprising administering to a cell the Cpf1 gRNA of clause 1, a polynucleotide sequence encoding the DNA targeting composition of any one of clauses 2 to 10, the isolated polynucleotide of clause 11, the vector of any one of clauses 12 to 20, the composition of any one of clauses 23 to 34, or the modified adeno-associated viral vector of clause 36.

Clause 38. The method of clause 37, wherein correcting the mutant dystrophin gene comprises nuclease-mediated non-homologous end joining or homology-directed repair.

Clause 39. A method of genome editing a mutant dystrophin gene in a subject, the method comprising administering to the subject a genome editing composition comprising the Cpf1 gRNA of clause 1, a polynucleotide sequence encoding the DNA targeting composition of any one of clauses 2 to 10, the isolated polynucleotide of clause 11, the vector of any one of clauses 12 to 20, the composition of any one of clauses 23 to 34, or the modified adeno-associated viral vector of clause 36.

Clause 40. The method of clause 39, wherein the genome editing composition is administered to the subject intramuscularly, intravenously, or a combination thereof.

Clause 41. The method of clause 39 or 40, wherein the genome editing comprises nuclease-mediated non-homologous end joining or homology-directed repair.

Clause 42. A method of treating a subject in need thereof having a mutant dystrophin gene, the method comprising administering to the subject the Cpf1 gRNA of clause 1, a polynucleotide sequence encoding the DNA targeting composition of any one of clauses 2 to 10, the isolated polynucleotide of clause 11, the vector of any one of clauses 12 to 20, the composition of any one of clauses 23 to 34, or the modified adeno-associated viral vector of clause 36.

Clause 43. A method of correcting a mutant dystrophin gene in a cell, comprising administering to the cell: (a) a first vector comprising a polynucleotide sequence encoding a first Cpf1 guide RNA (gRNA) and a polynucleotide sequence encoding a first Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), and (b) a second vector comprising a polynucleotide sequence encoding a second Cpf1 gRNA and a polynucleotide sequence encoding a second Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), wherein the first Cpf1 gRNA and the second Cpf1 gRNA comprises a polynucleotide sequence corresponding to at least one of SEQ ID NOs: 36-64, 71-119, or a complement thereof, and the vector is configured to form a first and a second double strand break in a first and a second intron flanking exon 51 of the human dystrophin gene, respectively, thereby deleting a segment of the dystrophin gene comprising exon 51 and correcting the mutant dystrophin gene in a cell.

Clause 44. The method of clause 43, wherein the first Cpf1 gRNA and the second Cpf1 gRNA are selected from the group consisting of: (i) a first Cpf1 gRNA comprising a polynucleotide sequence set forth in SEQ ID NO: 54 and a second Cpf1 gRNA comprising a polynucleotide sequence set forth in SEQ ID NO: 62; (ii) a first Cpf1 gRNA comprising a polynucleotide sequence set forth in SEQ ID NO: 55 and a second Cpf1 gRNA comprising a polynucleotide sequence set forth in SEQ ID NO: 63; and (iii) a first Cpf1 gRNA comprising a polynucleotide sequence set forth in SEQ ID NO: 56 and a second Cpf1 gRNA comprising a polynucleotide sequence set forth in SEQ ID NO: 61.

Clause 45. The method of clause 43 or 44, wherein the mutant dystrophin gene comprises a premature stop codon, disrupted reading frame, an aberrant splice acceptor site, or an aberrant splice donor site.

Clause 46. The method of clause 45, wherein the mutant dystrophin gene comprises a frameshift mutation which causes a premature stop codon and a truncated gene product.

Clause 47. The method of clause 43 or 44, wherein the mutant dystrophin gene comprises a deletion of one or more exons which disrupts the reading frame.

Clause 48. The method of any one of clauses 43 to 47, wherein the correction of the mutant dystrophin gene comprises a deletion of a premature stop codon, correction of a disrupted reading frame, or modulation of splicing by disruption of a splice acceptor site or disruption of a splice donor sequence.

Clause 49. The method of clause 48, wherein the correction of the mutant dystrophin gene comprises deletion of exon 51.

Clause 50. The method of any one of clauses 43 to 49, wherein the correction of the mutant dystrophin gene comprises nuclease mediated non-homologous end joining or homology-directed repair.

Clause 51. The method of any one of clauses 43 to 50, wherein the cell is a myoblast cell.

Clause 52. The method of any one of clauses 43 to 51, wherein the cell is from a subject suffering from Duchenne muscular dystrophy.

Clause 53. A method of treating a subject in need thereof having a mutant dystrophin gene, the method comprising administering to the subject: (a) a first vector comprising a polynucleotide sequence encoding a first Cpf1 guide RNA (gRNA) and a polynucleotide sequence encoding a first Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), and (b) a second vector comprising a polynucleotide sequence encoding a second Cpf1 gRNA and a polynucleotide sequence encoding a second Cpf1 endonuclease that recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123), wherein the first Cpf1 gRNA and the second Cpf1 gRNA comprises a polynucleotide sequence corresponding to at least one of SEQ ID NOs: 36-64, 71-119, or a complement thereof, and the first vector and the second vector are configured to form a first and a second double strand break in a first and a second intron flanking exon 51 of the human dystrophin gene, respectively, thereby deleting a segment of the dystrophin gene comprising exon 51 and treating the subject.

Clause 54. The method of clause 53, wherein the first Cpf1 gRNA and the second Cpf1 gRNA are selected from the group consisting of: (i) a first Cpf1 gRNA comprising a polynucleotide sequence set forth in SEQ ID NO: 54, and a second Cpf1 gRNA comprising a polynucleotide sequence set forth in SEQ ID NO: 62; (ii) a first Cpf1 gRNA comprising a polynucleotide sequence set forth in SEQ ID NO: 55, and a second Cpf1 gRNA comprising a polynucleotide sequence set forth in SEQ ID NO: 63; and (iii) a first Cpf1 gRNA comprising a polynucleotide sequence set forth in SEQ ID NO: Clause 56, and a second Cpf1 gRNA comprising a polynucleotide sequence set forth in SEQ ID NO: 61.

Clause 55. The method of clause 53 or 54, wherein the subject is suffering from Duchenne muscular dystrophy.

Clause 56. The method of any one of clauses 53 to 55, wherein the first vector and second vector are administered to the subject intramuscularly, intravenously, or a combination thereof.

Clause 57. A Cpf1 guide RNA (gRNA) that targets an enhancer of the B-cell lymphoma/leukemia 11A (BCL11a) gene and comprises a polynucleotide sequence corresponding to at least one of SEQ ID NOs: 65-70, or a complement thereof.

Clause 58. A method of disrupting an enhancer of a B-cell lymphoma/leukemia 11A gene in a cell, the method comprising administering to the cell at least one Cpf1 gRNA of clause 57 and a Cpf1 endonuclease.

What is claimed is:

1. A DNA targeting composition comprising a first Cpf1 gRNA and a second Cpf1 gRNA selected from the group consisting of:

(i) a first Cpf1 gRNA comprising a polynucleotide encoded by the sequence of SEQ ID NO: 54 and a second Cpf1 gRNA comprising a polynucleotide encoded by the sequence of SEQ ID NO: 62;

(ii) a first Cpf1 gRNA comprising a polynucleotide encoded by the sequence of SEQ ID NO: 55 and a second Cpf1 gRNA comprising a polynucleotide encoded by the sequence of SEQ ID NO: 63; and (iii) a first Cpf1 gRNA comprising a polynucleotide encoded by the sequence of SEQ ID NO: 56 and a second Cpf1 gRNA comprising a polynucleotide encoded by the sequence of SEQ ID NO: 61.

2. The DNA targeting composition of claim 1, further comprising a Cpf1 endonuclease.

3. The DNA targeting composition of claim 2, wherein the Cpf1 endonuclease recognizes a Protospacer Adjacent Motif (PAM) of TTTA (SEQ ID NO: 120), TTTG (SEQ ID NO: 121), TTTC (SEQ ID NO: 122), or TTTT (SEQ ID NO: 123).

4. The DNA targeting composition of claim 3, wherein the Cpf1 endonuclease is derived from a bacterial species selected from the group consisting of *Francisella tularensis* 1, *Francisella tularensis* subsp. *novicida*, *Prevotella albensis*, *Lachnospiraceae bacterium* MC2017 1, *Butyrivibrio proteoclasticus*, *Peregrinibacteria bacterium* GW2011_GWA2_33_10, *Parcubacteria bacterium* GW2011_GWC2_44_1 7, *Smithella* sp. SCADC, *Acidaminococcus* sp. BV3L6, *Lachnospiraceae bacterium* MA2020, *Candidatus Methanoplasma termitum*, *Eubacterium eligens*, *Moraxella bovoculi* 237, *Leptospira inadai*, *Lachnospiraceae bacterium* ND2006, *Porphyromonas creviorcanis* 3, *Prevotella disiens* and *Porphyromonas macacae*.

5. The DNA targeting composition of claim 2, wherein the Cpf1 endonuclease is derived from *Lachnospiraceae bacterium* ND2006 (LbCpf1) or from *Acidaminococcus* (AsCpf1).

6. The DNA targeting composition of claim 2, wherein the Cpf1 endonuclease is encoded by a polynucleotide sequence comprising SEQ ID NO: 124 or SEQ ID NO: 125.

7. A vector encoding the DNA targeting composition of claim 1.

8. The vector of claim 7, further comprising a polynucleotide sequence encoding a Cpf1 endonuclease.

9. The DNA targeting composition of claim 7, wherein the vector is a viral vector.

10. The DNA targeting composition of claim 9, wherein the vector is an Adeno-associated virus (AAV) vector.

11. The vector of claim 9, wherein the vector comprises a tissue-specific promoter operably linked to the polynucleotide sequence encoding the first Cpf1 gRNA, the second Cpf1 gRNA and/or the Cpf1 endonuclease.

12. The DNA targeting composition of claim 11, wherein the tissue-specific promoter is a muscle specific promoter.

* * * * *